United States Patent [19]
Matteucci et al.

[11] Patent Number: 5,646,269
[45] Date of Patent: Jul. 8, 1997

[54] METHOD FOR OLIGONUCLEOTIDE ANALOG SYNTHESIS

[75] Inventors: Mark D. Matteucci, Burlingame; Jiancun Zhang, San Francisco, both of Calif.

[73] Assignee: Gilead Sciences, Inc., Foster City, Calif.

[21] Appl. No.: 234,452

[22] Filed: Apr. 28, 1994

[51] Int. Cl.$^6$ .......................... C07H 19/06; C07H 19/16
[52] U.S. Cl. .................. 536/26.7; 536/26.72; 536/26.74; 536/26.8; 536/27.6; 536/27.8; 536/27.81; 536/28.1; 536/28.5; 536/28.53; 536/28.54; 544/242; 544/264; 544/265; 544/269; 544/294; 544/296; 544/302; 544/327
[58] Field of Search ........................... 536/25.3, 26.72, 536/26.8, 27.6, 27.8, 27.81, 28.1, 28.5, 28.53, 28.54, 26.7, 26.74; 544/242, 243, 245, 264, 265, 269, 302, 327, 294, 296

[56] References Cited

U.S. PATENT DOCUMENTS 5,264,564 11/1993 Matteucci .
5,484,908 1/1996 Froehler et al. .

FOREIGN PATENT DOCUMENTS

| WO 91/06556 | 5/1991 | WIPO . |
| WO 91/10671 | 7/1991 | WIPO . |
| WO 92/03452 | 3/1992 | WIPO . |
| WO 92/03568 | 3/1992 | WIPO . |
| WO 93/07883 | 4/1993 | WIPO . |
| WO 93/24508 | 9/1993 | WIPO . |

OTHER PUBLICATIONS

Chavis et al., "Synthesis of 2',3'–Differentiated Ribonucleosides via Glycosylation Reactions with 2–O–Me or 2–O–TBDMS Ribofuranose Derivatives. 1. Pyrimidine Series," J Org Chem 47:202–206 (1982).
Froehler et al., "Triple–Helix Formation by Oligodeoxynucleotides Containing the Carbocyclic Analogs of Thymidine and 5–Methyl–2'–deoxycytidine," J Am Chem Soc 114:8320–8322 (1992).
Ikehara et al., "Studies of Nucleosides and Nucleotides—LXXIV," Tetrahedron 34:1133–1138 (1978).
Inoue et al., "Synthesis and hybridization studies on two complementary nona(2'-methyl)ribonucleotides," Nuc Acids Res 15:6131–6148 (1987).
Morvan et al., "Solid Phase Synthesis of Alpha–Anomeric Oligodeoxyribonucleotides," Nuc Acids Res 16(3):833–847 (1988).
Praseuth et al., "Sequence–specific binding and photo-crosslinking of a and b oligodeoxynucleotides to the major groove of DNA via triple–helix formation," Proc Natl Acad Sci 85:1349–1353 (1988).
Sagi et al, "Biochemical properties of oligo[(+)-carbocyclic-thymidylates] and their complexes," Nuc Acids Res 18:2133–2140 (1990).
Shibahara et al., "Site–directed cleavage of RNA," Nuc Acids Res 15(11):4403–4415 (1987).
Sproat et al., "New Synthetic routes to synthons suitable for 2'–O–allyloligoribonucleotide assembly," Nuc Acids Res 19:733–738 (1991).
Uhlmann et al, "Antisense Oligonucleotides: A New Therapeutic Principle," Chem Rev 90:543–584 (1990).
Baldwin et al, "Organometallic Azides. III. Methylphenylphosphinic Azide and Related Compounds", J. Org. Chem. 32:2172–2176 (Jul. 1967).
Baldwin et al, "Application of the Hammett Equation to Organophosphorus–Substituted Phosphinic and Benzoic Acids", J. Org. Chem. 32:2176–2180 (1967).
Quaedflieg et al, "An Alternative Approach towards the Synthesis of (3'→5') Methylene Acetal Linked Dinucleosides", Tetrahedron Letters 33(21):3081–3084 (1992).
Quaedflieg et al, "An Alternative Route to the Preparation of (3'→5') Methylene Acetal Linked Di–and Trinucleosides", Synthesis 627–633 (Jun. 1993).
Matsueda et al., "3–Nitro–2–Pyridinesulfenyl Group for Protection and Activation of the Thiol Function of Cysteine," Chemistry Letters, Tokyo JP 6:737–740 (1981).

*Primary Examiner*—James Wilson
*Attorney, Agent, or Firm*—Daryl D. Muenchau

[57] ABSTRACT

The present invention is directed to improved methods to synthesize oligonucleotide analogs having an acetal linkage, such as a 3',5'-formacetal (3' —O—CH$_2$—O— 5'), 3',5'-thioformacetal (3' —S—CH$_2$—O— 5') or an analogous 2',5' linkage between adjacent nucleoside analog residues. Compositions comprising 5', 3' and 2' phosphinate nucleoside analogs useful in the methods are also provided.

21 Claims, 22 Drawing Sheets

Diazine

Triazine

Phenopyrroline

Pyridinopyrroline

Phenothiazine and Phenoxazine oxazine   $R^{17}$ = OH   $R^{16}$ = Br   $X^1$ = O
thiazine  $R^{17}$ = SH   $R^{16}$ = I    $X^1$ = S Phenoxazine

METHOD FOR OLIGONUCLEOTIDE ANALOG SYNTHESIS

BACKGROUND OF THE INVENTION

The present invention relates to an improved method for synthesis of oligonucleotide analogs having one or more formacetal or thioformacetal internucleotide linkages.

Methods used for the synthesis of acetal linkages have one or more disadvantages including relatively low yields of product per coupling cycle and coupling conditions that result in side products for certain nucleoside analogs, such as purine nucleoside analogs.

OBJECTS OF THE INVENTION

It is an object of the invention to provide improved methods for synthesis of 3',5'- and 2',5'-formacetal linkages, 3',5'- and 2',5'-thioformacetal linkages, 5',3'-and 5',2'-thioformacetal linkages (collectively the "acetal linkages") in oligonucleotide analogs containing one or more acetal linkages.

Another object of the invention is to provide new phosphinate nucleoside analog intermediates and methods for their synthesis that are useful in synthesis of the acetal linkages.

Another object of the invention is to provide methods for solid phase and liquid phase synthesis of oligonucleotide analogs containing one or more acetal linkages.

SUMMARY OF THE INVENTION

Figure 1:
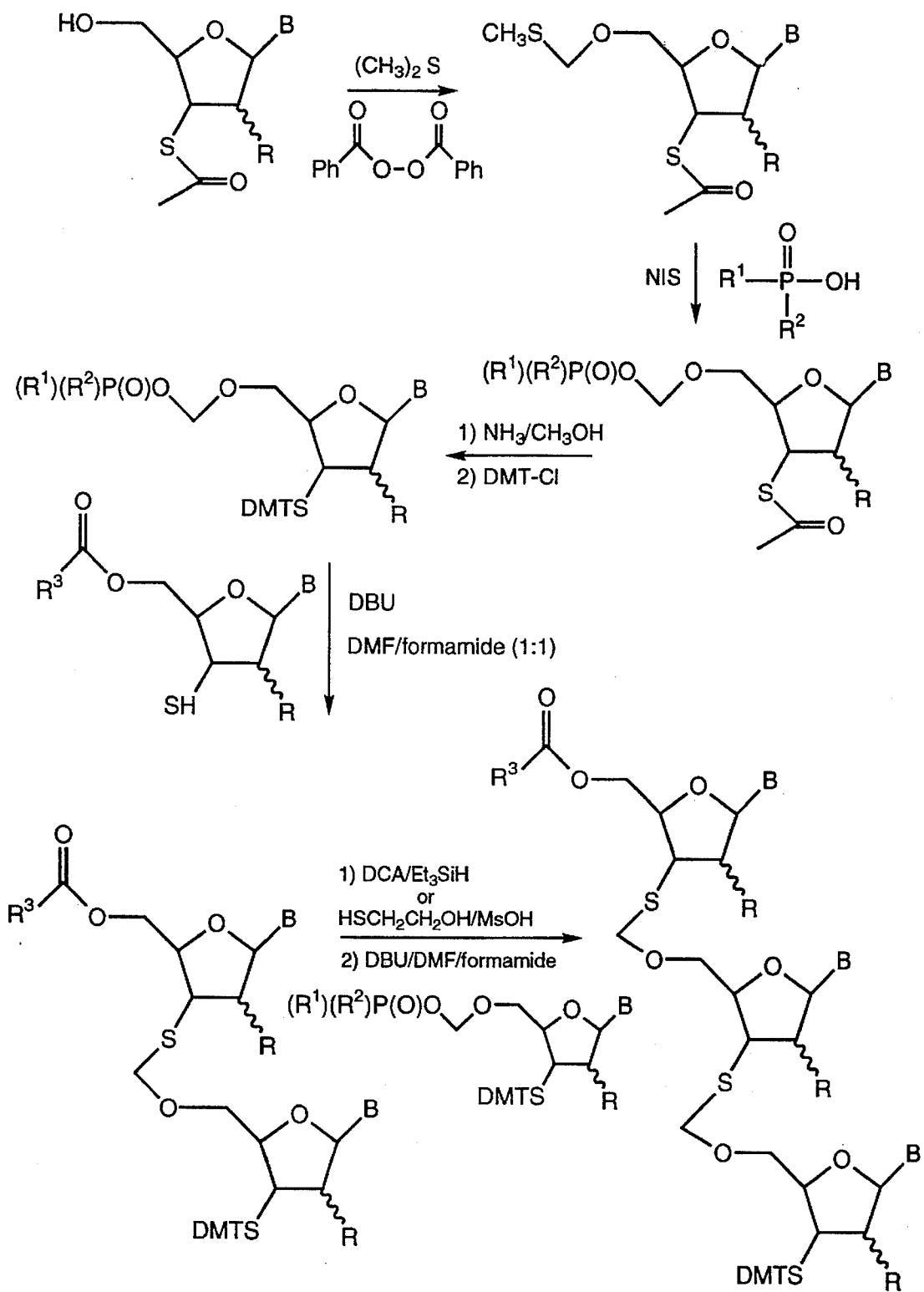
FIG. 1. Synthesis of a 3',5'-thioformacetal linked oligonucleotide analog.
Figure 2:
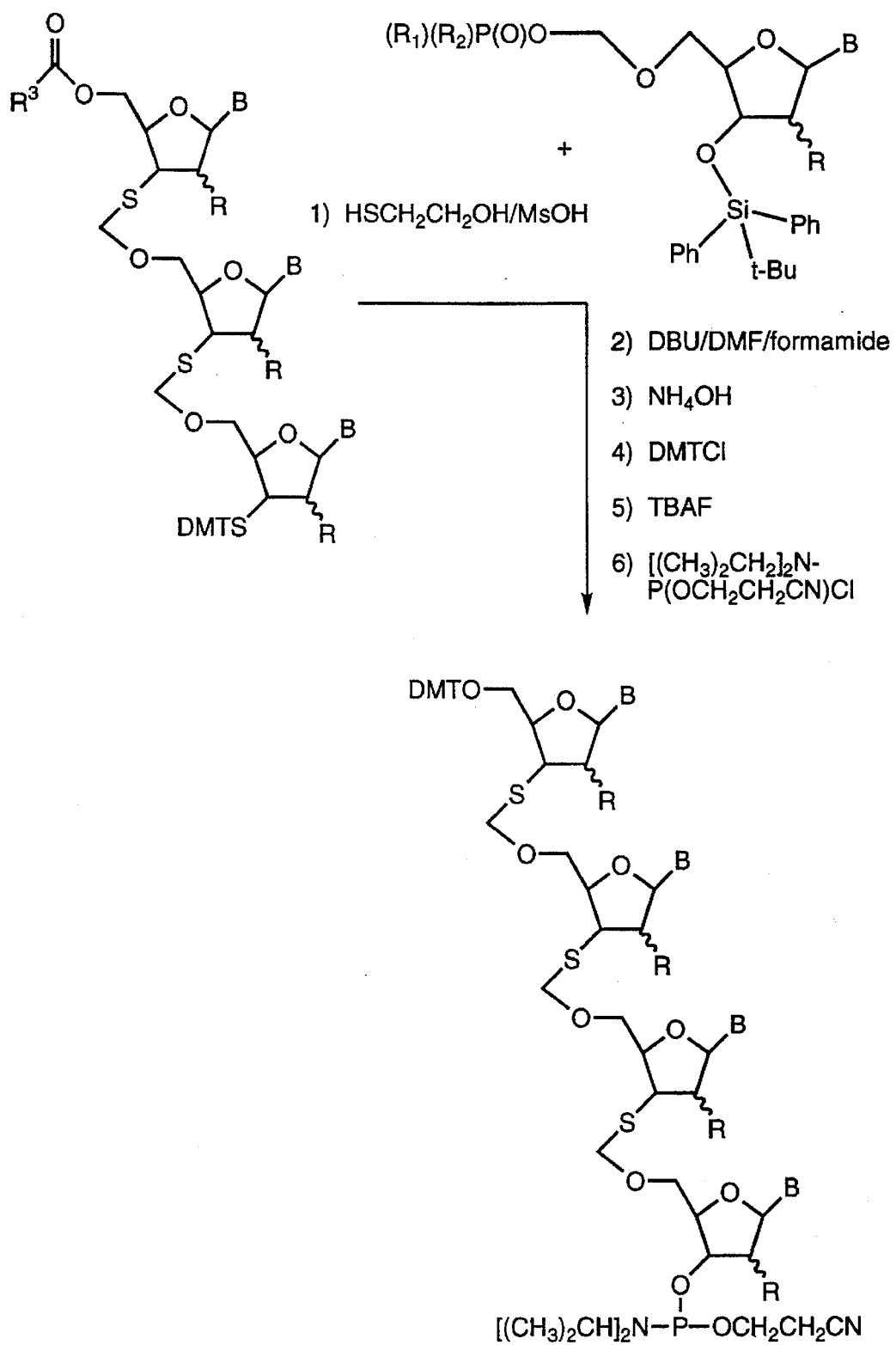
FIG. 2. 3',5'-thioformacetal linked synthon suitable for oligonucleotide analog synthesis via a solid phase phosphoramidite method.
Figure 3:
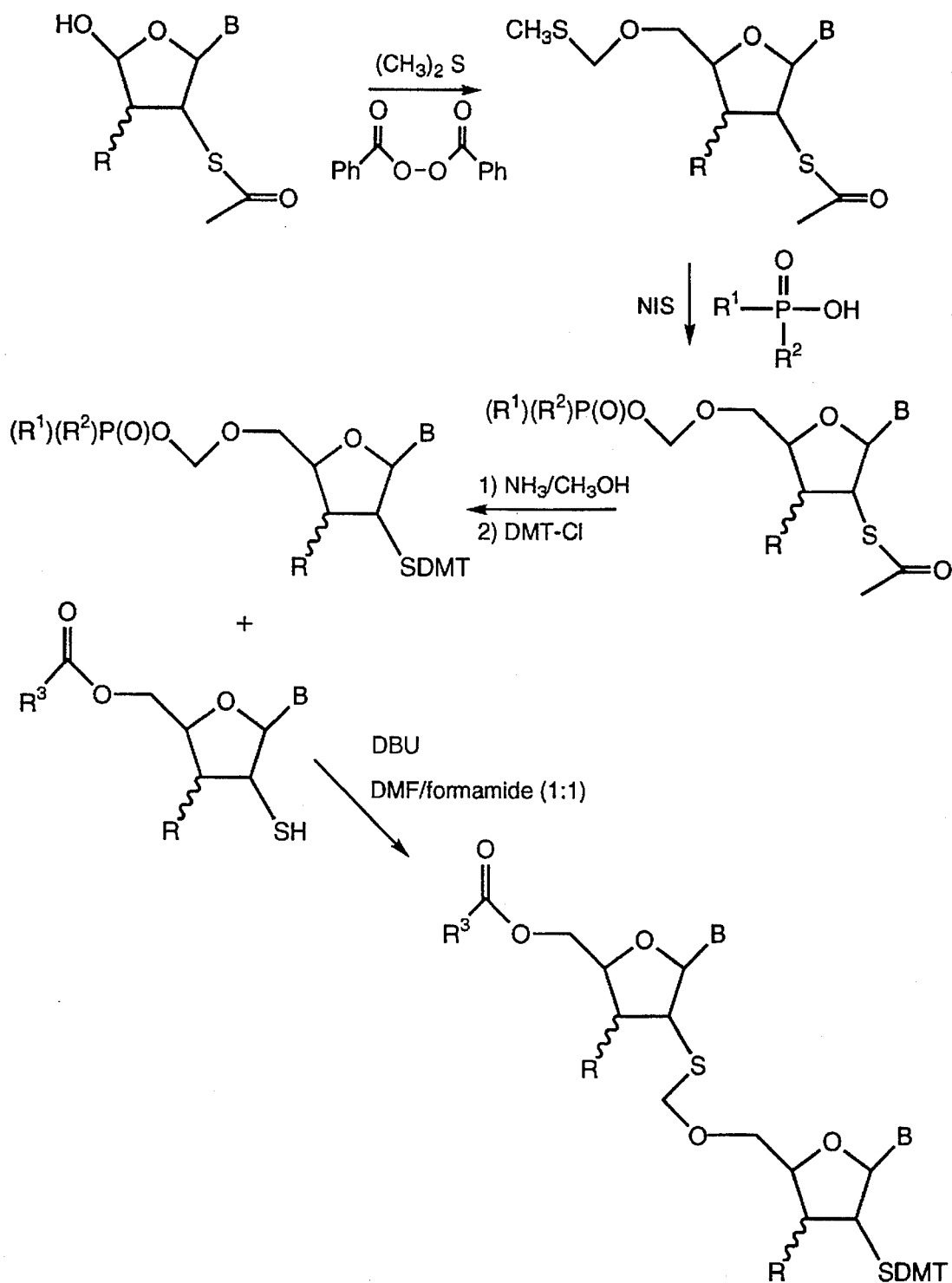
FIG. 3. Synthesis of a 3',5'-formacetal linked oligonucleotide analog.
Figure 4:
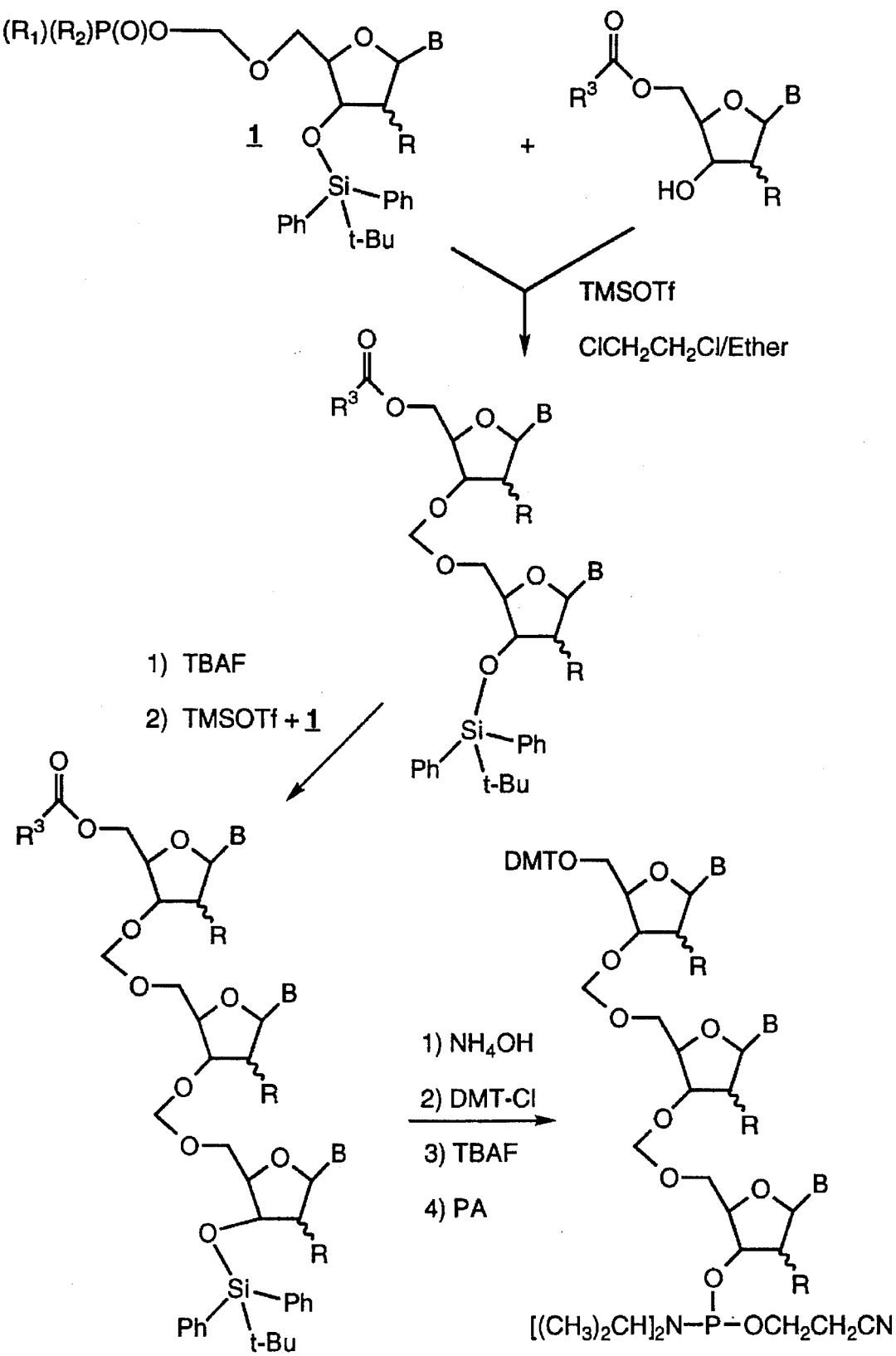
FIG. 4. Synthesis of a 5',3'-thioformacetal linked oligonucleotide analog.
Figure 5:
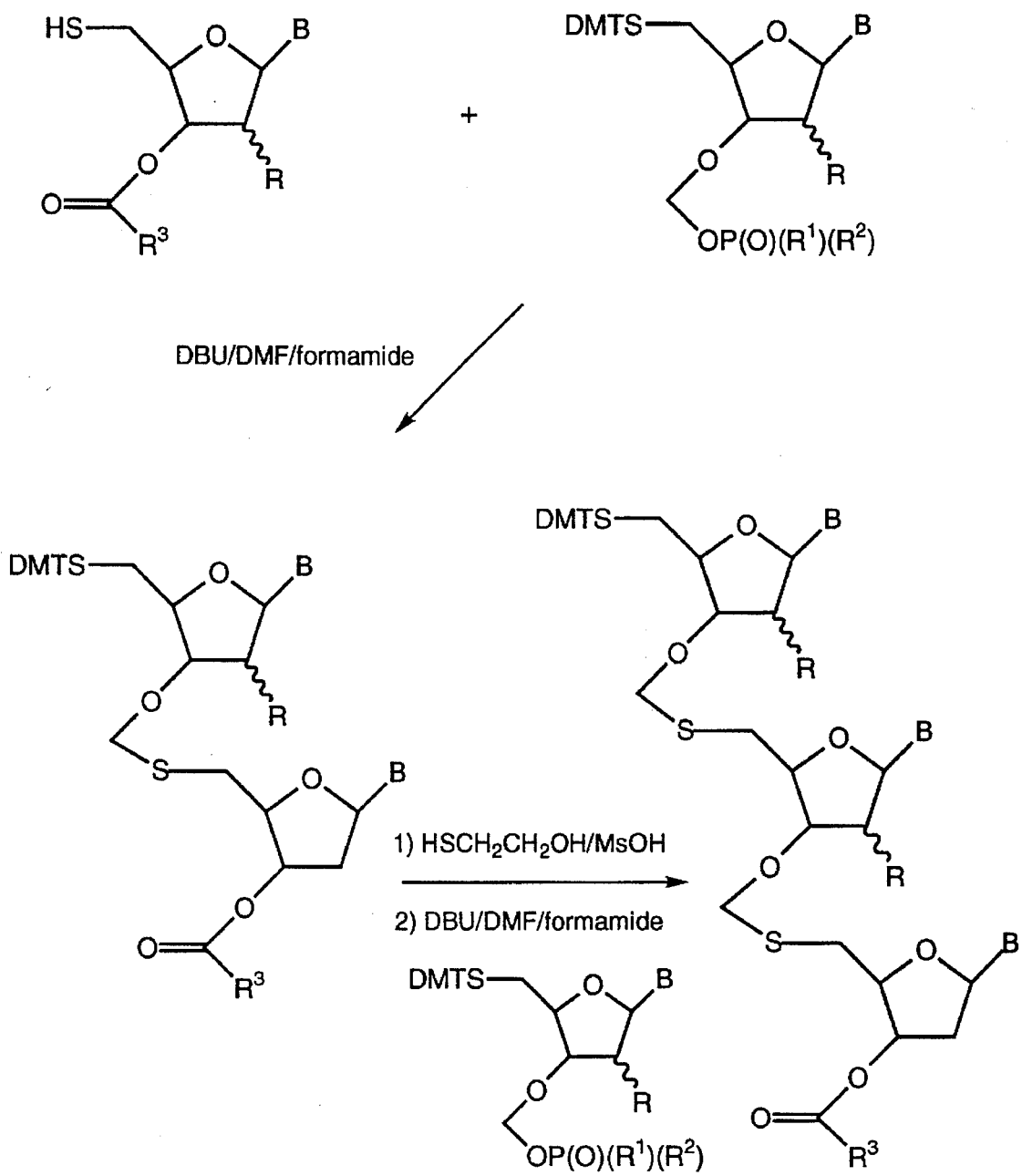
FIG. 5. 5',3'-thioformacetal linked synthon suitable for oligonucleotide analog synthesis via a solid phase phosphoramidite method.
Figure 6:
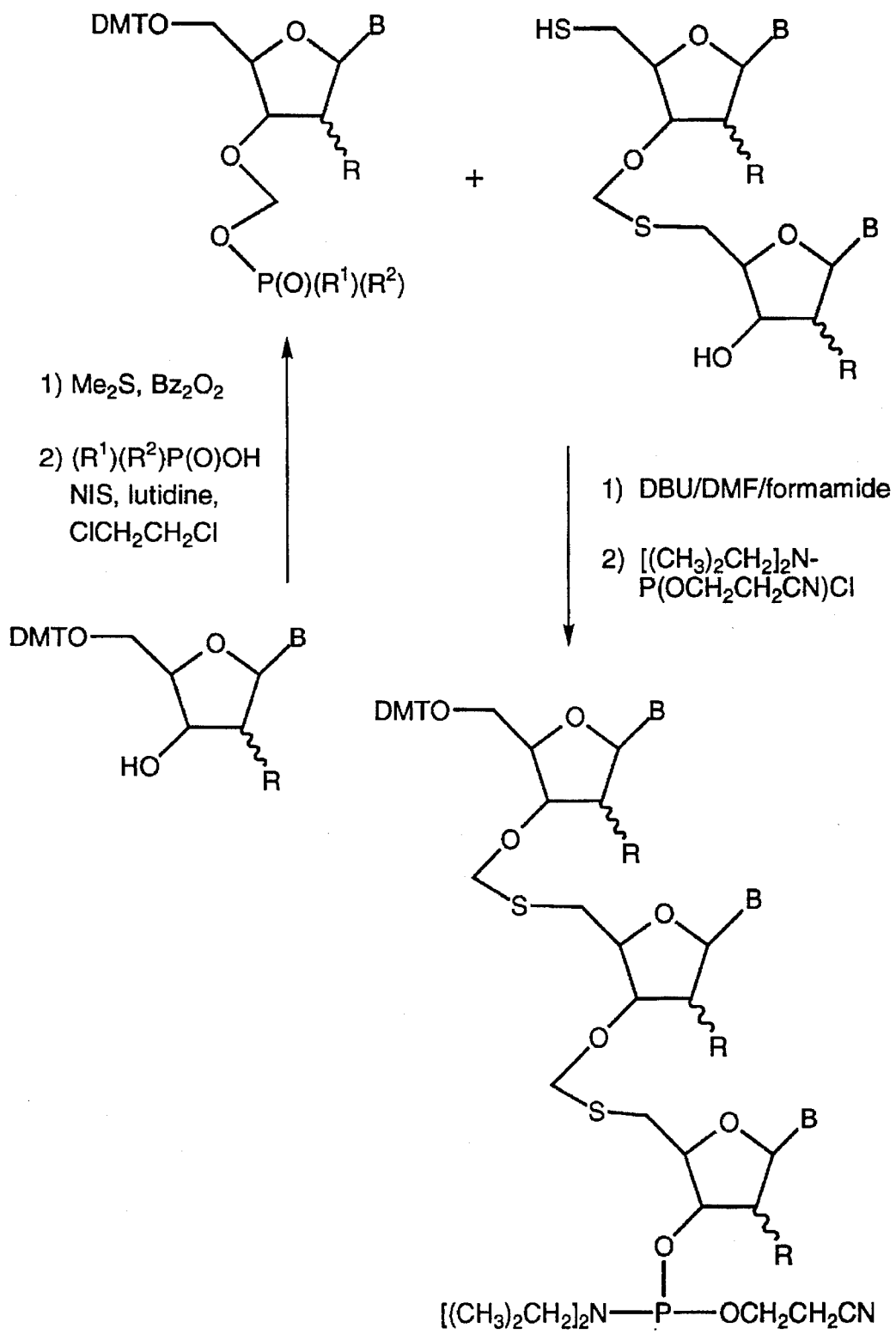
FIG. 6. Synthesis of 5',3' thioformacetal linked oligonucleotide dimers.
Figure 7:
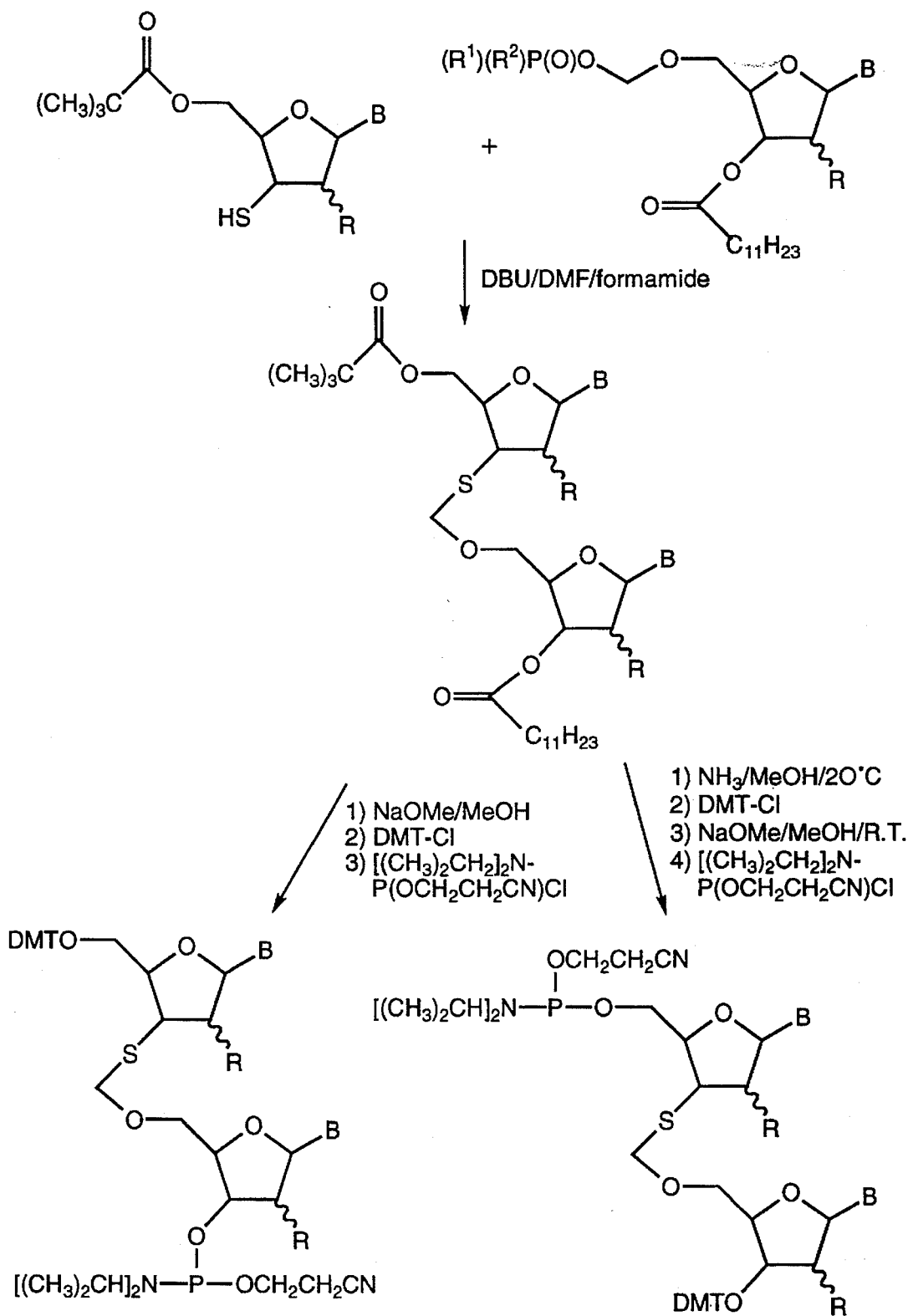
FIG. 7. Synthesis of 3',5' thioformacetal linked oligonucleotide dimers.
Figure 8:
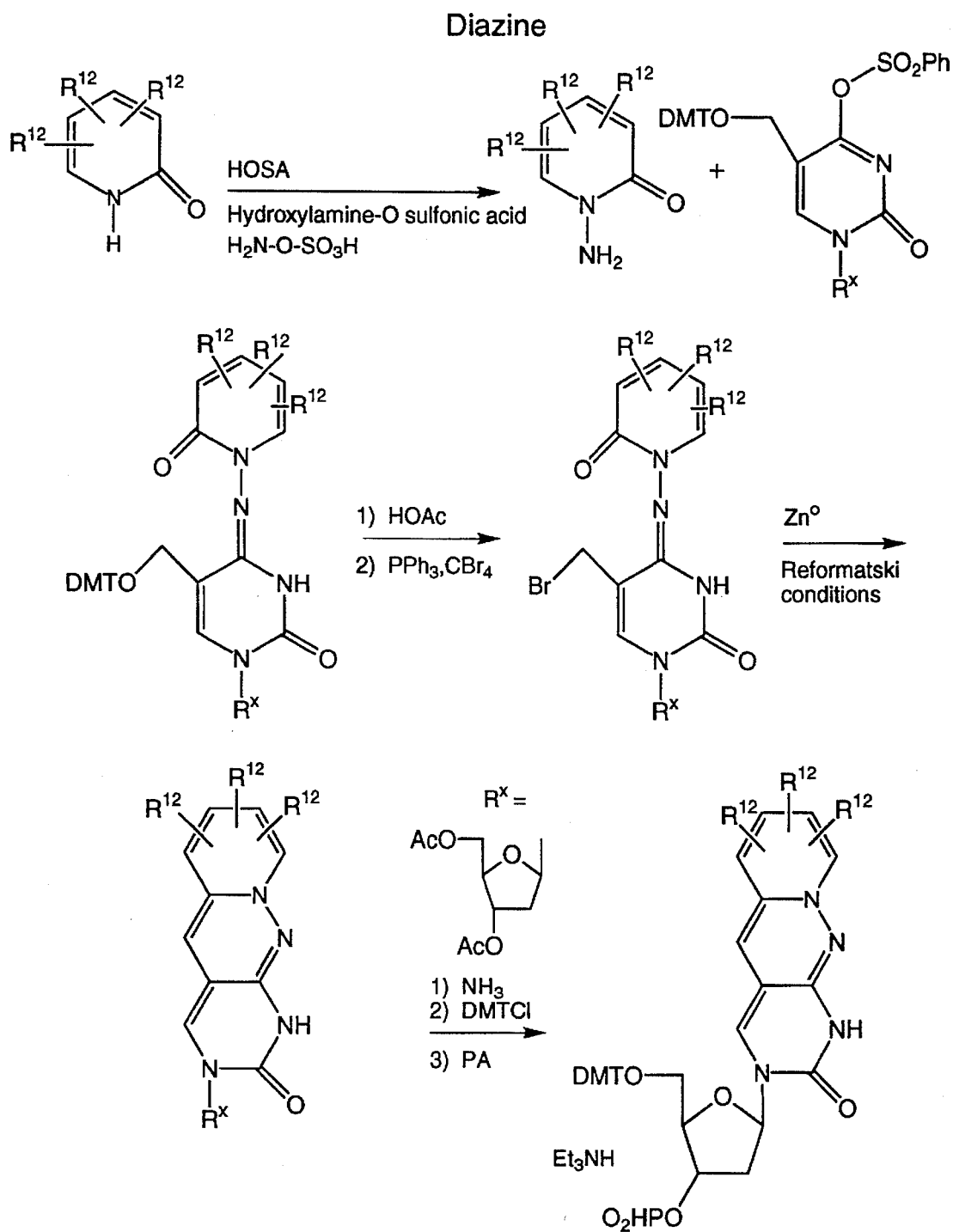
FIG. 8. shows synthesis of a diazine tricyclic cytosine nucleomonomer.
Figure 9:
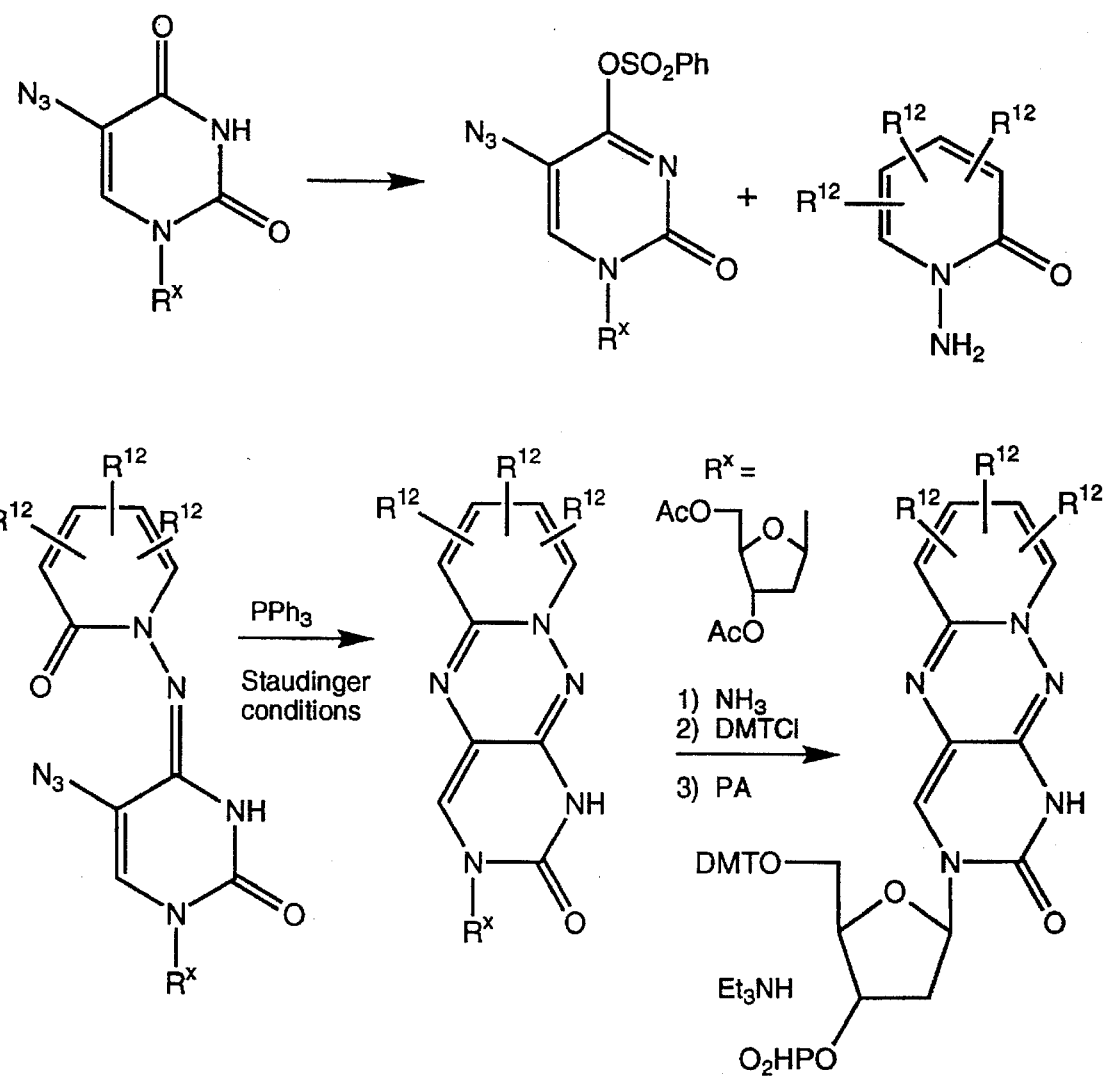
FIG. 9. shows synthesis of a triazine tricyclic cytosine nucleomonomer.
Figure 10:
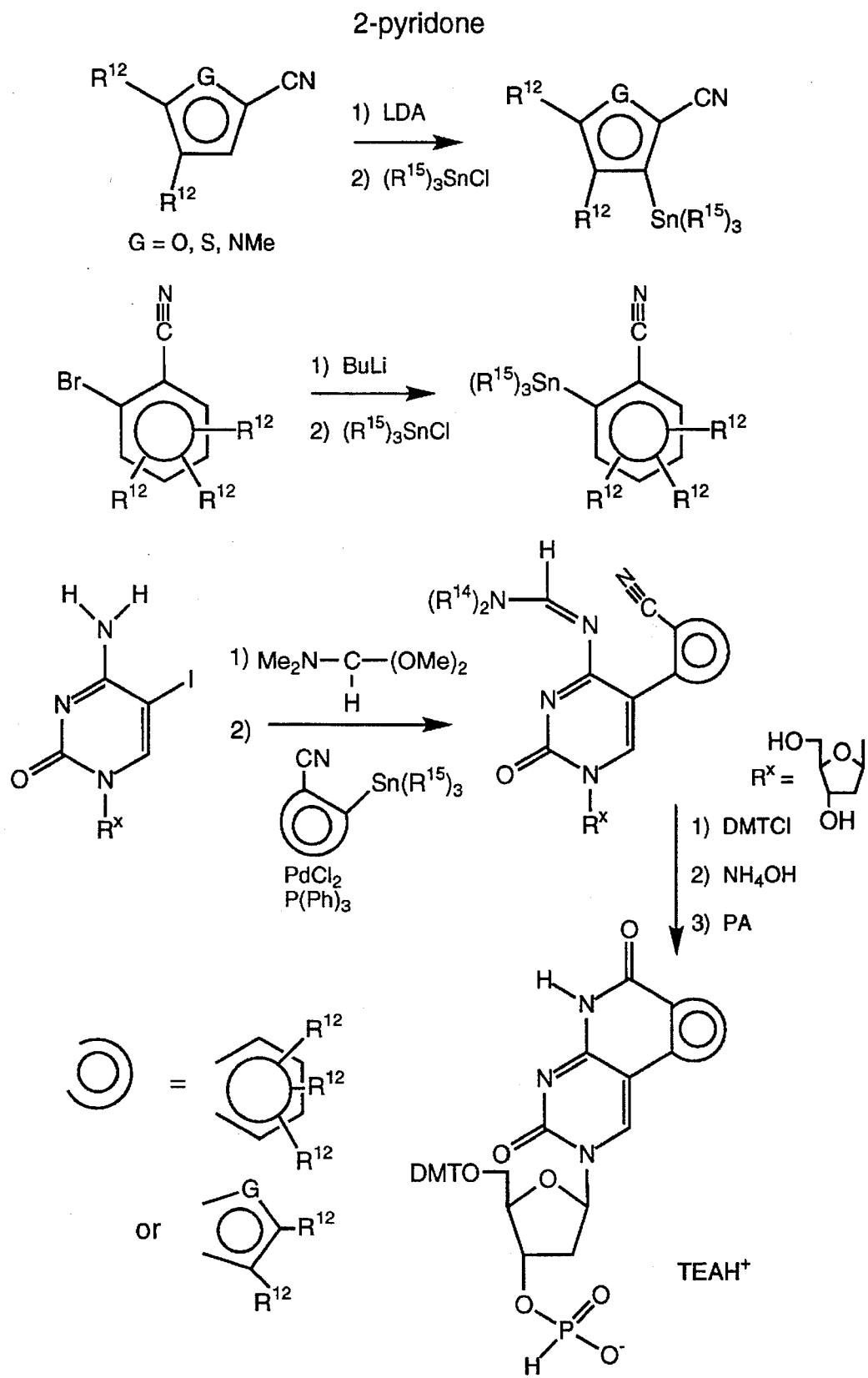
FIG. 10. shows synthesis of a 2-pyridone tricyclic cytosine nucleomonomer.
Figure 11:
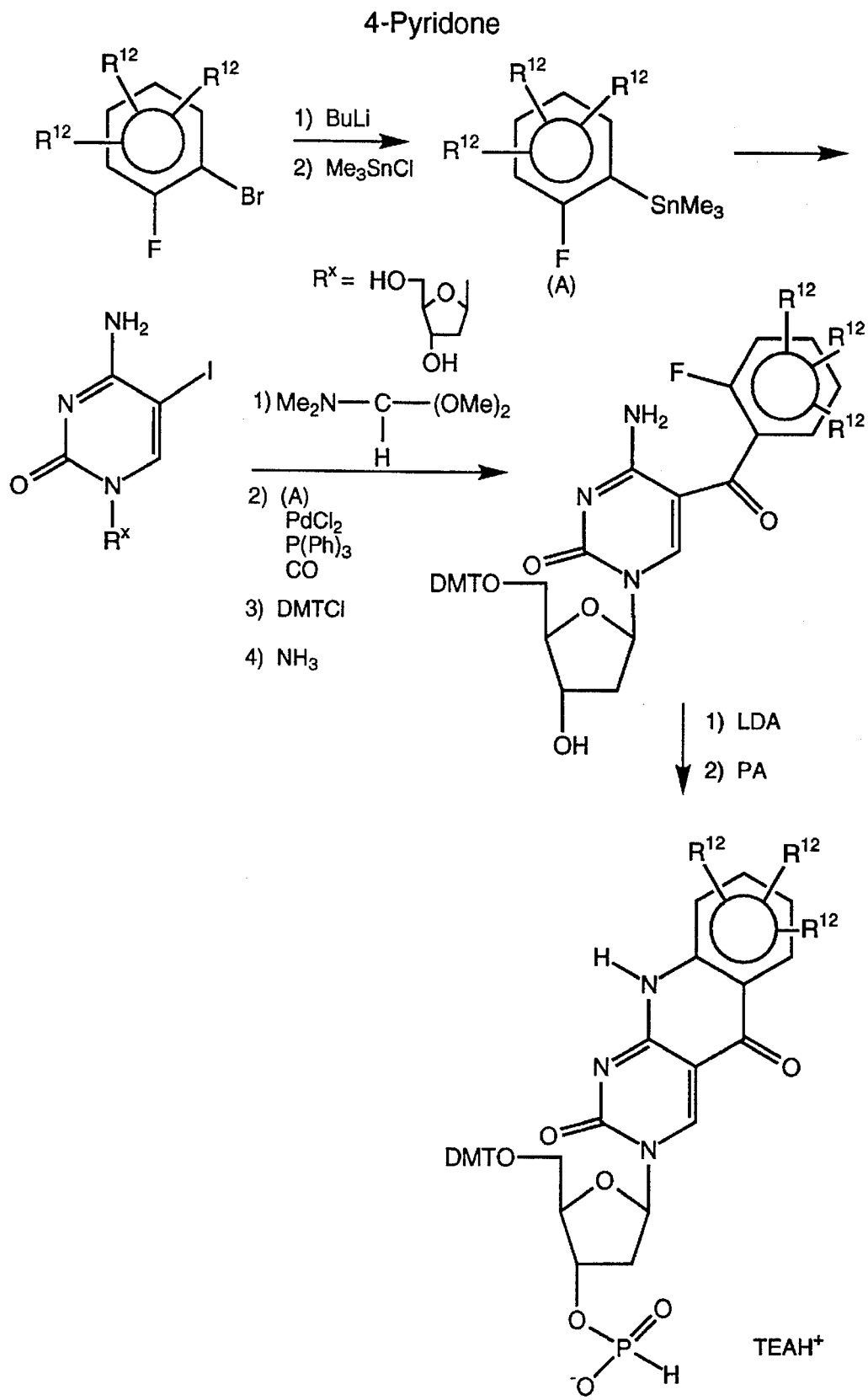
FIG. 11. shows synthesis of a 4-pyridone tricyclic cytosine nucleomonomer.
Figure 12:
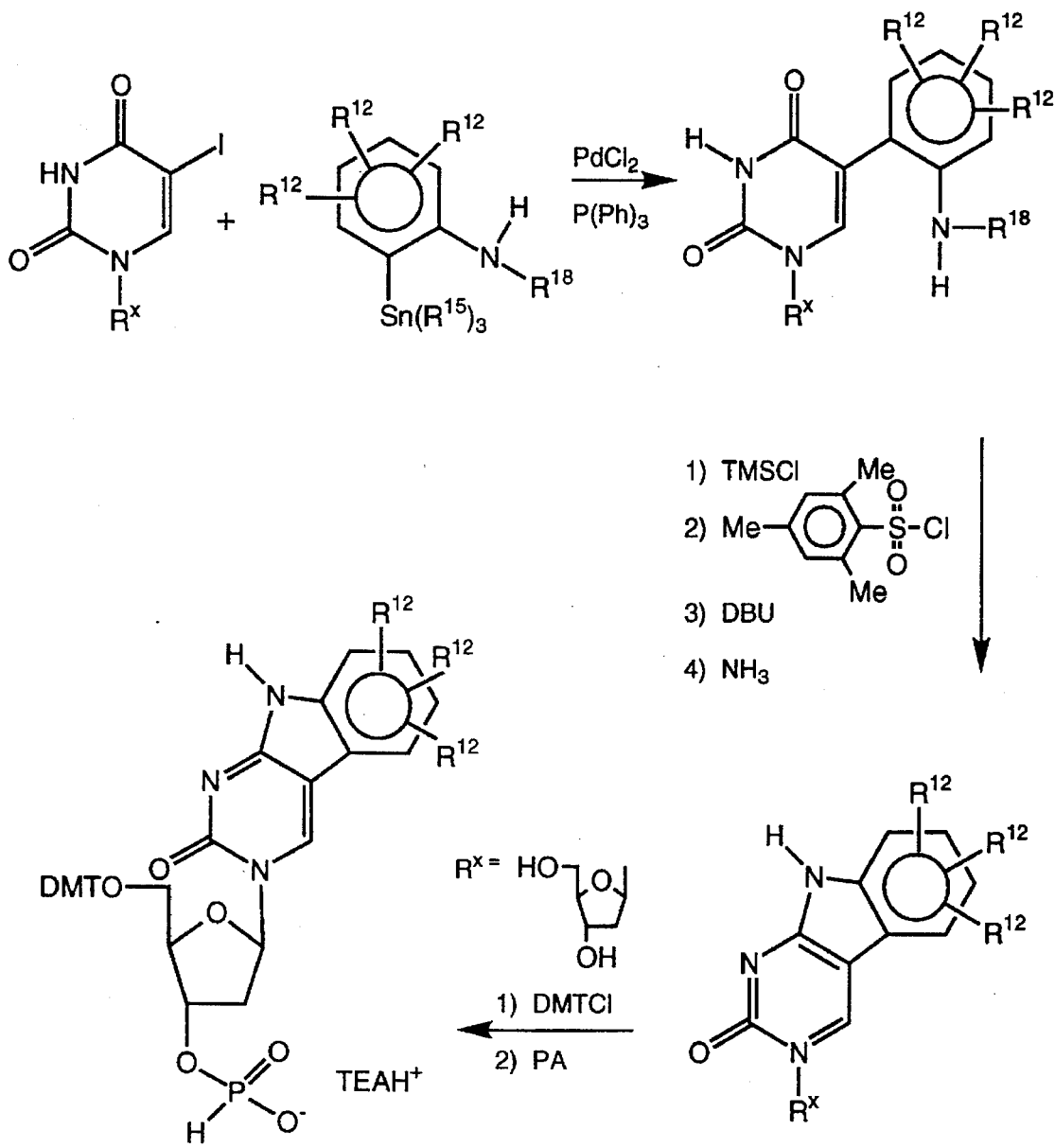
FIG. 12. shows synthesis of a phenopyrroline tricyclic cytosine nucleomonomer.
Figure 13:
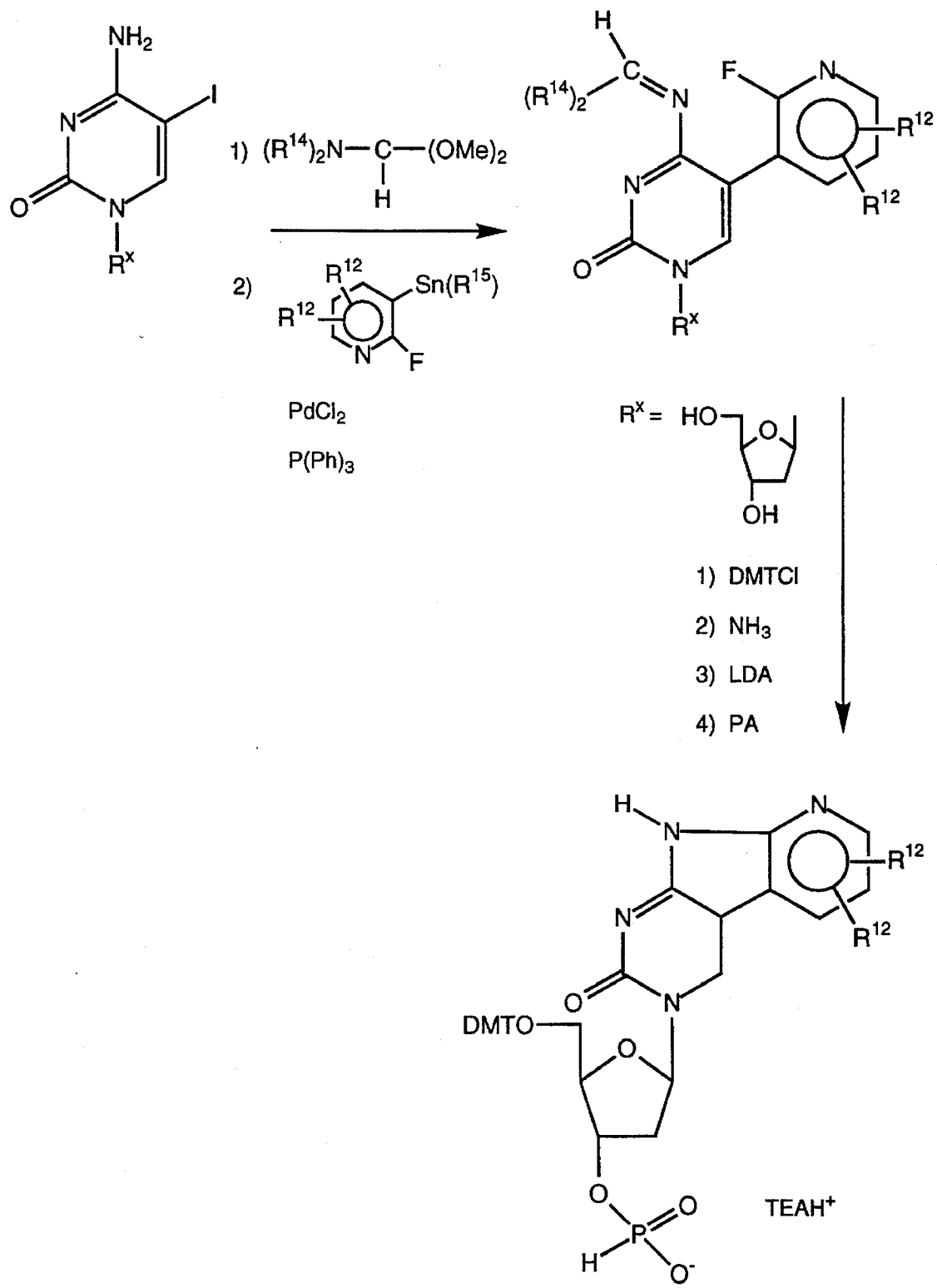
FIG. 13. shows synthesis of a pyridinopyrroline tricyclic cytosine nucleomonomer.
Figure 14:
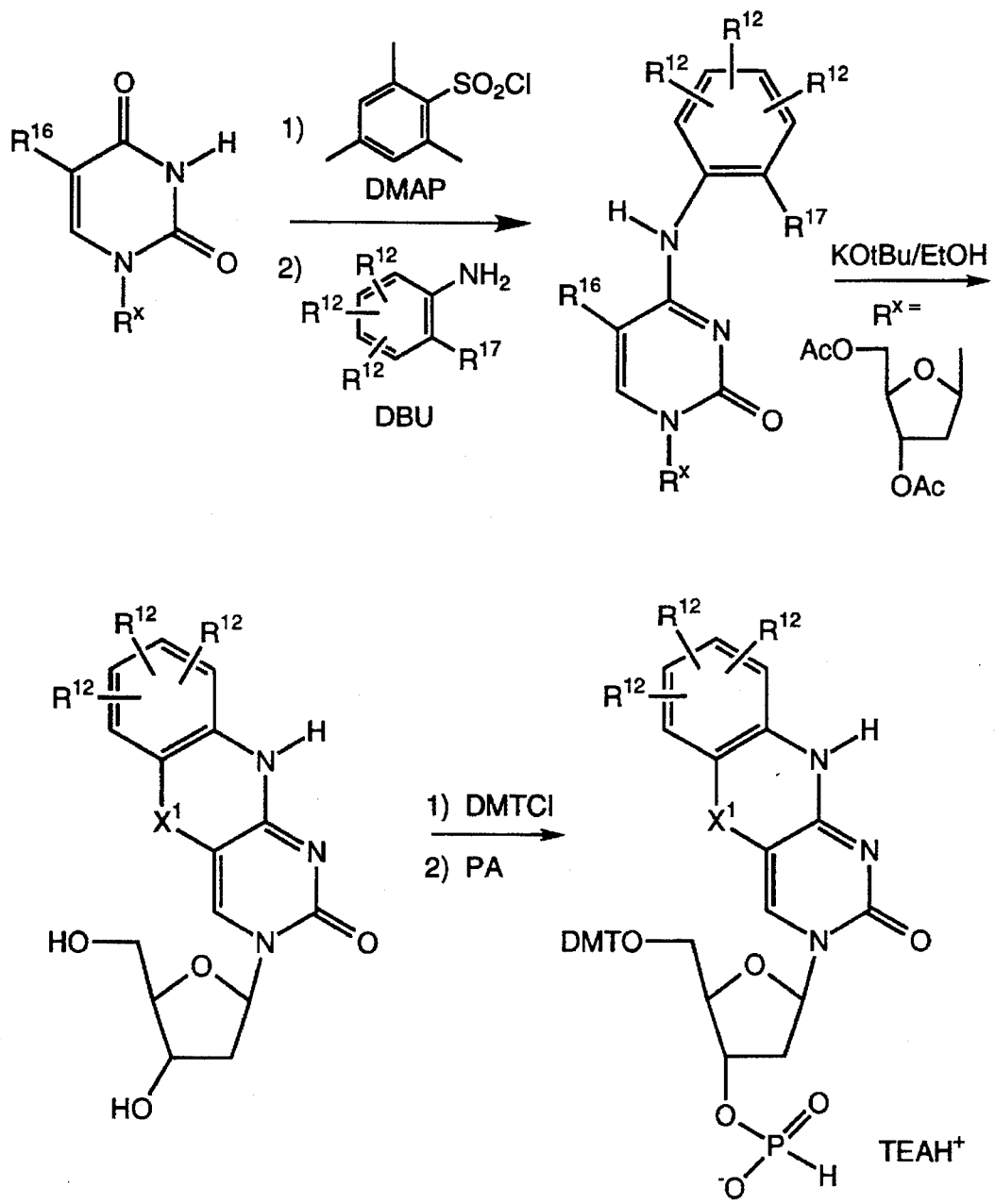
FIG. 14. shows synthesis of a phenothiazine and phenoxazine tricyclic cytosine nucleomonomer.
Figure 15:
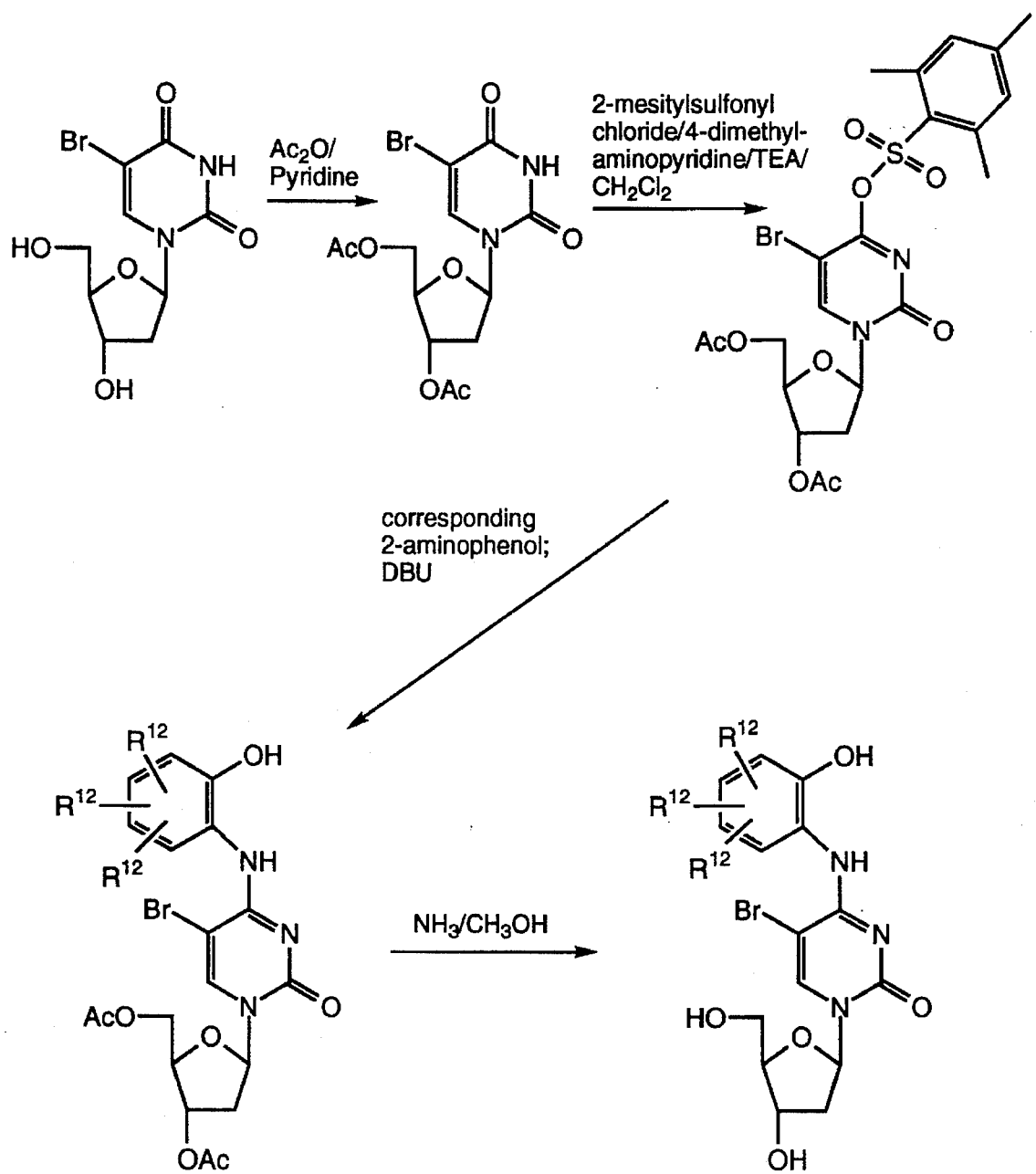
FIG. 15. shows synthesis of a phenoxazine tricyclic cytosine nucleomonomer intermediate.
Figure 16:
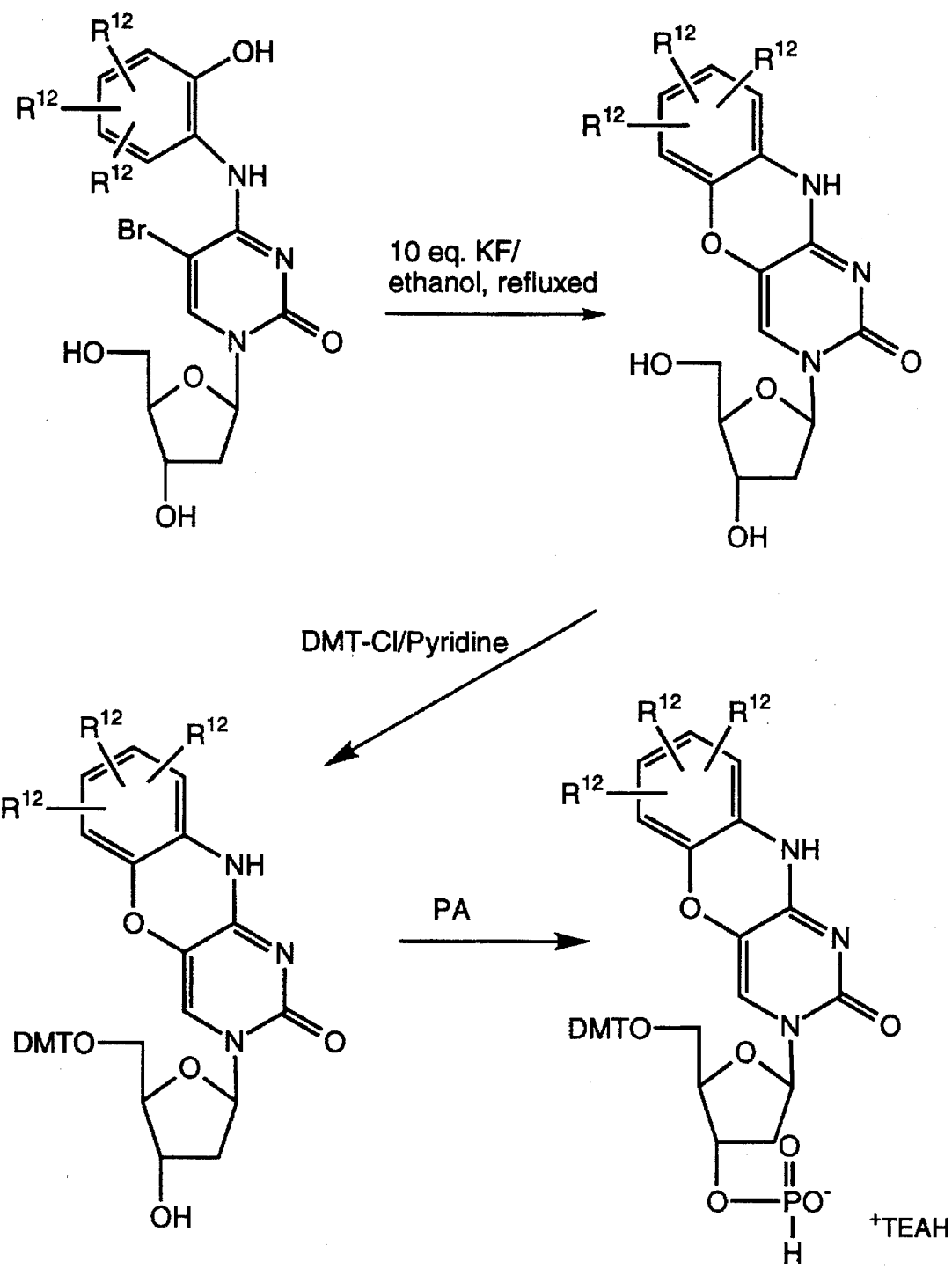
FIG. 16. shows synthesis of a phenoxazine tricyclic cytosine nucleomonomer.
Figure 17:
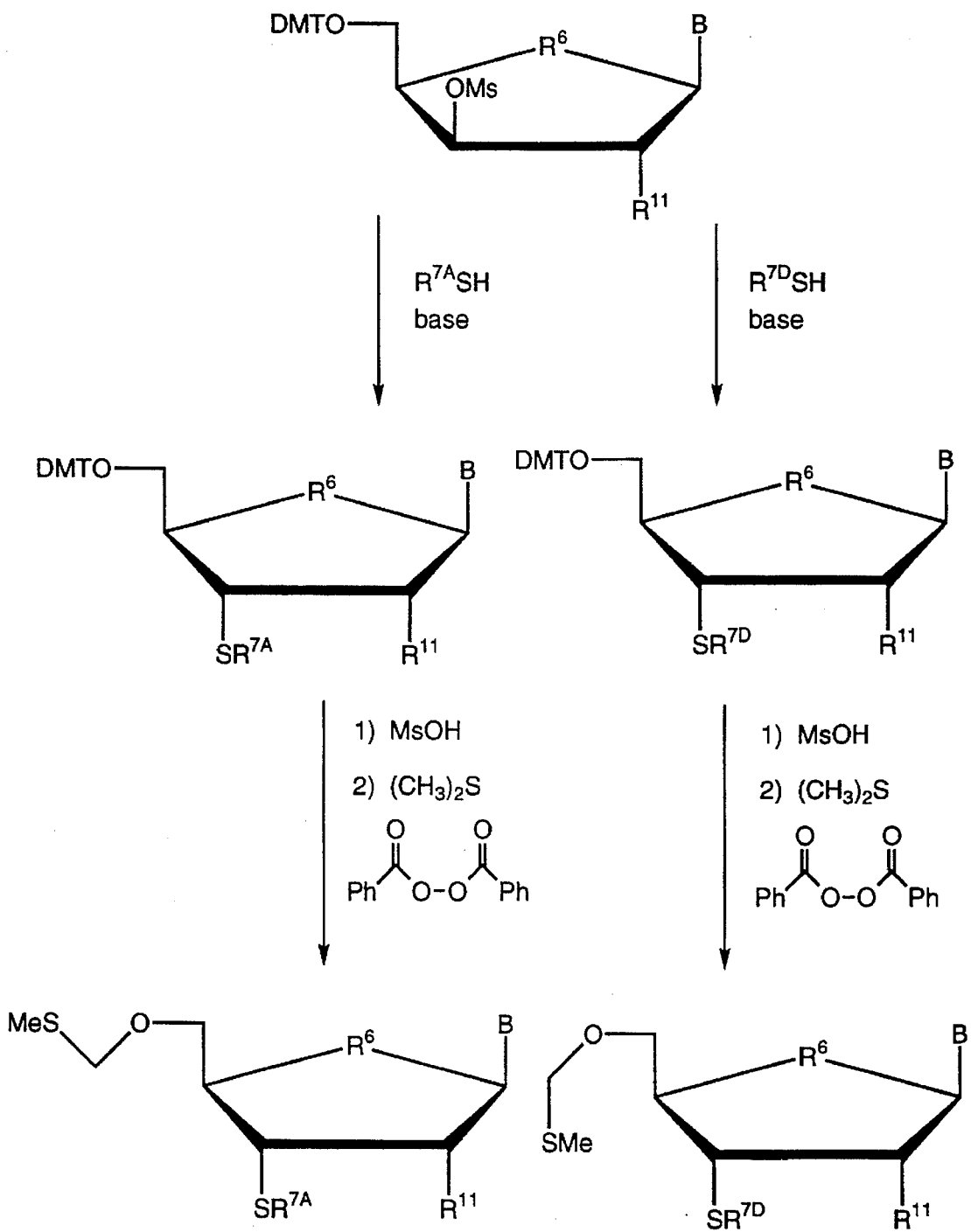
FIG. 17. shows synthesis of monomer intermediates containing $R^{7A}$ and $R^{7D}$.
Figure 18:
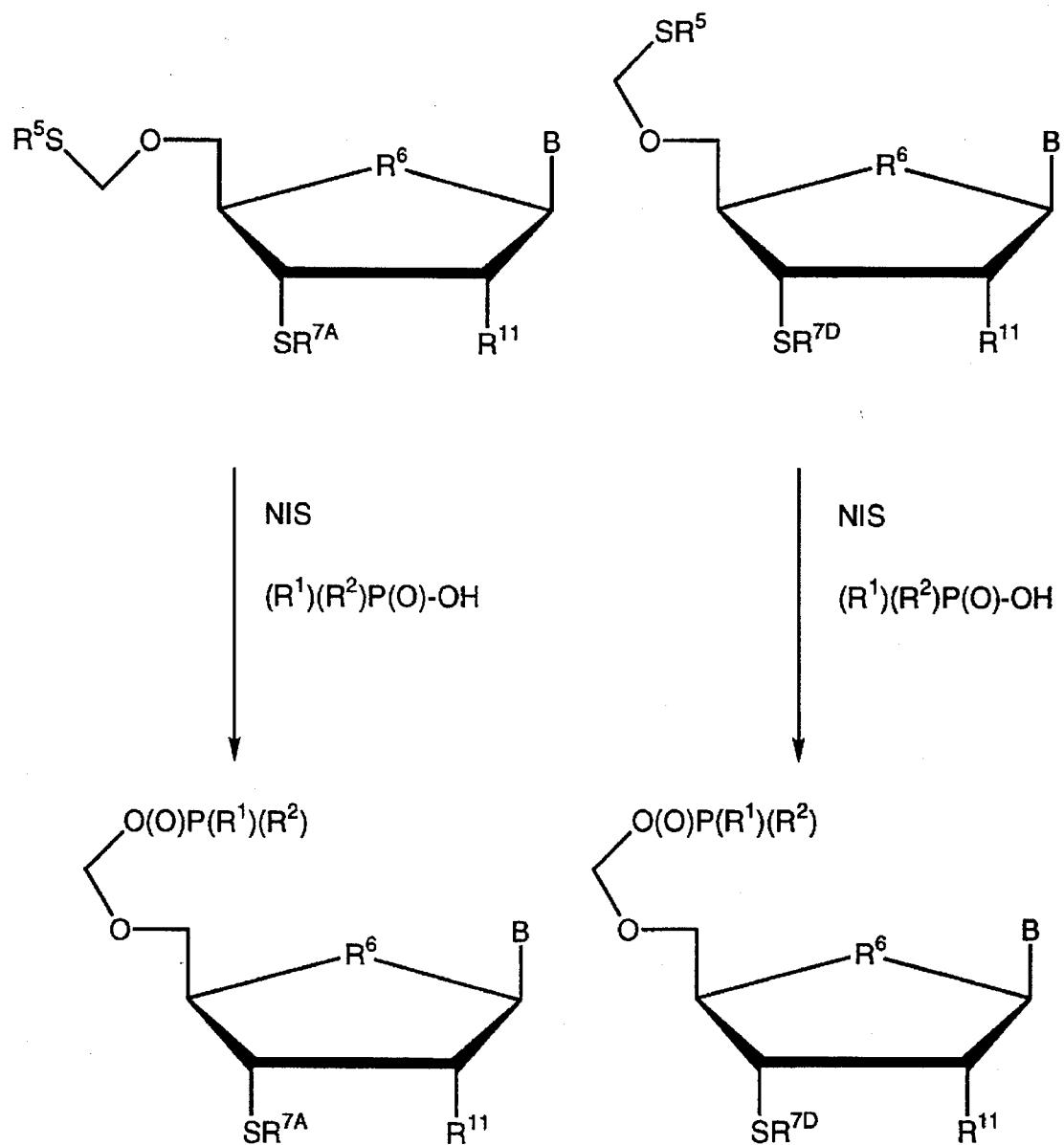
FIG. 18. shows synthesis of phosphinate-substituted monomers containing $R^{7A}$ and $R^{7D}$.
Figure 19:
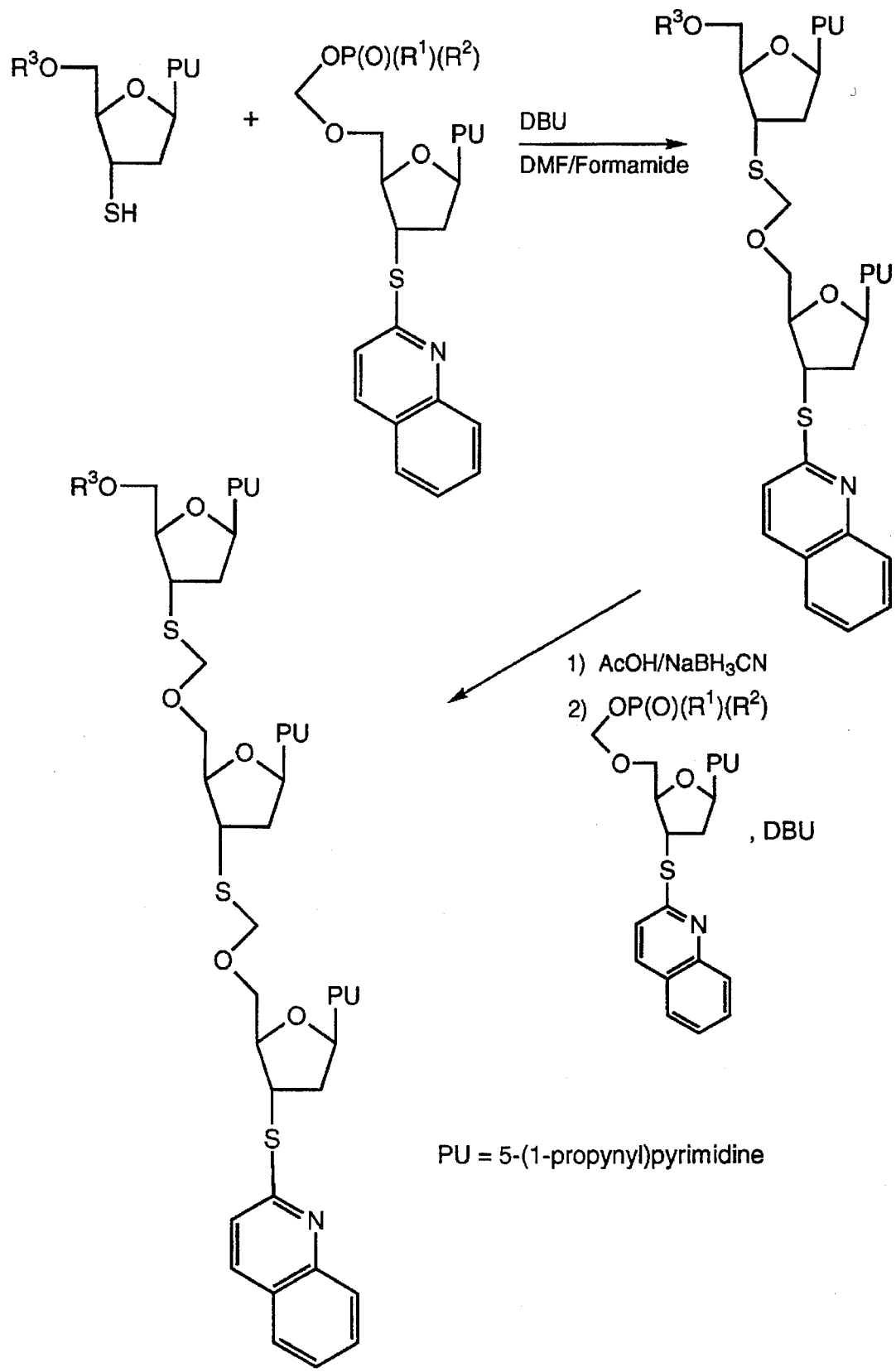
FIG. 19. Synthesis of 3',5' thioformacetal linked dimers containing 5-(1-propynyl)uracil.

The invention is directed to compounds (nucleomonomers) useful in the synthesis of oligonucleotide analogs comprising one or more acetal linkages. The compounds have the structure

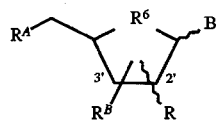

wherein

B is a purine or pyrimidine base;

R is H, O-alkyl (1–6C), O-alkenyl (1–6C) or halogen;

$R^A$ is $XR^{7A}$, $XR^{7B}$, $SR^{7D}$, $OR^3$ or $OCH_2O(O)P(R^1)(R^2)$;

$R^B$ is linked to the 2' or 3' position and is $XR^{7A}$, $XR^{7B}$, XH, $SR^{7D}$, $OR^3$ or $OCH_2O(O)P(R^1)(R^2)$, provided that either $R^A$ or $R^B$ is $OCH_2O(O)P(R^1)(R^2)$, but not both $R^A$ and $R^B$ are $OCH_2O(O)P(R^1)(R^2)$;

$R^1$ and $R^2$ are independently,
  alkyl (1–18C),
  alkyl (1–18C) substituted with 1, 2 or 3 substituents selected from the group consisting of halogen, nitro ($NO_2$), cyano (CN), O-alkyl (1–10C), O-aryl (6–10C), $COOR^8$, $COR^8$, $SO_2R^8$, $N(R^8)_2$ and CON $(R^8)_2$, wherein $R^8$ is alkyl (1–10C), aryl (6–10C) alkyl-aryl (7–12C) or heteroaryl (3–12C),
  aryl (6–10C),
  aryl (6–20C) substituted with 1, 2 or 3 groups or atoms selected from the group consisting of alkyl (1–10C), halogen, $NO_2$, CN, O-alkyl (1–10C), O-aryl (6–10C), $COOR^8$, $COR^8$, $SO_2R^8$, $N(R^8)_2$ and CON $(R^8)_2$;
  heteroaryl (3–5C),
  heteroaryl (3–5C) substituted with 1, 2 or 3 groups or atoms selected from the group consisting of alkyl (1–10C), halogen, $NO_2$, CN, O-alkyl (1–10C), O-aryl (6–10C), $COOR^8$, $COR^8$, $SO_2R^8$, $N(R^8)_2$ and $CON(R^8)_2$ or $R^1$ and $R^2$ together with the phosphorus atom to which they are attached form the structure

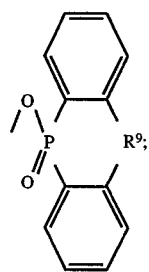

$R^3$ is a lewis acid stable protecting group;

$R^6$ is O, $CH_2$, CHF or $CF_2$;

$R^{7A}$ is an electron withdrawing sulfur protecting group;

$R^{7B}$ is a protecting group that is stable to $S^-$ anion nucleophiles;

$R^{7D}$ is a compound of structure 34–41 and 45

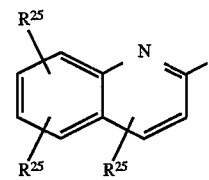
34

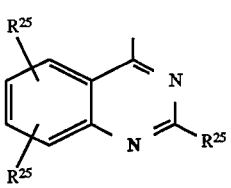
35

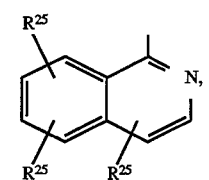
36

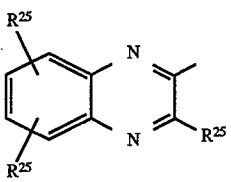
37

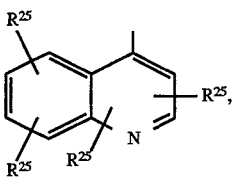
38

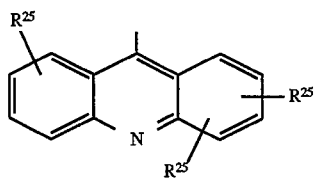
39

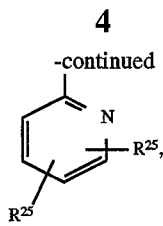
40

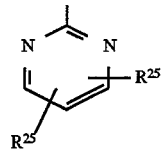
41

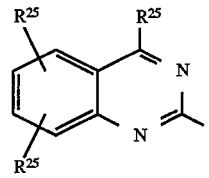
45

$R^9$ is O, $CH_2$, C(O) or $CF_2$;

$R^{25}$ is hydrogen, alkyl (1–6C), $OR^{26}$, $C(O)R^{26}$, C(O)$OR^{26}$, CN, $NO_2$, $N(CH_3)_2$, SO or $SO_2$ wherein $R^{26}$ is alkyl (1–6C) or substituted alkyl (1–6C), or two $R^{25}$ together on the same ring form a 5-membered aromatic ring comprising carbon atoms and 1 or 2 atoms or groups selected from the group consisting of S, O, N and $N(CH_3)_2$, provided that no adjacent atoms are both O, or two $R^{25}$ together on the same ring form a 6-membered aromatic ring comprising carbon atoms and 0, 1 or 2 nitrogen atoms, provided that there is no more than one $N(CH_3)_2$ group in any single protecting group; and X is oxygen (O) or sulfur (S).

Exemplary nucleomonomers include compounds of the structure 1, 2, 3, 4, 5, 6, 7, 7a, 8, 8a, 9, 10, 11g, 11h, 12b, 13b, 30, 30a, 31 and 31a

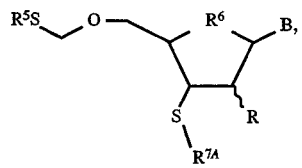
1

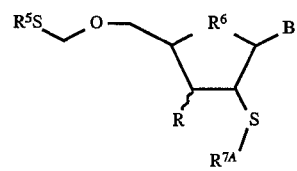
2

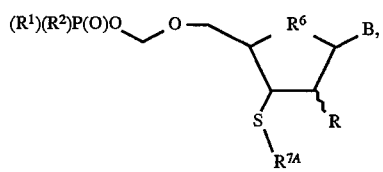
3

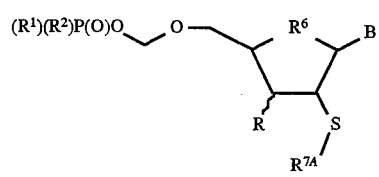
4

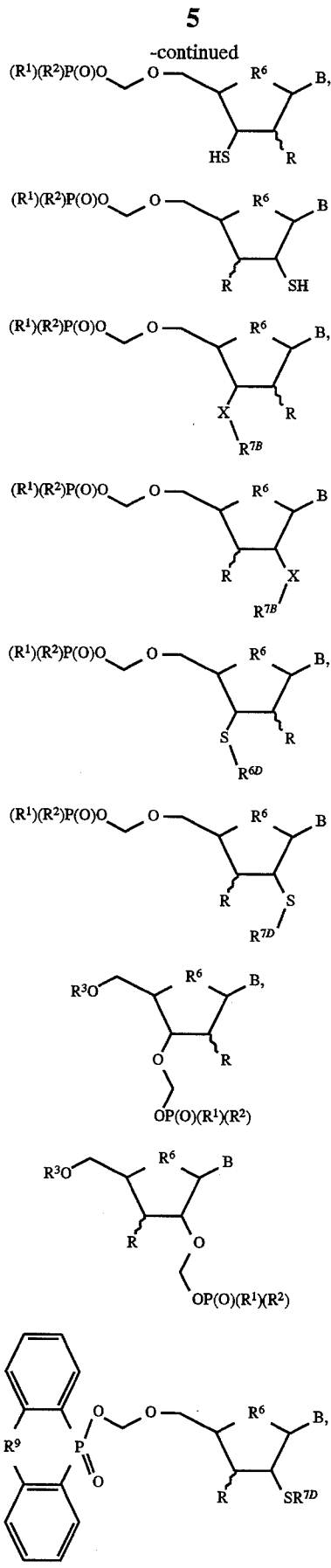
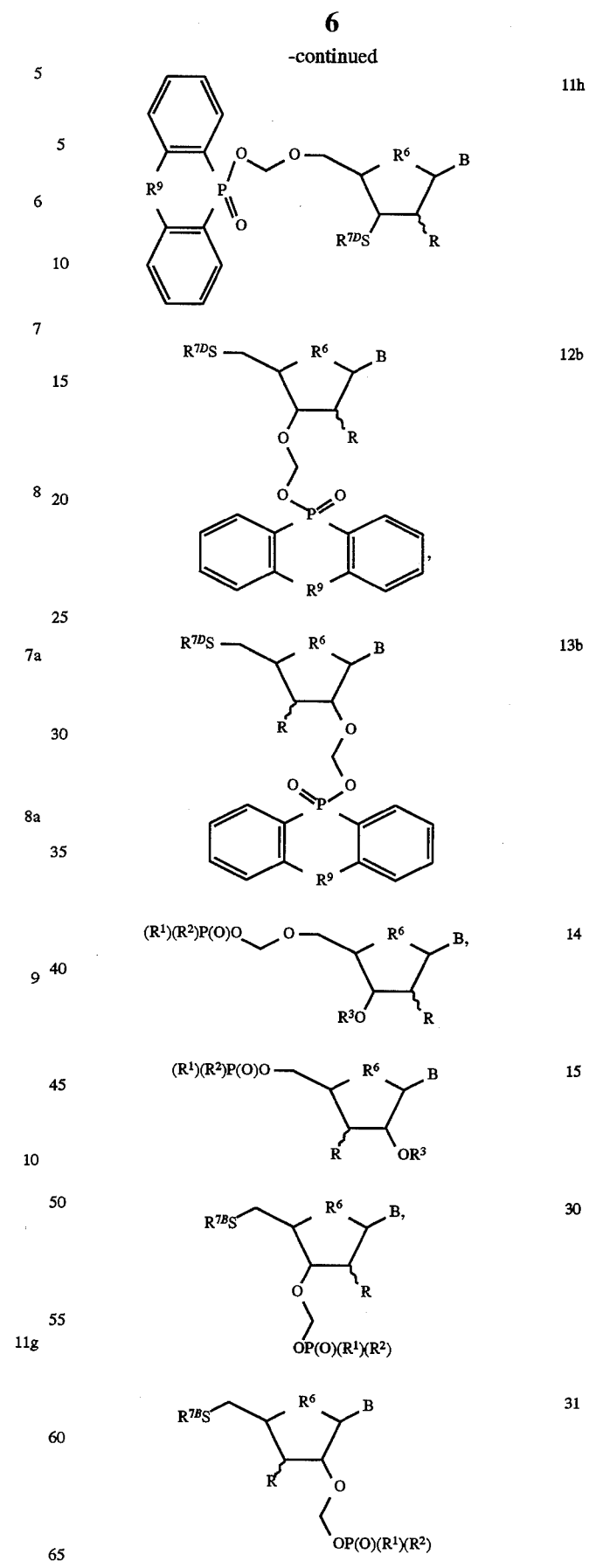

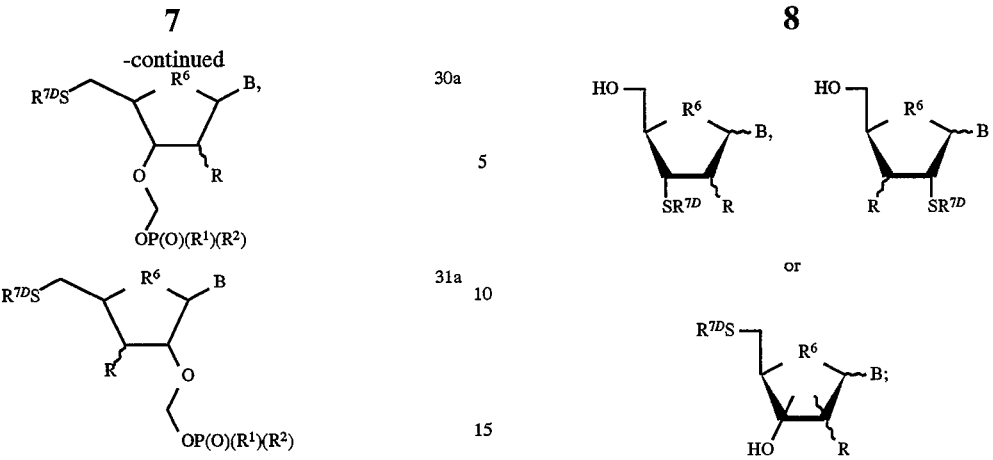

wherein

B, R, $R^1$, $R^2$, $R^3$, $R^5$, $R^6$ and $R^{7D}$ have the meanings given;

$R^{7A}$ is an electron withdrawing sulfur protecting group;

$R^{7B}$ is a protecting group that is stable to $S^-$ anion nucleophiles;

X is oxygen (O) or sulfur (S).

The nucleomonomers can be used in a method to synthesize a compound comprising the steps:

(a) providing a compound of structure

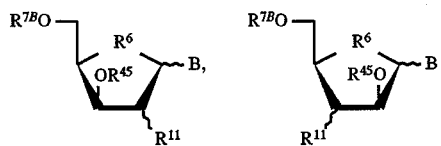

or

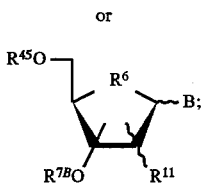

(b) reacting the compound of step (a) with a compound of structure $R^{7D}SH$ in the presence of a hindered nonnucleophilic base and solvent to obtain a second compound of structure

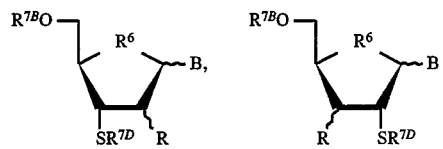

or

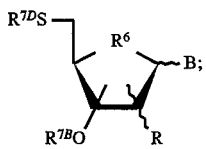

(c) optionally removing $R^{7B}$ in the presence of acid and a scavenger to obtain a third compound of the structure

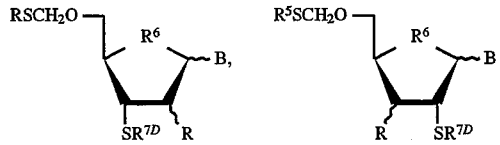

or

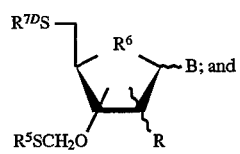

(d) optionally reacting the compound of step (c) with $R^5SR^5$, $R^5$ is alkyl (1–6C) or aryl (6–10C), and benzoyl peroxide to obtain a compound of structure

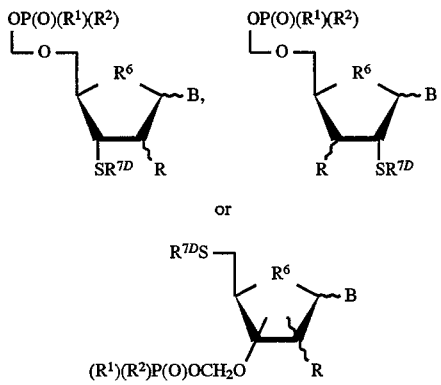

(e) optionally oxidizing the compound of step (d) with a compound of structure $(R^1)(R^2)P(O)OH$ in the presence of an oxidizing agent to obtain a compound of structure wherein B, R, $R^1$, $R^2$, $R^5$, $R^6$ and $R^{7D}$ have the meanings given and $R^{45}$ is Ms (mesylate) or TMSOTf.

In another aspect, the invention is directed to a method to synthesize a phosphinate-substituted nucleomonomer comprising the steps:

(a) providing a nucleomonomer having the structure 1 or 2

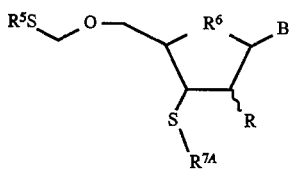

1 or

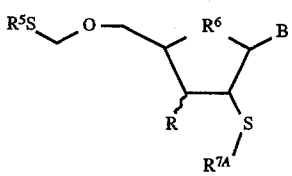

2 wherein R, $R^5$, $R^6$ and $R^{7A}$ have the meanings given;

B is a purine or pyrimidine base in the α or β anomer configuration; and (b) oxidizing the nucleomonomer of step (a) with an electrophilic halogen in the presence of a phosphinate compound having the structure $(R^1)(R^2)P(O)$—OH wherein B, $R^1$, $R^2$, $R^5$, $R^6$ and $R^{7A}$ have the meanings given, to obtain a phosphinate-substituted nucleomonomer having the structure 3 or 4

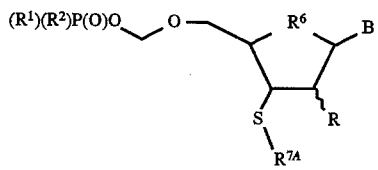

3 or

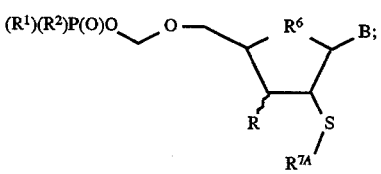

4

(c) removing the $R^{7A}$ protecting group from the nucleomonomer of step (b) by treatment with mild base such as ammonia to obtain a compound of structure 5 or 6

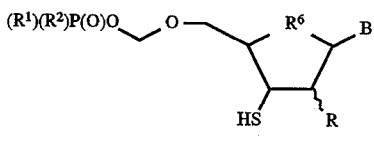

5 or

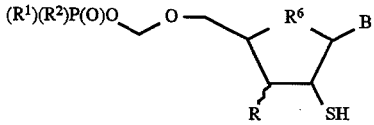

6 wherein B, R, $R^1$, $R^2$ and $R^6$ have the meanings given; and (d) protecting the compound of step (c) to obtain a phosphinate substituted nucleomonomer of structure 7 or 8

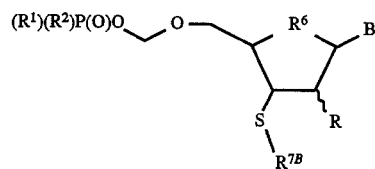

7 or

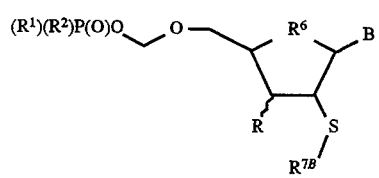

8 wherein B, R, $R^1$, $R^2$, $R^6$ and $R^{7B}$ have the meanings given.

Each step of the synthesis methods disclosed herein can be accomplished independently to obtain any intermediate compound. Thus, nucleomonomers of structure 5 or 6 are used to synthesize nucleomonomers of structure 7 or 8 by reaction with a protecting group donor (such as DMT-chloride for the DMT protecting group) in organic solvent (such as dry pyridine). A nucleomonomer of structure 7, 7a, 8, 8a, 14 or 15 is coupled to a nucleomonomer of structure 22 or 23 to synthesize dimers. Nucleomonomers of structure 3 or 4 are used to synthesize structure 5 or 6 compounds by treatment with a base (such as ammonia) in alcohol when $R^{7A}$ is acyl.

Another aspect of the invention is a method to synthesize a thioformacetal linked oligonucleotide analog comprising the steps:

(a) providing a compound of structure 22 or 23

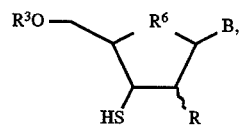

22 or

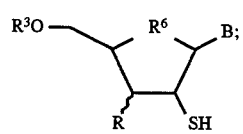

23

(b) coupling the compound of step (a) in the presence of a non-nucleophilic base in organic solvent with a compound of structure 7, 7a, 8 or 8a

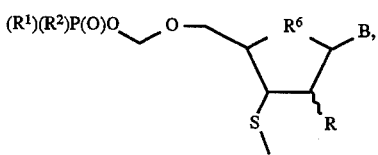

7

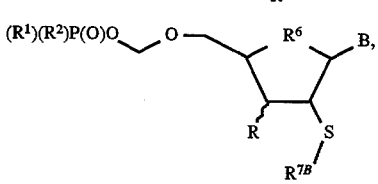

8

11

-continued

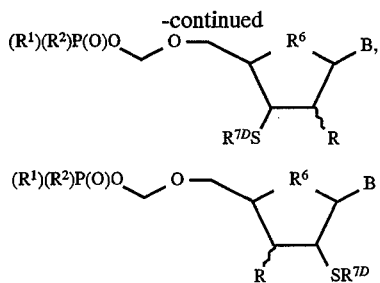 7a

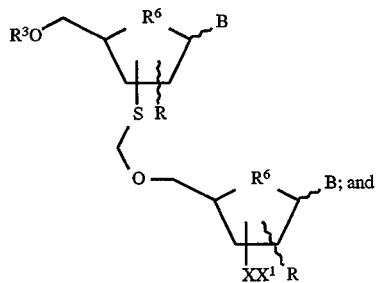 8a to obtain a thioformacetal-linked oligonucleotide analog of structure

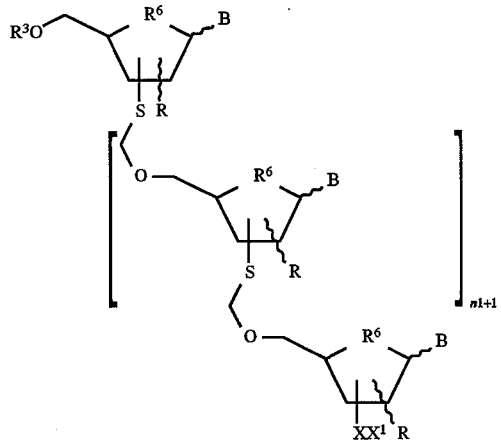

(c) optionally removing $X^1$ from the thioformacetal-linked oligonucleotide by treatment with base to obtain a deprotected oligonucleotide analog;

(d) coupling the deprotected oligonucleotide analog with a second compound of structure 7, 7a, 8 or 8a in the presence of a non-nucleophilic base in organic solvent to obtain a second thioformacetal-linked oligonucleotide analog of structure wherein n1 is 0; (e) optionally repeating steps (c) and (d) until an oligonucleotide having a desired base sequence is obtained and n1 is an integer between 1 and 46; and (f) optionally removing $X^1$ from the oligomer of step (b) or step (d) and coupling the resulting deprotected oligomer of step (b) or step (d) with a compound of structure 14 or 15 to obtain an oligomer wherein n1 between 1 and 47 and wherein B, R, $R^1$, $R^2$, $R^3$, $R^6$, $R^{7D}$, X and $X^1$ have the meanings given and wherein $R^3$ at the 5' position and $R^3$ at

12 the 2' or 3' position are the same or different. This method is used to synthesize dimers containing $R^3$ at both the 5' and the 2' or 3' positions by coupling a nucleomonomer of structure 22 or 23 with a compound of structure 14 or 15. As used herein n1 is an integer having a value between 0 and 49 inclusive.

Another aspect of the invention is a method to synthesize a formacetal linked oligonucleotide analog comprising the steps: (a) providing a compound of structure 40 or 41

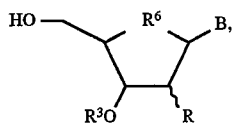 40

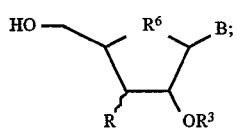 41

(b) coupling the compound of step (a) with a compound of structure 9 or 10

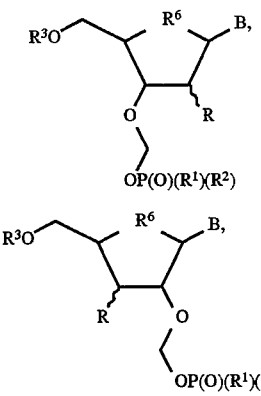

in the presence of an oxophilic lewis acid to obtain a formacetal linked oligonucleotide analog of structure

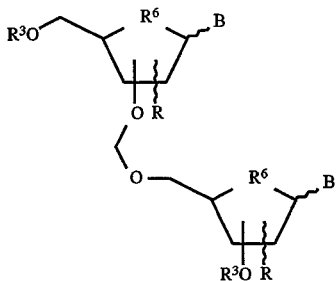

wherein both $R^3$ are not the same; (c) removing $R^3$ at the 5' position from the formacetal linked oligonucleotide analog of step (b) by treatment with base sufficient to remove $R^3$ at the 5' position without removing $R^3$ at the 2' or 3' position to obtain a 5' deprotected formacetal linked oligonucleotide analog; (d) coupling the 5' deprotected formacetal linked oligonucleotide analog of step (c) with a compound of structure 9 or 10 to obtain a formacetal linked oligonucleotide analog of structure

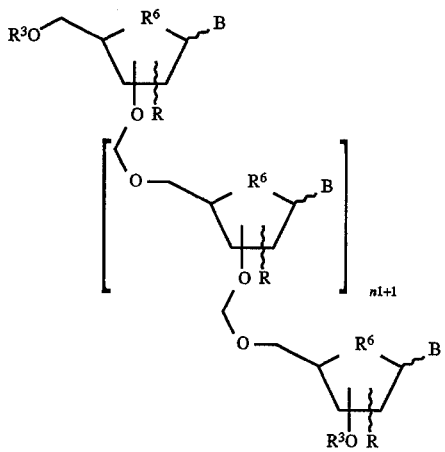

wherein n1 is 0; and (e) optionally repeating steps (c) and (d) until a formacetal linked oligonucleotide analog having a desired base sequence is obtained and n1 is an integer between 1 and 47, provided that when two $R^3$ are linked to the same molecule, they are different and $R^3$ at the 5' position can be removed without removing $R^3$ at the 2' or 3' position and B, R, $R^1$, $R^2$, $R^3$, $R^6$, and $R^{7D}$ have the meanings given. Exemplary $R^3$ include $C(O)R^4$, hindered silyl groups of the structure $Si(R^{47})(R^{48})(R^{49})$, benzyl, FMOC, pivaloyl, or phenoxyacetyl wherein $R^4$ is alkyl (1–18C), aryl (1–18C), substituted alkyl (1–18C) or C(O)-alkyl (wherein alkyl is 1–17C); $R^{47}$, $R^{48}$ and $R^{49}$ are independently methyl, ethyl, isopropyl, t-butyl or phenyl provided that at least one of $R^{47}$, $R^{48}$ and $R^{49}$ is isopropyl, t-butyl or phenyl (including species where two or three of $R^{47}$, $R^{48}$ and $R^{49}$ are isopropyl, t-butyl or phenyl).

A second method to synthesize a formacetal linked oligonucleotide analog comprises the steps: (a) providing a compound of structure 42 or 43

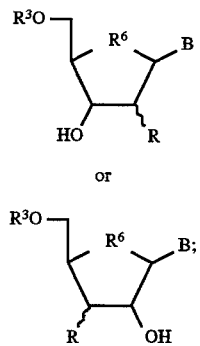

(b) coupling the compound of step (a) with a compound of structure 44 or 45

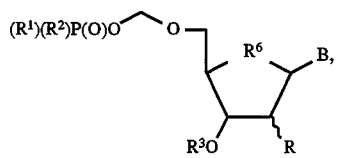

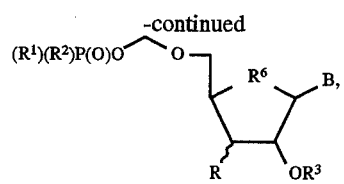

in the presence of an oxophilic lewis acid to obtain a formacetal linked oligonucleotide analog of structure

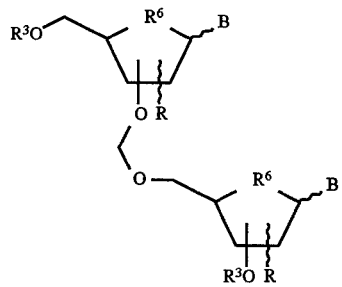

wherein $R^3$ is a lewis acid stable protecting group provided that when two $R^3$ are present on the same molecule, they are not both the same and $R^3$ at the 2' or 3' position can be selectively removed without removing $R^3$ at the 5' position; (c) removing $R^3$ at the 2' or 3' position from the formacetal linked oligonucleotide analog of step (b) by treatment with base sufficient to remove $R^3$ at the 2' or 3' position without removing $R^3$ at the 5' position to obtain a 2' or 3' deprotected formacetal linked oligonucleotide analog; (d) coupling the 2' or 3' deprotected formacetal linked oligonucleotide analog of step (c) with a compound of structure 44 or 45 to obtain a formacetal linked oligonucleotide analog of structure

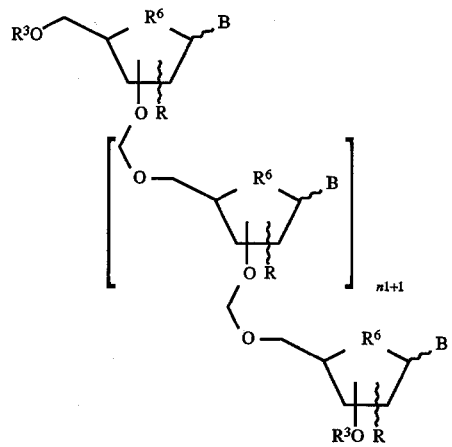

wherein n1 is 0; and (e) optionally repeating steps (c) and (d) until a formacetal linked oligonucleotide analog having a desired base sequence is obtained and n1 is an integer between 1 and 47, provided that when two $R^3$ are linked to the same molecule, $R^3$ at the 5' position can be removed without removing $R^3$ at the 2' or 3' position and B, R, $R^1$, $R^2$, $R^3$, $R^6$, and $R^{7D}$ have the meanings given. Exemplary $R^3$ include $C(O)R^4$, $Si(R^{47})(R^{48})(R^{49})$, benzyl, FMOC or phenoxyacetyl wherein $R^4$ is alkyl (1–18C), aryl (1–18C) or substituted alkyl (1–18C); $R^{47}$, $R^{48}$ and $R^{49}$ are independently methyl, ethyl, isopropyl, t-butyl or phenyl provided that at least one of $R^{47}$, $R^{48}$ and $R^{49}$ is isopropyl, t-butyl or phenyl.

Another aspect of the invention includes a method to synthesize a 5',2'- or 5',3'-thioformacetal linked oligonucleotide analog comprising:

(a) providing a compound of structure of 32 or 33

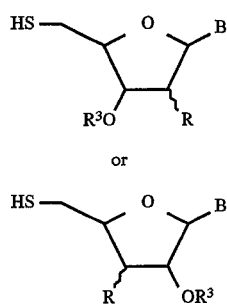

(b) coupling the compound of step (a) with a compound of structure 12, 13, 30, 30a, 31 or 31a

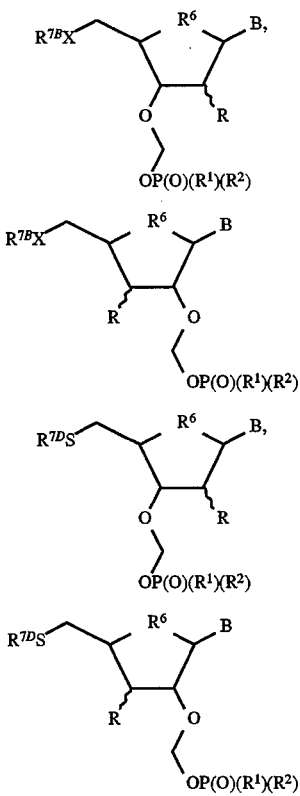

by coupling in the presence of a nonnucleophilic base and organic solvent to obtain an oligonucleotide analog of structure

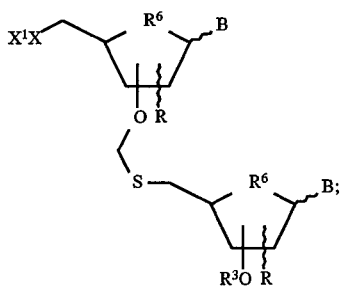

(c) removing $R^{7B}$ or $R^{7D}$ from the compound of step (b) to obtain a deprotected oligonucleotide analog; (d) coupling a compound of structure 30, 30a, 31 or 31a to obtain a 5'-thioformacetal-linked oligonucleotide analog of structure

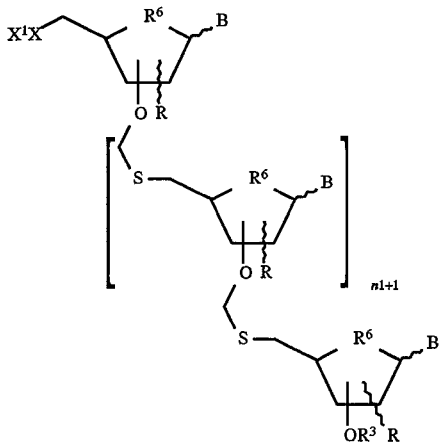

wherein n1 is 0; and (e) optionally repeating steps (c) and (d) until a 5-thioformacetal-linked oligonucleotide analog is obtained wherein n1 is an integer between 1 and 46 inclusive; and (f) optionally removing X1 from the oligomer of step (b) or step (c) and coupling the resulting deprotected oligomer with a compound of structure 9 or 10 to obtain an oligomer as shown in step (c) wherein n1 is 0–47 inclusive and $R^3$ at the 5' and at the 2' or 3' positions are the same or different and wherein B, R, $R^1$, $R^2$, $R^3$, $R^6$, $R^{7D}$, X and $X^1$ have the meanings given. A dimer is similarly synthesized by coupling a compound of structure 32 or 33 with a compound of structure 9 or 10 to obtain a 5',2'- or a 5',3'-thioformacetal linked dimer having $R^3$ at the 5' and at the 2' or 3' position wherein each $R^3$ is the same or is different.

The $R^{7D}$ group has not previously been used to protect thiol groups. An aspect of the invention is a method to protect a thiol group comprising: reacting a molecule having a free thiol group with a compound having the structure $R^{7D}$-halogen in the presence of a hindered base at 20°–100° C. (including ranges of 20°–30°, 20°–50° and 20°–70° C.) in organic or aqueous solvent to obtain a compound having the structure, —S—$R^{7D}$, wherein $R^{7D}$ has the meaning given and halogen is Cl, Br, F, or I. Suitable molecules containing a free thiol group include a protein comprising 20 or more amino acid residues and having one or more free thiol groups, a peptide comprising 2 to 20 amino acid residues and having one or more free thiol groups, an amino acid having a free thiol group, alkyl-SH (1–18C), aryl-SH (6–18C), heteroaryl-SH (3–18C), substituted alkyl-SH (1–18C), substituted aryl-SH (6–18C) or substituted heteroaryl-SH (3–18C). Suitable amino acids include cysteine, homocystine, 2-thiolhistidine or cystathionine.

Oligomers include those where n1 is an integer from 0–47 inclusive (including ranges of 0–5, 0–10, 0–15, 0–20 and 0–30 and including species where n1 is 0, 1, 2, 3, 4, 5, 6, 7, 8, 9, 10, 11, 12, 13, 14, 15, 16, 17, 18, 19 or 20).

DETAILED DESCRIPTION OF THE INVENTION

Definitions.

As used herein, oligonucleotide means single stranded unmodified DNA or RNA comprising (a) the purine or pyrimidine bases guanine, adenine, cytosine, thymine and/or uracil; (b) ribose or deoxyribose; and (c) a phosphodiester group that linkage adjacent nucleoside moieties. An oligonucleotide comprises 2 or more linked nucleomonomers. Any 2',5' linkages in oligonucleotide analogs will generally not contain phosphorus (i.e., excludes linkages such as thioate, phosphodiester and the like).

Oligonucleotide analog means an oligonucleotide comprising one or more covalent modifications such as alkylation or alkynylation at, for example, the 5 position of pyrimidines that results in a pyrimidine base other than uracil, thymine or cytosine, i.e., 5-methylcytosine, 5-(1-propynyl)uracil and the like. Covalent modifications that result in oligonucleotide analogs include (a) substitution of an oxygen atom in the phosphodiester linkage of an oligonucleotide with a sulfur atom, a methyl group or the like and (b) replacement of the phosphodiester group with a non-phosphorus moiety such as —O—CH$_2$—O— or —S—CH$_2$—O—. Oligonucleotide analogs include covalent modification or isomers of ribose or deoxyribose such as a morpholino ring, arabinose, 2'-fluororibose or 2'-O-allylribose. Oligonucleotide analogs and methods to synthesize them have been extensively described (for example see: PCT/US90/03138, PCT/US90/06128, PCT/US90/06090, PCT/US90/06110, PCT/US92/03385, PCT/US91/08811, PCT/US91/03680, PCT/US91/06855, PCT/US91/01141, PCT/US92/10115, PCT/US92/10793, PCT/US93/05110, PCT/US93/05202, PCT/US92/04294, WO86/05518, WO89/12060, WO91/08213, WO90/15065, WO91/15500, WO92/02258, WO92/20702, WO92/20822, WO92/20823, U.S. application Ser. Nos. 07/864,873, 08/123,505 and 08/050,698, U.S. Pat. No. 5,214,136 and Uhlmann *Chem Rev* (1990) 90:543). An oligonucleotide analog comprises 2 or more linked nucleomonomers. Typical oligonucleotide analogs comprise size ranges such as 2-10, 2-15, 2-20, 2-25, 2-30, 2-50 or 2-100 linked nucleomonomers. Oligonucleotide analogs are usually linear and, when regions of inverted polarity are present, comprise no more than 1 polarity inversion per 10 nucleomonomers. Oligonucleotide analogs can be circular, branched or contain a region(s) of self-complementarity.

Nucleomonomer means a moiety comprising a purine or pyrimidine base covalently attached to a second moiety such as ribose, deoxyribose or other structure suitable for oligonucleotide analogs that bind to complementary nucleic acid sequences in a sequence-specific manner. Nucleomonomers include nucleosides, nucleoside analogs, nucleotides and nucleotide analogs. Nucleomonomers and methods to synthesize them have been extensively described (for example, see the references cited above).

Purine or pyrimidine base means a heterocyclic moiety suitable for oligonucleotides and oligonucleotide analogs and can be in the α or β anomer configuration. Purine or pyrimidine bases are moieties that bind to complementary nucleic acid sequences by Watson-Crick or Hoogsteen base pair rules. Purine or pyrimidine bases usually pair with a complementary purine or pyrimidine base via 1, 2 or 3 hydrogen bonds. The radicals of such purine or pyrimidine bases, designated herein as "B", are generally the purine, pyrimidine or related heterocycles shown in formulas 24-27.

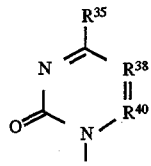

24

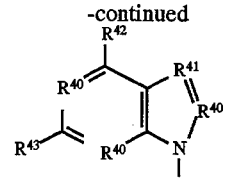

25

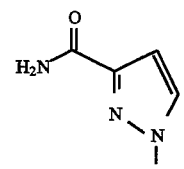

26

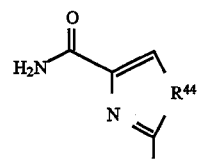

27 wherein $R^{35}$ is H, OH, OR$^{36}$, SH, SR$^{36}$, NH$_2$, or NHR$^{37}$;

$R^{36}$ is C$_1$-C$_6$ alkyl (including CH$_3$, CH$_2$CH$_3$ and C$_3$H$_7$), CH$_2$CCH (2-propynyl) and CH$_2$CHCH$_2$;

$R^{37}$ is C$_1$-C$_6$ alkyl including CH$_3$, CH$_2$CH$_3$, CH$_2$CCH, CH$_2$CHCH$_2$, C$_3$H$_7$ or a protecting group;

$R^{38}$ is N, CF, CCl, CBr, CI, CR$^{39}$ or CSR$^{39}$, COR$^{39}$;

$R^{39}$ is H, C$_1$-C$_9$ alkyl, C$_2$-C$_9$ alkenyl, C$_2$-C$_9$ alkynyl or C$_7$-C$_9$ aryl-alkyl unsubstituted or substituted by OH, O, N, F, Cl, Br or I including CH$_3$, CH$_2$CH$_3$, CHCH$_2$, CHCHBr, CH$_2$CH$_2$Cl, CH$_2$CH$_2$F, CH$_2$CCH, CH$_2$CHCH$_2$, C$_3$H$_7$, CH$_2$OH, CH$_2$OCH$_3$, CH$_2$OC$_2$H$_5$, CH$_2$OCCH, CH$_2$OCH$_2$CHCH$_2$, CH$_2$C$_3$H$_7$, CH$_2$CH$_2$OH, CH$_2$CH$_2$OCH$_3$, CH$_2$CH$_2$OC$_2$H$_5$, CH$_2$CH$_2$OCCH, CH$_2$CH$_2$OCH$_2$CHCH$_2$, CH$_2$CH$_2$OC$_3$H$_7$;

$R^{40}$ is N, CH, CBr, CCl, CI, C(CH$_3$), C(C≡CH) or C(CC≡CH);

$R^{41}$ is N, CH, CBr, CCH$_3$, CCN, CCF$_3$, C(C≡CH), C(CC≡CH) or CC(O)NH$_2$;

$R^{42}$ is H, OH, NH$_2$, SH, SCH$_3$, SCH$_2$CH$_3$, SCH$_2$CCH, SCH$_2$CHCH$_2$, SC$_3$H$_7$, NH(CH$_3$), N(CH$_3$)$_2$, NH(CH$_2$CH$_3$), N(CH$_2$CH$_3$)$_2$, NH(CH$_2$CCH), NH(CH$_2$CHCH$_2$), NH(C$_3$H$_7$), or NHR$^{37}$ wherein R$^{37}$ is a protecting group;

$R^{43}$ is H, OH, F, Cl, Br, I, SCH$_3$, SCH$_2$CH$_3$, SCH$_2$CCH, SCH$_2$CHCH$_2$, SC$_3$H$_7$, OR$^{16}$, NH$_2$, or NHR$^{37}$; and $R^{44}$ is O, S or Se.

B includes both protected and unprotected forms of the purine and pyrimidine bases. Protecting groups and their use with exocyclic amines and other groups are known (T. W. Greene and P. G. M. Wuts, *Protective Groups in Organic Synthesis*, (1991) Wiley, New York, 2nd edition) and include N-benzoyl, isobutyryl, diisobutyrylformamidinyl, 4,4'-dimethoxytrityl (DMT) and the like. Synthesis of oligomers containing B with an exocyclic amine may use standard groups including benzoyl, isobutyryl or diisobutyrylformamidinyl.

When formacetal linkages are synthesized by the methods of the invention, exocyclic amine groups on pyrimidines such as cytosine and purines will generally be protected. When thioformacetal linkages are synthesized by the methods of the invention, exocyclic amine groups on cytosine and purines will generally not be protected. Nucleomonomers containing inosine can be conveniently synthesized by converting an adenine nucleomonomer via deamination to inosine by known methods such as treatment with sodium nitrite and acetic acid. Inosine nucleomonomers are most conveniently generated prior to incorporation of sulfur into the molecule, although this may be accomplished after sulfur is introduced into the molecule.

Exemplary B include adenine, cytosine, guanine, hypoxanthine, inosine, thymine, uracil, xanthine, 2-aminopurine, 2,6-diaminopurine, 8-aza derivatives of adenine, guanine, 2-aminopurine, 2,6-diaminopurine, hypoxanthine, inosine and xanthine; 7-deaza-8-aza derivatives of adenine, guanine, 2-aminopurine, 2,6-diaminopurine, hypoxanthine, inosine and xanthine; 1-deaza derivatives of adenine, guanine, 2-aminopurine, 2,6-diaminopurine, hypoxanthine, inosine and xanthine; 7-deaza derivatives of adenine, guanine, 2-aminopurine, 2,6-diaminopurine, hypoxanthine, inosine and xanthine; 3-deaza derivatives of adenine, guanine, 2-aminopurine, 2,6-diaminopurine, hypoxanthine, inosine and xanthine; 6-azacytosine, 5-fluorocytosine, 5-chlorocytosine, 5-iodocytosine, 5-bromocytosine, 5-methylcytosine, 5-bromovinyluracil, 5-fluorouracil, 5-chlorouracil, 5-iodouracil, 5-bromouracil, 5-trifluoromethyluracil, 5-ethynyluracil, 5-propynyluracil, 6-azacytosine, 6-azathymidine and 5-trifluoromethyluracil, phenothiazine tricyclic cytidine, phenoxazine tricyclic cytidine, benzene tricyclic cytidine, 2-pyridine tricyclic cytidine and the like. Some of the base analogs and their use in oligomers have been described (see for example, U.S. application Ser. No. 08/123,505; US92/10115; US91/08811; US92/09195; WO 92/02258; Nikiforov, T. T., et al, *Tet Lett* (1992) 33:2379–2382; Clivio, P., et al, *Tet Lett* (1992) 33:65–68; Nikiforov, T. T., et al, *Tet Lett* (1991) 32:2505–2508; Xu, Y.-Z., et al, *Tet Lett* (1991) 32:2817–2820; Clivio, P., et al, *Tet Lett* (1992) 33:69–72; Connolly, B. A., et al, *Nucl Acids Res* (1989) 17:4957–4974). Bases also include protected species such as $N^4$-benzoylcytosine, $N^6$-benzoyladenine, $N^6$-diisobutyrylformamidinyladenine, $N^2$-isobutyrylguanine, $N^4$-diisobutyrylformamidinyl-5-(1-propynyl)cytosine, $N^4$-diisobutyrylformamidinyl-5-(1-propynyl)-6-azacytosine and the like.

Typical B include adenine, 1-deazaadenine, 3-deazaadenine, 7-deazaadenine, 7-deaza-7-bromoadenine, guanine, inosine, 7-deazaguanine, 7-deaza-7-bromoguanine, cytosine, 5-fluorocytosine, 5-methylcytosine, 5-(1-propynyl)cytosine, thymine, 5-(1-propynyl)uracil and 5-(1-butynyl)uracil. Bases also include the pyrimidine derivatives described in U.S. Ser. No. 08/123,505, incorporated herein by reference, of the formula 50:

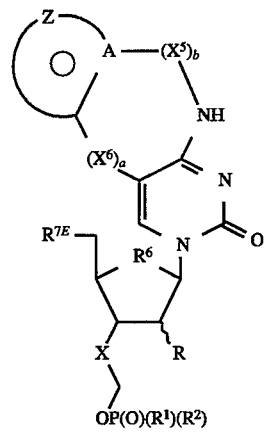

wherein

R, $R^1$, $R^2$, X and $R^6$ are as defined above and $R^{7E}$ is $SR^7$, $R^{7D}$ or $OR^3$;

a and b are 0 or 1, provided that the total of a and b is 0 or 1;

A is N or C;

$X^6$ is S, O, —C(O)—, NH or $NCH_2R^{12}$;

$X^5$ is —C(O)—;

Z is taken together with A to form an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, 2 N ring heteroatoms separated by a carbon atom, or 3 N ring heteroatoms at least two of which are separated by a carbon atom, and wherein the aryl or heteroaryl ring carbon atoms are unsubstituted with other than H or at least 1 nonbridging ring carbon atom is substituted with $R^{12}$ or =O;

$R^{13}$ is a protecting group or H;

$R^{12}$ is independently H, $C_1$-$C_6$ alkyl, $C_2$-$C_6$ alkenyl, $C_2$-$C_6$ alkynyl, $NO_2$, $N(R^{13})_2$, C≡N or halo, or an $R^{12}$ is taken together with an adjacent $R^{12}$ to complete a ring containing 5 or 6 ring atoms, and tautomers, solvates and salts thereof. The compounds of structure 50 are made through several intermediates as described.

The 4-pyridones are obtained from an intermediate having structure 51

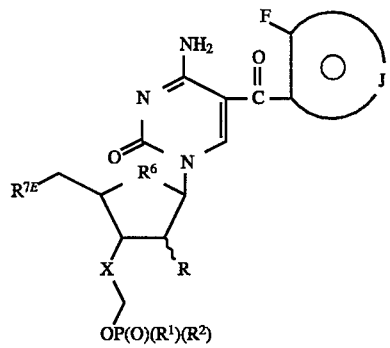

wherein R, $R^1$, $R^2$, X, $R^6$, and $R^{7E}$ are as defined above;

J is an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, or 2 N ring heteroatoms separated by a carbon atom, and wherein the aryl or heteroaryl ring carbon atoms are unsubstituted with other than H or at least 1 nonbridging ring carbon atom is substituted with $R^{12}$; and $R^{12}$ is defined above; and tautomers, salts and solvates thereof.

The 2-pyridones are synthesized from the intermediates of structures 52 and 53:

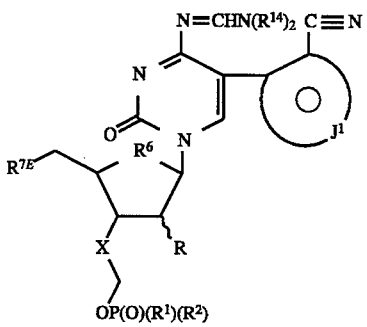

wherein

R, $R^1$, $R^2$, X, $R^6$ and $R^{7E}$ are as defined above;

$R^{14}$ is $C_1$–$C_3$ alkyl; and $J^1$ is an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, or 2 N ring heteroatoms separated by a carbon atom, and wherein the aryl or heteroaryl ring carbon atoms are unsubstituted with other than H or at least 1 nonbridging ring carbon atom is substituted with $C_1$–$C_6$ alkyl, $C_2$–$C_6$ alkenyl, $C_2$–$C_6$ alkynyl, $NO_2$, $N(R^{13})_2$, or halo;

$R^{13}$ is a protecting group or H;

and tautomers, solvates and salts thereof.

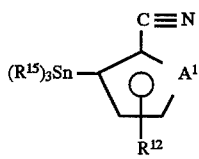

wherein $A^1$ is independently S, O, N or $CR^{12}$;

$R^{12}$ is defined above; and $R^{15}$ is $C_1$–$C_4$ alkyl; and tautomers, salts and solvates thereof.

Phenoxazines and oxadiazines also are made from the intermediate 54, as are pyridinopyrrolines, thiazines and oxazines.

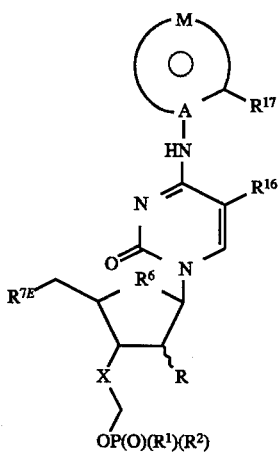

wherein

R, $R^1$, $R^2$, $R^6$, $R^{7E}$, A and X are as defined above;

$R^{16}$ is independently halo or $C_1$–$C_2$ haloalkyl;

$R^{17}$ is independently —SH, —OH, =S or =O;

A is independently N or C; and

M, taken together with the radical —A—C(—$R^{17}$), completes an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, 2 N ring heteroatoms separated by a carbon atom, or 3 N ring heteroatoms at least two of which are separated by a carbon atom, and wherein the aryl or heteroaryl ring carbon atoms are unsubstituted with other than H or at least 1 nonbridging ring carbon atom is substituted with $R^{12}$; and $R^{12}$ is defined above, and tautomers, solvates and salts thereof.

The phenopyrrolines are made by the use of the intermediate of structure 55

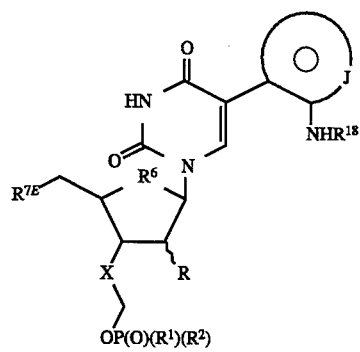

wherein

R, $R^1$, $R^2$, $R^6$, $R^{7E}$ and X are as described above;

J is an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, or 2 N ring heteroatoms separated by a carbon atom, and wherein the aryl or heteroaryl ring carbon atoms are unsubstituted with other than H or at least 1 nonbridging ring carbon atom is substituted with $R^{12}$;

$R^{12}$ is defined above; $R^{18}$ is a protecting group; and tautomers, salts and solvates thereof.

Synthesis of representative tricyclic compounds is shown in FIGS. 8 to 16. Oligomers having tricyclic pyrimidine bases that are capable of forming high melting duplexes with complementary sequences are useful in numerous processes, including antisense or codeblocking utilities in vivo or in vitro as well as useful for diagnostic, probe, or primer applications. High melting duplexes are those having melting temperatures substantially above the melting temperatures of oligonucleotide or nucleic acid duplexes of the same sequence that contain the ordinary, naturally occurring bases, e.g., adenosine, cytidine, uridine, guanosine, thymidine and the like. "Substantially above" means that the derivative oligonucleotide, when hybridized with its complementary sequence, will not dissociate from the duplex until the temperature is raised from about 2° to 40° C., ordinarily about 8° to 40° C., above the dissociation temperature of the same oligonucleotide having the analogous normal A, C, U, G or T bases, but to no greater temperature than about 95° C. This is known as the ΔTm.

Ordinarily, ΔTm is measured by comparing control oligonucleotide binding to complementary RNA with the binding of test oligonucleotide to the same RNA, following the method described in Jones et al, *J Org Chem* (1993) 58:2983.

Nucleomonomers comprising the formula IX bases, phenothiazine deoxyriboside and phenoxazine deoxyriboside have excitation and emission wavelengths of Ex380 nM/EM492 nM and Ex360 nM/EM450 nM, respectively, and are intensely fluorescent. The compounds remain fluorescent upon incorporation into oligonucleotides and are visible intracellularly when bound to target sequences after direct injection in accord with known methods. Oligomers comprising one or more such bases can be used in various fluorescent assays to detect complementary nucleic acid sequences. The test phenoxazine oligonucleotides bind to a target complementary RNA sequence upon direct injection at an $IC_{50}$ of 5–10 µM, with expression of a beta-galactosidase control gene remaining unaffected, and therefore are useful in antisense methods for inhibition of translation of target RNAs in living cells.

Phosphinate nucleomonomers mean nucleotide analogs comprising a phosphinate moiety of the structure $(R^1)(R^2)$ P(O)—O—CH$_2$—O— 5', $(R^1)(R^2)$P(O)—O—CH$_2$—O— 3' and $(R^1)(R^2)$P(O)—O—CH$_2$—O— 2', where 5' refers to the 5' methylene carbon of an ribose, 2'-deoxyribose, 3'-deoxyribose or an analog such as 2' or 3' protected ribose, 2'- or 3'-deoxyribose, arabinose or a carbocyclic analog of any of these sugars. 2' and 3' refer to the 2' and 3' positions respectively of ribose, arabinose, a deoxyribose or a carbocyclic analog of any of these sugars linked to a purine or pyrimidine base at the 1' position. The 2' or 3' position is optionally substituted with R.

Linkage means a moiety suitable for coupling adjacent nucleomonomers and includes both phosphorus-containing moieties and non phosphorus-containing moieties such as phosphodiester, thioformacetal, riboacetal and the like. A linkage usually comprises 2 or 3 atoms between the 5' position of a nucleomonomer and the 2' or 3' position of an adjacent nucleomonomer.

Halogen means a fluorine (F), chlorine (Cl), iodine (I) or bromine (Br) atom.

Oxophilic lewis acids include TMSOTf, BF$_3$ and TiCl$_4$.

Alkyl means branched or unbranched moieties such as methyl, ethyl, propyl, isopropyl, butyl, isobutyl, t-butyl, pentyl, isopentyl, hexyl and the like. As used herein, the number of carbon atoms in an alkyl group will generally be specified as, for example, alkyl (1–3C), which means alkyl groups limited to 1, 2 or 3 carbon atoms. Where no designation of the number of carbon atoms is made, alkyl refers to moieties having 15, 20, 30, 40 or more carbon atoms.

Substituted alkyl means an alkyl moiety substituted with 1, 2 or 3 substituents selected from the group halogen, nitro (NO$_2$), cyano (CN), O-alkyl (1–10C), O-aryl (1–10C), COOR$^8$, COR$^8$, SO$_2$R$^8$, N(R$^8$)$_2$ and CON(R$^8$)$_2$, wherein R$^8$ is as defined.

Alkenyl and alkynyl mean branched or unbranched moieties having 1, 2, or 3 double or triple bonds. The number of carbon atoms will usually be designated as described for alkyl groups. Alkenyl includes allyl (—CH$_2$—CH═CH$_2$).

Aryl means aromatic moieties that contain only carbon atoms in the ring(s) such a phenyl or naphthyl. Aryl will usually comprise 1, 2 or 3 aromatic rings.

Heteroaryl means aromatic moieties that contain carbon atoms and one or more heteroatoms in an aromatic ring(s). The heteroatom is usually oxygen (—O—), nitrogen (—NH—) or sulfur (—S—).

Substituted aryl means an aryl moiety substituted with 1, 2 or 3 groups or atoms including alkyl (1–10C) moieties, halogen, NO$_2$, CN, O-alkyl (1–10C), O-aryl (1–10C), COOR$^8$, COR$^8$, SO$_2$R$^8$, N(R$^8$)$_2$ and CON(R$^8$)$_2$, wherein R$^8$ is as defined.

Substituted heteroaryl means a heteroaryl moiety substituted with 1, 2 or 3 groups or atoms including alkyl (1–10C) moieties, halogen, NO$_2$, CN, O-alkyl (1–10C), O-aryl (1–10C), COOR$^8$, COR$^8$, SO$_2$R$^8$, N(R$^8$)$_2$ and CON(R$^8$)$_2$, wherein R$^8$ is as defined.

A protecting group donor is a molecule used to provide a specific protecting group. For example, the protecting group donor for the DMT protecting group is DMT-chloride and the protecting group donor for the benzoyl protecting group is benzoyl chloride. Protecting groups donors and their use has been described (see for example: Greene et al, supra; M. J. Gait *Oligonucleotide Synthesis, a Practical Approach* (1984) IRL Press, Ltd., Oxford). Protecting groups of structure $R^{7B}$ and $R^{7D}$ are removed under reducing acidic conditions, such as those shown in example 18 and FIG. 1. $R^{7B}$ protecting groups such as DMT or MMT are removed by known methods such as treatment with a reducing agent such as triethylsilane, pyrrol or a mercaptan, an acid (such as DCA) and a trityl cation scavenger. $R^{7D}$ protecting groups are removed by treatment with a reducing agent such as NaBH$_3$CN and an acid such as solvent acetic acid (or solvent acetic acid with 1–10% DCA, generally 2–5% DCA).

Abbreviations used herein include DBU (1,8-diazabicyclo[5.4.0]undec-7-ene), DCA (dichloroacetic acid), Et$_3$SiH (triethylsilane), FMOC (9-fluorenylmethoxycarbonyl), MsOH (methanesulfonic acid), DMT-Cl (4,4'-dimethoxytrityl chloride), DMT-T (thymidine protected with DMT at 5' position), DMF (dimethylformamide), piv (pivaloyl, (CH$_3$)$_3$CC(O)O—), PA (2-chloro-4H-1,3,2-benzodioxaphosphorin-4-one), Ph (phenyl), MeOH (methanol), TMSOTf (trimethylsilyl triflate), NBS (N-bromosuccinimide), NIS (N-iodosuccinimide), and DEAD (diethylazodicarboxylate).

Exemplary nucleomonomers include species wherein R$^1$ and R$^2$ are independently methyl, ethyl, propyl, isopropyl, butyl, isobutyl, t-butyl, phenyl, 1- or 2-naphthyl, 2-, 3- or 4-cyanophenyl, 2-, 3- or 4-methylphenyl, 2-, 3- or 4-ethylphenyl, 2-, 3- or 4-methoxyphenyl, 2-, 3- or 4-nitrophenyl, 2-, 3- or 4-fluorophenyl, 2-3- or 4-pyridinyl, 2-, 4- or 5-pyrimidinyl, 2-, 4- or 5-oxazolyl, 2-, 4- or 5-thiazolyl, 2- or 3-thienyl or 2- or 3-furanyl. R$^1$ and R$^2$ will usually be the same.

Exemplary nucleomonomers also include species wherein R is H, OH, F, O-methyl, O-ethyl, O-propyl or O-allyl, R$^6$ is O and B is adenine, guanine, cytosine, thymine, uracil, 7-deazaadenine, 7-deazaguanine, 5-(1-propynyl)uracil, 5-(1-propynyl)cytosine, N$^6$-benzoyladenine, N$^2$-isobutyrylguanine, N$^4$-benzoylcytosine, N$^4$-formamidinylcytosine or N$^4$-formamidinyl-5-(1-propynyl)cytosine. Nucleomonomers include species wherein R$^5$ (when present) is methyl, ethyl, propyl or isopropyl; R$^{7A}$ is an electron-withdrawing protecting group including acyl groups (2–18 C such as acetyl and the like), benzoyl, aryl and heteroaryl; and R$^{7B}$ is a substituted benzyl such as trityl, 4-methoxytrityl and 4,4'-dimethoxytrityl.

An important aspect of the present invention is the finding by the present inventors that the phosphinate nucleomonomer used to generate an acetal linkage is relatively stable compared to alkyl phosphates (Quaedflieg et al *Synthesis* (1993) 6:627; Quaedflieg *Tet Lett* (1992) 33:3081). The stability of the monomers permits recovering and storing the compounds for use as needed. However, the invention phosphinate nucleomonomers are reactive enough to permit high coupling yields for oligomer synthesis. The use of the invention phosphinate nucleomonomers permits both oligonucleotide analog synthesis at high yields per coupling step and efficient solution phase synthesis of acetal linked oligonucleotide analogs.

Another aspect of the invention nucleomonomers is their use to generate thioformacetal linkages by coupling under basic conditions. Such conditions give improved oligomer yields using nucleomonomers having purine or purine analog bases because depurination associated with acid coupling is reduced or eliminated. This is particularly true for linkages through the 3' position where R at the 2' position is hydrogen.

Another aspect of certain invention nucleomonomers is that enhanced crystallinity is present especially for nucleomonomers having the structures such as 11a–13

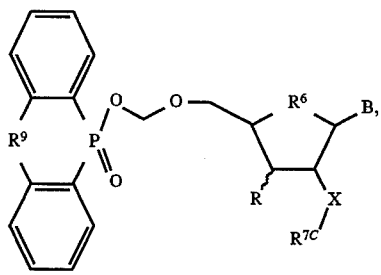

11a

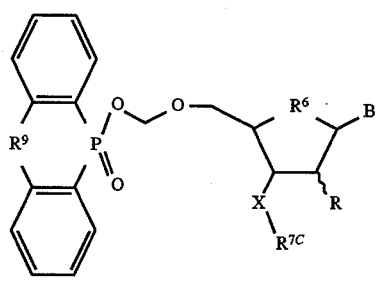

11b

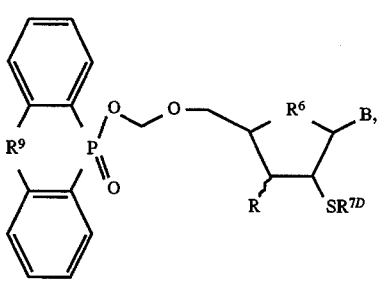

11g

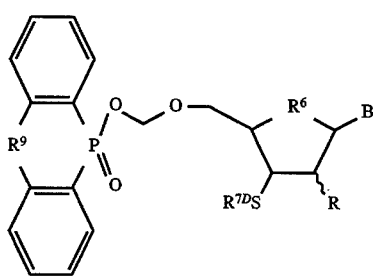

11h

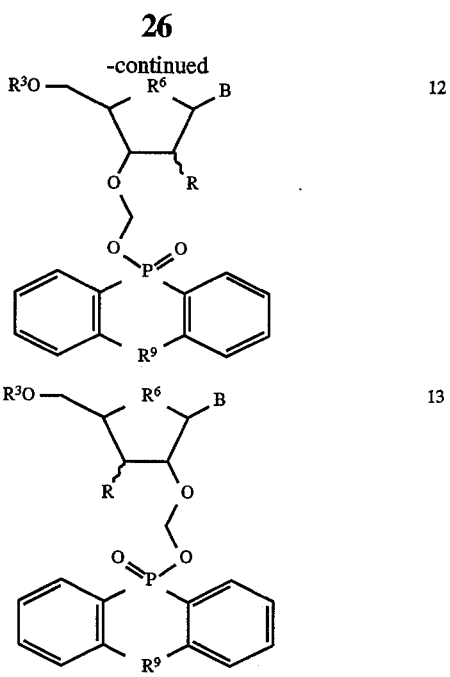

wherein B, R, $R^3$, $R^6$ and $R^{7D}$ have the meanings given; $R^{7C}$ is $R^{7A}$, $R^{7B}$, $OR^3$ or hydrogen; X is oxygen or sulfur; and $R^9$ is O, $CH_2$, C(O) or $CF_2$. This group of nucleomonomers all have the tricyclic structure formed by $R^1$ and $R^2$ and the phosphorus atom to which they are attached. The enhanced crystallinity of such nucleomonomers, particularly the free acids, relative to nucleomonomers where $R^1$ and $R^2$ together do not form any ring permits using simpler purification procedures (i.e., crystallizing and filtering) for nucleomonomer preparation. The protected species are made by reaction of a protected nucleomonomer with the phosphinate in the presence of an oxidizing agent (NIS, NBS, and the like) as shown in FIG. 1.

Nucleomonomers comprising $R^{7D}$, e.g., compounds of structure 7a, 8a, 11c, 11d, 12b, 13b, 30a and 31a, defined above, are synthesized by coupling the free thiol form of compounds of structure 34–41 protected nucleomonomer having a leaving group at the position to be substituted by the sulfur nucleophile. In the case of the 3' or 2' positions, the leaving group, such as methanesulfonate or anhydro nucleoside, needs to be on the opposite side of the 5-membered ribose ring relative to the position of the sulfur in the final product. The displacement reaction is usually carried out under basic conditions, but acidic conditions can be employed, particularly with 2,2' or 2,3' anhydro pyrimidine nucleosides. The protecting groups of structure 34–41 and 45 are electron withdrawing, stable to $S^-$ anion and can be selectively removed. These groups thus combine the properties of both $R^{7A}$ and $R^{7B}$ protecting groups, permitting synthesis of thioformacetal linked oligomers without a requirement to synthesize both $R^{7A}$ and $R^{7B}$ protected nucleomonomers as intermediates. The structure 34–41 and 45 protecting groups are suitable for protecting thiol groups on compounds other than nucleomonomers, including cystine-containing peptides or proteins. These protecting groups are thus useful for protecting thiol groups on organic molecules where a protecting group stable to $S^-$ anion or nucleophilic conditions is desired. Some of the structure 34–41 and 45 molecules (such as 2-thioquinoline and 2-thiopyrimidine) are available from commercial sources. These compounds can be prepared from the corresponding alcohol by standard methods.

Coupling of the phosphinate-protected nucleomonomers is accomplished in the presence of a non-nucleophilic base or a mildly nucleophilic base and a polar solvent. Suitable non-nucleophilic base and solvent systems include DBU in DMF and formamide (about 1:1 v/v DMF:formamide), sodium trimethylsilanoate in THF, sodium trimethylsilanoate in DMF, sodium trimethylsilanoate in DMF and formamide (about 1:1 DMF:formamide), cesium carbonate in DMF and sodium ethoxide in ethanol. Suitable DMF:formamide ratios include DMF present in the range from 25% to 75%, including any amount of DMF within this range in 1% increments including 30%, 40%, 45%, 55%, 60% or 70%. Generally, the solvent will not contain water, but, when present, water will constitute less than about 40% or less than about 30% by volume of the solvent and in general will constitute about 1 to 20% of total solvent by volume.

Ortholithiation of the bis-phenyl ether (diphenyl ether) followed by reaction with 0.5 equivalent of the dichloridate species (Baldwin, *J Org Chem* (1967) 32:2176) will give the phosphinic acid which is then incorporated into monomers by oxidation using an oxidizing agent such as NIS. Phosphinate species can be made where $R^1$ and $R^2$ are the same or different (Baldwin, *J Org Chem* (1967) 32:2176; Baldwin, *J Org Chem* (1967) 32:2172). Species where $R^1$ and $R^2$ are both alkyl groups have been described (*Zh Obshch Khim* (1990) 60:833).

Oligomer synthesis shown in the figures exemplifies using phosphoramidite chemistry in order to synthesize oligomers having mixed linkage types, e.g. phosphorus-containing linkages and acetal linkages. Phosphoramidite groups suitable for oligomer synthesis are well known (see, for example, U.S. Pat. Nos. 4,458,066; 4,415,732 and Re. 34,069). Other chemical methods could also be used according to well known methods without modification of the protocols shown. For example, oligomers having one or more phosphorus containing linkages can be synthesized using H-phosphonate chemistry as described in U.S. Pat. No. 4,959,463. For H-phosphonate chemistry, a phosphorylating reagent such as tris-(1,2,4)(triazole)phosphite is used to prepare oligomers containing a 2', 3' or 5' H-phosphonate group. Oligonucleotide analogs containing 3',5'-formacetal (3' —O—CH$_2$—O— 5'), 2',5'-formacetal (2' —O—CH$_2$—O— 5'), 3',5'-thioformacetal (3' —S—CH$_2$—O— 5'), 2',5'-thioformacetal (2' —S—CH$_2$—O— 5'), 5',3'-thioformacetal (3' —O—CH$_2$—S— 5'), and 5',2'-thioformacetal (2' —O—CH$_2$—S— 5'), linkages and methods for their synthesis have been described (Ser. No. 07/874,334, WO 92/19637, WO 91/06692, Quaedflieg et al *Synthesis* 1993 6:627).

The following examples are meant to illustrate and not to limit the invention. All citations are incorporated herein by reference.

EXAMPLE 1

Figure 22:
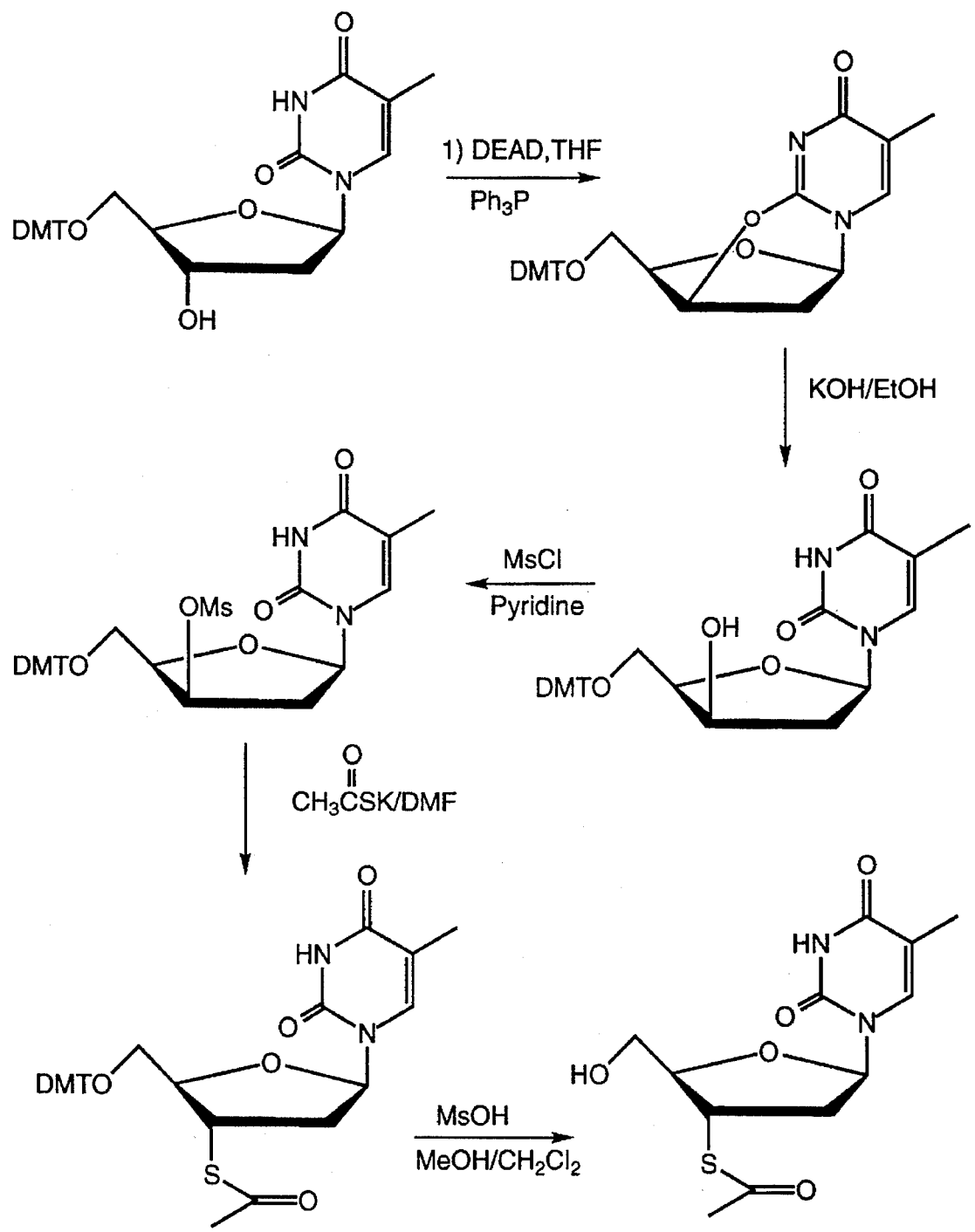
FIG. 22. Synthesis of a thymine nucleomonomer having a protected sulfur atom at the 3' position via a 2,3'-anhydro T intermediate.

FIG. 22 shows the reactions described in examples 1–4. To a solution of DMT-T (54.4 g, 0.1 mol) and triphenylphosphine (PPh$_3$) (31.4 g, 0.12 mol), was slowly added DEAD (18.9 mL, 0.12 mol) at 0° C. The reaction mixture was allowed to warm up to room temperature (RT) and stir overnight. TLC showed that starting material DMT-T disappeared. Evaporation of the solvent afforded a thick syrup. Flash chromatography first with 2/1 ethyl acetate (EtOAc) /Hexane, then 1/9 MeOH/CH$_2$Cl$_2$, gave anhydro-T, a white solid (47.0 g, 89%). $^1$H NMR (CDCl$_3$): δ 7.30 (m, 10H); 6.81 (m, 4H); 5.43 (d, J=3.8 Hz, 1H) 5.15 (brs, 1H), 4.27(m, 1H), 3.78 (s, 6H) 3.34 (m, 2H), 2.55 (m, 1H), 2.41 (m, 1H) 1.94 (s, 3H)

EXAMPLE 2

To a solution of anhydro-T (20 g, 38.0 mmol) in EtOH (300 mL), was added 1N KOH (100 mL, 100 mmol). The reaction mixture was refluxed for 2 h and TLC showed that starting material disappeared. The reaction mixture was then concentrated to about 100 mL in volume. With vigorous stirring, 5% HCl solution was added until the pH reached ~6. Then the mixture was extracted with EtOAc (ethyl acetate) twice. The combined organic layer was washed with brine and dried with Na$_2$SO$_4$. Evaporation of the solvent gave a white solid (20.5 g, 100%). $^1$H NMR (CDCl$_3$): δ 8.73 (brs, 1H), 7.68 (s, 1H) 7.30 (m, 9H), 6.84 (d, J=8.8 Hz, 4H) 6.20 (dd, J=8.3, 2.4 Hz), 4.47 (brs, 1H) 4.03 (m, 1H), 3.79 (s, 6H), 3.61 (dd, J=10.2, 4.9 Hz, 1H)3.50 (dd, J=10.2, 5.6 Hz, 1H), 3.14 (brs 1H) 2.56 (m, 1H), 2.13 (m, 1H) 1.80 (s, 3H). The crude product was employed in the next step without further purification.

The solid obtained above (20 g, 37 mmol) was dissolved in 200 mL dry pyridine in the presence of 0.5 mL Et$_3$N. To the mixture, methanesulfonyl chloride (3.41 mL, 44 mmol) was added. The resulting mixture was stirred overnight at room temperature. After most of the pyridine evaporated, the reaction mixture was partitioned between H$_2$O and EtOAc. The aqueous phase was extracted one more time with EtOAc. The combined organic layer was washed with H$_2$O and brine and then dried with Na$_2$SO$_4$. Evaporation of the solvent afforded a pale yellowish solid (23 g, 100%). $^1$H NMR (CDCl$_3$): δ 8.65 (s, 1H), 7.30 (m, 10H), 6.85 (d, J=8.9 Hz, 4H) 6.28 (dd, J=8.10, 3.4 Hz), 5.28 (m, 1H) 4.18 (m, 1H), 3.80 (s, 6H), 3.65 (dd, J=9.8, 5.6 Hz) 3.38 (dd, J=9.8, 6.5 Hz), 2.79 (s, 3H), 2.78 (m, 1H) 2.49 (m, 1H), 1.81 (s, 3H).

EXAMPLE 3

The mesylation product of example 2 (21 g, 34 mmol) was dissolved in 200 mL DMF. Potassium thioacetate was added to the solution. The reaction mixture was heated with an oil bath (bath temperature ~90° C.) for a few hours until the starting material was consumed. Evaporation of DMF solvent afforded a dark mixture. H$_2$O was added to the residue and the aqueous layer was extracted with EtOAc three times. The combined organic layer was washed with H$_2$O and brine and dried with Na$_2$SO$_4$. Evaporation of the solvent produced a dark brown solid (22.0 g). Without further purification, the dark solid was used in the next step. $^1$H NMR (CDCl$_3$): δ 7.97 (s, 1H), 7.67 (s, 1H), 7.30 (m, 9H) 0.83 (d, J=8.8 Hz, 4H), 6.22 (m, 1H) 4.29 (m, 1H), 4.02 (m, 1H), 3.79 (s, 6H) 3.50 (dd, J=10.8, 2.3, 1H) 3.37 (dd, J=10.8, 3.0 Hz, 1H), 2.65 (m, 1H) 2.41 (m, 1H), 2.32 (s, 3H), 1.44 (s, 3H).

EXAMPLE 4

The dark solid was dissolved in 250 mL 1/9 MeOH/ CH$_2$Cl$_2$ solution. Methanesulfonic acid (~10 mL) was then added. The reaction mixture was stirred at RT for 2 h and TLC showed that the starting material disappeared. The saturated KHCO$_3$ aqueous solution was added slowly and cautiously to the reaction mixture until evolution of gas ceased. The mixture was then extracted with CH$_2$Cl$_2$ twice and the combined organic layer was washed with H$_2$O and brine, and then dried over Na$_2$SO$_4$. Filtration and evaporation of the solvent gave an oily residue. The residue was eluted with 1/1, 1/2 and 1/3 Hex/EtOAc by silica gel flash chromatography. An oil (8.0 g, 89%) was obtained. $^1$H NMR (CDCl$_3$): δ 8.05 (brs, 1H), 7.85 (s, 1H) 6.10 (dd, J=6.6, 3.2 Hz, 1H), 4.01 (m, 3H), 3.75 (m, 1H), 2.79 (dd, J=7.7, 5.7 Hz, 1H) 2.49 (m, 1H), 2.40 (5, 3H), 1.94 (s, 3H).

EXAMPLE 5

Benzoyl peroxide (19.0 g, 78.0 mmol) was added within 1 h to a cooled (0° C.) and stirred mixture of 5'-hydroxy-3'-thioacetate thymidine (7.8 g, 26 mmol), Me$_2$S (19.0 mL, 260 mmol) in 260 mL acetonitrile. The ice bath was removed and the reaction mixture was allowed to stir at RT for 6 h. Upon completion of the reaction, the reaction mixture was concentrated in vacuo and then partitioned between EtOAc and saturated NaHCO$_3$, H$_2$O and brine successively and then dried over Na$_2$SO$_4$. Evaporation of the solvent gave an oil residue. The crude product was purified by flash chromatography with 2/1 and 1/1 Hex/EtOAc to give a solid (5.0 g, 62%). $^1$H NMR (CDCl$_3$): δ 8.58 (brs, 1H); 7.69 (s, 1H) 6.23 (dd, J=6.6, 4.9 Hz), 4.76 (s, 2H) 4.12 (m, 2H), 3.90 (dd, J=10.9, 18 Hz, 1H) 3.75 (dd, J=10.9, 2.5 Hz, 1H), 2.55 (m, 1H), 2.43 (m, 1H), 2.39 (s, 3H) 2.20 (5, 3H), 1.97 (s, 3H).

EXAMPLE 6

The 5'-methylthiomethyl-3'-thioacetylthymidine (MTM) ether of example 5 (5.3 g, 14.8 mmol) was dissolved in the presence of molecular sieves in 1/1 1,2-dichloroethane/ether (100 mL). Diphenyl phosphinic acid (3.5 g, 16.3 mmol) and N-iodosuccinimide (NIS) (3.3 g, 14.8 mmol) were added successively. The reaction mixture turned darker and was stirred at RT for 1 h. Upon completion the reaction mixture was quenched with saturated Na$_2$S$_2$O$_3$ and NaHCO$_3$ solution and extracted with CH$_2$Cl$_2$ three times. The combined organic layer was washed with H$_2$O and brine and then dried over Na$_2$SO$_4$. Filtration and evaporation in vacuo afforded a solid. The crude product was purified with 1/1 Hex/EtOAc and 100% EtOAc by flash chromatography to give a white solid (7.0 g, 90%). $^1$H NMR (CDCl$_3$): δ 7.93 (s, 1H), 7.80 (m, 4H), 7.50 (m, 7H) 6.20 (m, 1H), 5.40 (m, 2H), 4.07 (m, 4H) 2.41 (m, 1H) 2.33(@, 3H), 2.30 (m, 1H), 1.84 (s, 3H).

EXAMPLE 7

The phosphinate of example 6 (2.30 g, 4.3 mmol) was dissolved in 20 mL EtOAc at 0° C. To this solution, was added 20 ml of saturated NH$_3$ in MeOH. The reaction mixture was stirred at 0° C. for 10 min. and then the solvents were quickly evaporated. The residue was redissolved in EtOAc (100 ml) and 5% HCl was added to pH~3. The acidified mixture was separated, and the aqueous layer was extracted again with 100 ml EtOAc. The combined organic layer was washed with NaHCO$_3$, H$_2$O) and brine and dried over Na$_2$SO$_4$. Filtration and evaporation in vacuo gave a solid (HNMR of the crude product indicated the presence of a small amount of cyclized product).

The crude solid was immediately dissolved in 50 mL THF, diisopropyl ethyl amine (0.89 mL, 5.16 mmol) and DMT-Cl (1.75 g, 5.16 mmol) was added successively. The reaction mixture was kept under Argon and stirred at RT for 2 h. The reaction mixture was diluted with 100 mL EtOAc and quenched with H$_2$O). The mixture was partitioned and separated. The organic layer was washed with brine and dried over Na$_2$SO$_4$. Evaporation of the solvent gave a solid. The crude product was purified with 1/1 Hex/EtOAc and then 100% EtOAc by flash chromatography to give a white solid (2.6 g, 78%). $^1$H NMR (CDCl$_3$): δ 8.17 (s, 1H); 7.75 (dd, J=12.5, 7.0 Hz, 4H); 7.30 (br M, 18H); 6.79 (d, J=8.8 Hz, 4H) 6.00 (dd, J=6.8, 3.6 Hz, 1H); 5.28 (dd, J=9.5, 5.5 Hz, 1H); 5.16 (dd, J=10.5, 5.5 Hz, 1H) 3.98 (m, 2H), 3.74 (s, 6H), 3.65 (m, 1H) 2.74 (m, 1H), 2.16 (m, 2H), 1.72 (s, 3H).

EXAMPLE 8

To a solution of thioacetate from example 7 (0.23 g, 0.59 mmol) in MeOH (2 mL) at 0° C., was added 2 ml saturated NH$_3$ in MeOH. The reaction mixture was stirred at 0° C. for 30 min. and concentrated. EtOAc (20 ml) and saturated NH$_4$Cl (10 ml) was added to the residue. The bilayer solution was separated. The organic layer was washed with brine and dried over Na$_2$SO$_4$. Filtrate and concentration afforded a white solid (0.19 g, 95%). $^1$H NMR (CDCl$_3$): δ 8.37 (brs, 1H), 7.24 (s, 1H), 6.13 (dd, J=7.1, 3.9 Hz, 1H) 4.48 (dd, J=12.6, 4.4 Hz, 1H) 4.33 (dd, J=12.6, 2.5 Hz, 1H) 4.0 (m, 1H); 3.37 (m, 1H) 2.52 (m, 1H); 2.40 (m, 1H), 1.93 (s, 3H) 1.83 (d, J=7.2 Hz, 1H), 1.25 (s, 9H).

EXAMPLE 9

Sulfurhydryl (44.0 mg, 0.129 mmol) and phosphinate from example 8 (102 mg, 0.129 mmol) were dissolved in 1/1 DMF/Formamide (1.3 mL) mixture. The reaction mixture was immediately purged with Ar. DBU (18 μl, 0.129 mmol) was then added and the reaction mixture was stirred at RT for 24 h. Upon completion, the mixture was diluted with 20 ml of EtOAc and washed with H$_2$O and brine. The resulting organic layer was dried over Na$_2$SO$_4$. Evaporation and purification with 3% MeOH in CH$_2$Cl$_2$ afforded a white solid (100 mg, 85%). $^1$H NMR (CDCl$_3$): δ 7.30 (br M, 11H), 7.31 (m, 4H), 6.04 (m, 2H), 4.78 (d, J=12.0 Hz, 1H); 4.61 (d, J=12.0 Hz, 1H), 4.48 (dd, J=12.2, 4.4 Hz, 1H) 4.25 (dd, J=12.2, 2.6 Hz, 1H), 4.03 (m, 1H), 3.93 (m, 1H) 3.78 (s, 6H), 3.38 (m, 1H); 3.27 (m, 1H) 2.71 (m, 1H); 2.46 (m, 2H), 2.20 (m, 1H) 1.92 (s, 3H); 1.82 (s, 3H), 1.24 (s, 9H).

EXAMPLE 10

S-DMT-Dimer (0.80 g, 0.088 mmol) was dissolved in CH$_2$Cl$_2$ (3 ml) in the presence of mercaptoethanol (0.135 mL, 2.2 mmol). Methanesulfonic acid (11.4 μl, 0.176 mmol) was subsequently added. The reaction mixture was stirred at RT for 4 h while monitored by TLC. Upon completion, the reaction was diluted with CH$_2$Cl$_2$ (25 mL) and washed with H$_2$O and brine several times. The organic layer was then dried with Na$_2$SO$_4$ and concentrated in vacuo. Flash chromatography of the crude product with 4% MeOH in CH$_2$Cl$_2$ gave a white solid (51 mg, 95%). $^1$H NMR (CDCl$_3$): δ 9.15 (br$_o$ S, 2H), 7.42 (s, 1H), 7.27 (s, 1H) 6.18 (m, 2H), 4.89 (d,J=12.1 Hz, 1H) 4.81 (d, J=12.1 Hz, 1H), 4.41 (dd, J=12.6, 4.9 Hz, 1H) 4.33 (dd, J=12.6, 2.7 Hz, 1H0 4.15 (m, 1H), 3.92 (m, 2H) 3.38 (m, 3H), 2.51 (m,4H) 1.92 (s, 3H), 1.89 (s, 3H) 1.23 (s, 9H).

EXAMPLE 11

Dimer (0.29 g, 0.47 mmol) and phosphinate from example 8 (0.45 g, 0.57 mmol) were dissolved in 1/1 DMF/formamide (5 mL) under Ar. DBU (68 μl, 0.49 mmol) was subsequently added. The reaction mixture was stirred at RT for 36 h. After the reaction was completed, EtOAc (25 mL) was added. The solution was then washed with H$_2$O and brine several times. The resulting organic layer was dried with Na$_2$SO$_4$ and concentrated in vacuo to give a solid. Flash chromatography with 4% MeOH in CH$_2$Cl$_2$ of the crude product afforded a white solid (0.45 g, 80%). $^1$H NMR (CDCl$_3$): δ 8.93 (s, 1H), 8.91 (s, 1H), 8.80 (s, 1h), 7.30 (m, 12H), 6.81 (m, 4H), 6.81 (m, 4H), 6.01 (m, 3H) 4.81 (d, J=12.1 Hz, 1H), 4.81 (s, 2H), 4.60 (d, J=12.1 Hz, 1H), 4.39 (dd,J=12.4, 5.0 Hz, 1H) 4.31 (dd, J=12.4 Hz, 2.6 Hz, 1H(, 4.13 (m, 1H) 3.90 (br M, 2H), 3.78 (s, 6H) 3.34 (m, 3H), 2.71 (m, 1H), 2.48 (m, 4H) 2.20 (m, 1H), 1.91 (s, 3H), 1.88 (s, 3H) 1.83 (s, 3H), 1.23 (s, 9H).

This method was used to synthesize a T$_5$ 3',5'-thioformacetal linked oligonucleotide analog. The synthesis of the center synthon required the introduction of a 5' phosphinate acetal and the 3' appropriately protected mercaptan. The method entails the switching of the thiol protecting group from acetyl to dimethoxy trityl. This was necessary because acyl protection was not stable to the thiol anion used during the coupling step. Further improvement of the method would be the elimination of the extra steps necessary to switch protecting groups.

EXAMPLE 12

Figure 20:
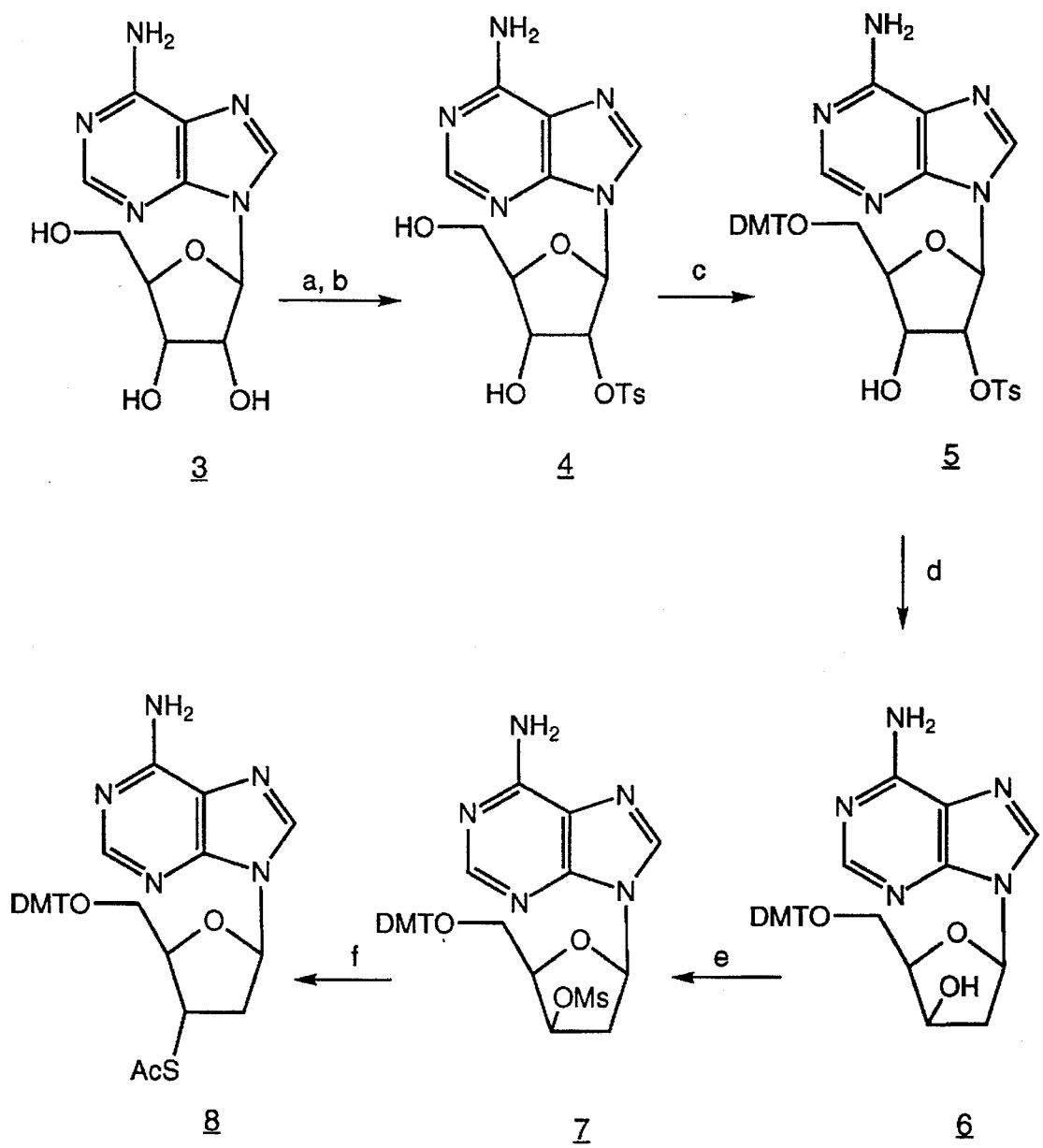
FIG. 20. Synthesis of purine nucleomonomer having a protected sulfur atom at the 3' position.

FIG. 20 shows a method that was used to obtain an adenine nucleomonomer. The method is suitable for synthesis of nucleomonomers containing purines with 2' or 3' thioacyl groups or other protected thiol species. As shown in FIG. 20, conversion of 3 to 4 was accomplished by (a) refluxing Bu₂SnO (dibutyltin oxide) in methanol and (b) TsCl, triethylamine in methanol; (c) 5 was synthesized by reaction of DMTCl with 4 in pyridine at room temperature; (d) 6 was synthesized by reaction of NaB(C₂H₅)₃H with 5 in THF at −78° C.; (e) 7 was synthesized by reaction of mesyl chloride with 6 in pyridine at room temperature; (f) 8 was synthesized by reaction of potassium thioacetate with 7 in DMF at −70° C. Yields of each product shown in FIG. 20 ranged from 65% to 85%.

EXAMPLE 13

Figure 21:
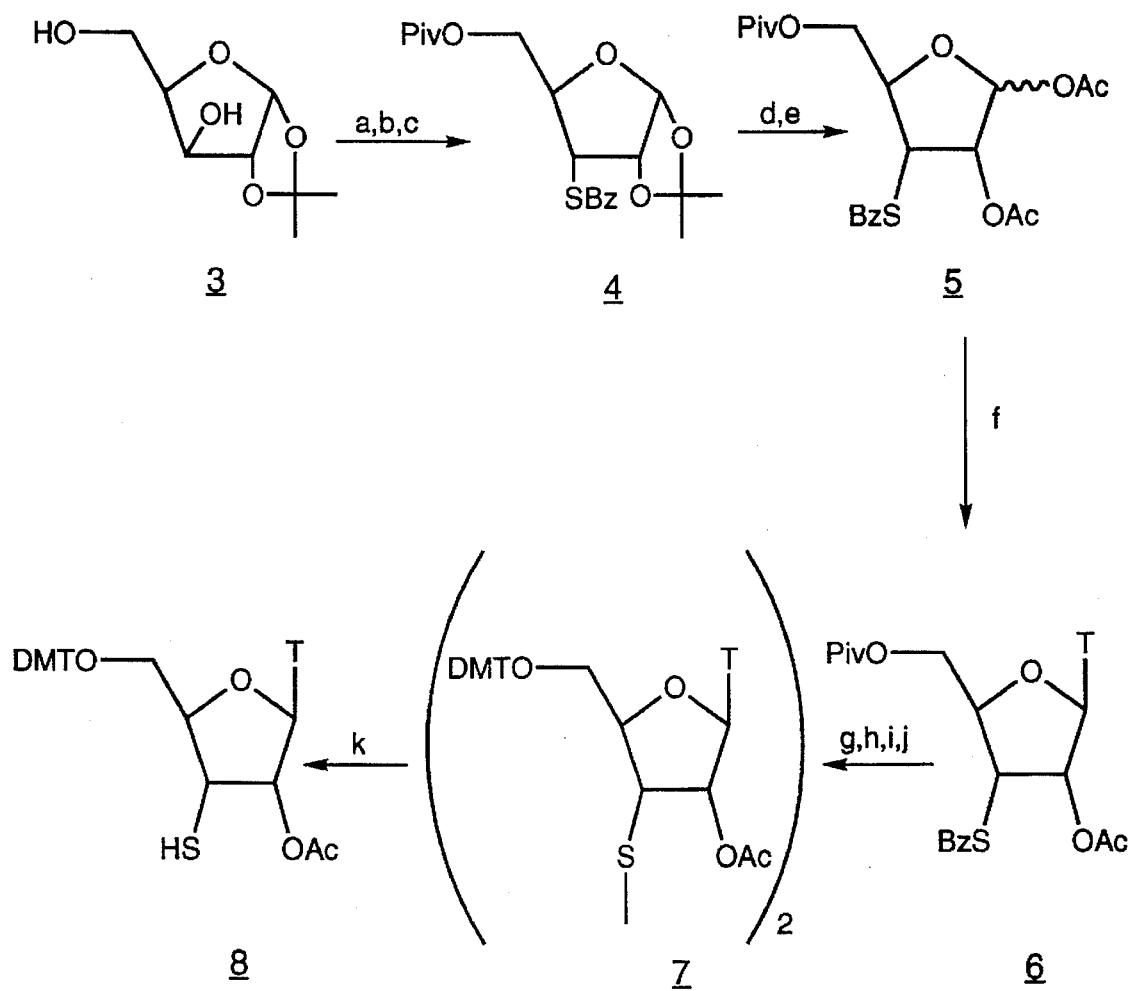
FIG. 21. Synthesis of a nucleomonomer having a protected sulfur atom at the 3' position.

FIG. 21 shows an alternate method to obtain nucleomonomers with 2' or 3' thioacyl groups or other protected thiol species, including purine nucleomonomers. Conversion of 3 to 4 was accomplished by (a) reacting 3 with trimethylacetyl chloride in pyridine, (b) (TfO)₂O in CH₂Cl₂ and pyridine and (c) thiobenzoic acid and NaH in DMF at 0° C.; (d) 5 was synthesized by reaction in 75% formic acid at 50° C. and (e) Ac₂O in pyridine at room temperature; (f) 6 was synthesized by reaction of persilylated thymine (reaction with Bis (trimethylsilyl) acetamide) with TMSOTf in acetonitrile at 70° C.; 7 was synthesized by (g) reaction of 6 and NaOCH₃ in methanol, (h) I₂ in pyridine, (i) DMTCl in pyridine and (j) Ac₂O in pyridine; 8 was synthesized by (k) reaction of 7 with NaBH₄ in ethanol. 7: $^1$H-NMR δH(300 MHz, CDCl₃) 9.96 (s, 1H, —NH); 7.73 (s, 1H, 6H); 6.70–7.46 (m, 1H, Ar—H); 6.04 (d, 1H, H-1'); 3.82–3.97 (m, 2H, H-3' and H-4'); 3.78 (s, 6H, 2x-OCH₃); 3.54 (ddd, 2H, H-5'); 2.02 (s, 3H, —OAc); 1.65 (s, 3H, 5-CH₃). 7: MS: required 1235.4, found M⁺=1234.8. Yields of products 3–7 shown in FIG. 21 ranged from 60% to 90%.

EXAMPLE 14

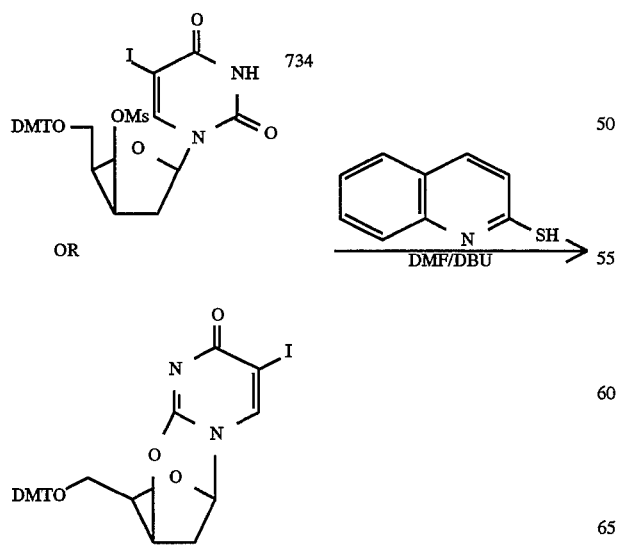

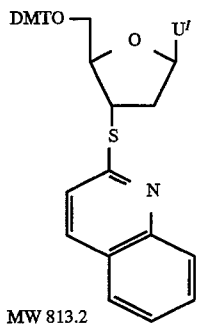

U$^I$ = 5-iodouracil

To a solution of mesylate-U (0.74 g, 1.0 mmol) in DMF (10 ml) was added 2-quinolinethiol (0.32 g, 2.0 mmol) and DBU (0.28 ml, 2.0 mmol). The reaction mixture was heated and stirred (bath temperature −95° C.) overnight. DMF was then evaporated in vacuo and the residue was dissolved in 60 m EtOAc. The solution was then washed with H₂O and brine, and dried over Na₂SO₄. Evaporation of the solvent and purification with 2/1 Hex/EtOAc by flash chromatography afforded a yellowish solid (0.43 g, 52%). $^1$H NMR (CDCl₃): δ 8.35 (s, 1H), 8.12 (s, 1H), 7.93 (d, J=8.4 Hz, 1H), 7.72 (d, J=8.5 Hz, 1H), 7.61–7.18 (m, 13H), 6.89 (m, 4H), 6.38 (t, J=6.2 Hz, 1H), 4.94 (m, 1H), 4.37 (m, 1H), 3.76 (s, 6H), 3.74 (m, 1H), 3.53 (m, 1H), 2.85 (m, 1H), 2.68 (m, 1H). The reaction could also be accomplished using 2,3'-anhydro-5'-DMT-thymidine as shown.

EXAMPLE 15

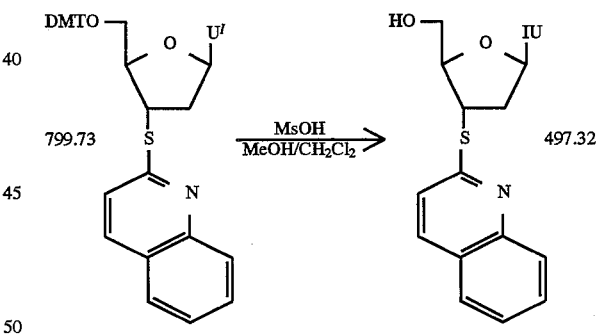

The starting material (14.2 g, 17.8 mmol) was dissolved in 10% MeOH/CH₂Cl₂ solution and MeOH (1.2 ml) was added. The reaction was stirred at r.t. for 2 h. Saturated NaHCO₃ solution was added cautiously until the evolution of CO₂ ceased. Then, the bilayer was separated and the organic layer was washed with H₂O and brine and dried over Na₂SO₄. Chromatography with 2/1 then 1/3 Hex/EtOAc of the crude product afforded an oil (7.6 g, 86%). $^1$H NMR (CDCl₃): δ 9.08 (s, 1H). 8.81 (brs, 1H), 8.00 (d, J=8.5 Hz, 1H), 7.96 (d, J=8.3 Hz, 1H), 7.77 (m, 2H), 7.52 (m, 1H), 7.24 (d, J-8.7 Hz, 1H), 6.18 (dd, J=5.8, 1.9 Hz, 1H), 4.35 (m, 1H), 4.09 (m, 2H), 3.85 (dd J=13.7, 1.7 Hz, 1H), 2.60 (m, 2H).

EXAMPLE 16

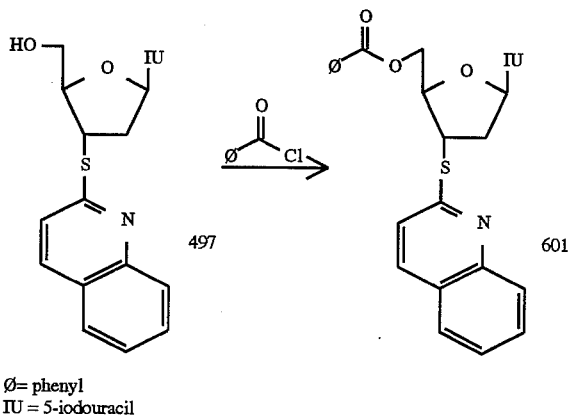

Ø = phenyl
IU = 5-iodouracil

To a solution of the starting material (2.0 g, 4.02 mmol) in pyridine (40 ml) was added øCOCl (0.51 ml, 4.42 mmol). The reaction mixture was stirred at r.t. for 2 h. Upon completion, the solvent was evaporated and the reside was redissolved in 100 ml EtOAc. The resulting solution was washed with $H_2O$ and brine and dried over $Na_2SO_4$. Evaporation of the solvent and purification with 1/1 Hex/EtOAc gave a white solid (2.2 g, 92%). $^1H$ NMR (CDCl$_3$); δ 8.63 (s, 1H), 8.13 (s, 1H), 8.07 (d, J=7.2 Hz, 1H), 7.94 (d, J=8.5 Hz, 1H), 7.92 (d, J=8.4 Hz, 1H), 7.51 (d, J=7.8 Hz, 1H), 7.61 (m, 2H), 7.48 (m, 3H), 7.21 (d, J=8.6 Hz, 1H), 6.35 (t, J=6.2 Hz, 1H), 4.96 (dd, J=12.4, 4.0 Hz, 1H), 4.71 (m, 2H), 4.59 (m, 1H), 2.69 (m, 2H), 2.05 (s, 3H).

EXAMPLE 17

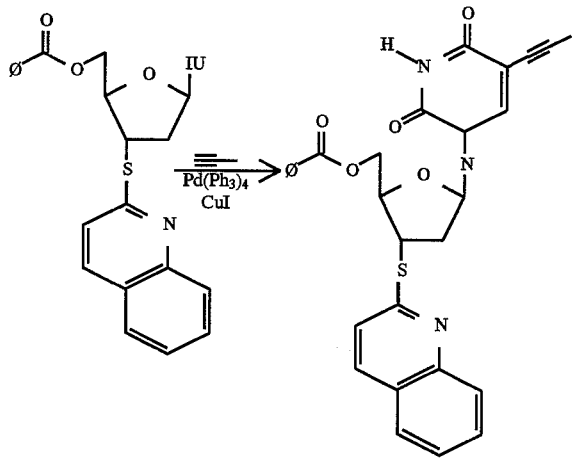

To a DMF (70 ml) solution of iodo-U (2.0 g, 3.33 mmol), triethyl amine (0.929 ml, 6.66 mmol) Pd(Pd$_3$)$_4$ (390 mg, 0.33 mmol) and CuI (0.13 g, 0.66 mmol) at 0° C. was bubbled with propyne for 15 min. Then the flask was sealed and the reaction was stirred overnight. Evaporation of the solvent afforded a residue. This residue was dissolved in EtOAc (130 ml) and washed with $H_2O$ and brine. The organic layer was dried over $Na_2SO_4$ and evaporated. Purification by chromatography with 2/1 then 1/1 Hex/EtOAc gave a solid (1.52 g, 89%). $^1H$ NMR (CDCl$_3$): δ 8.42 (s, 1H), 8.06 (d, J=7.2 Hz, 1H), 7.97 (s, 1H), 7.93 (d, J=8.5 Hz, 1H), 7.85 (d, J=7.2 Hz, 1H), 7.97 (s, 1H), 7.93 (d, J=8.5 Hz, 1H), 7.85 (d, J=8.5 Hz, 1H) 7.73 (d, J=8.0 Hz, 1H), 7.59 (m, 2H), 7.48 (m, 3H), 7.21 (d, J=80 Hz, 1H), 6.36 (t, J=6.0 Hz, 1H), 4.90 (dd, J=12.4, 2.8 Hz, 1H), 4.68 (m, 2H, 4.58 (m, 1H), 2.72 (m, 2H), 1.89 (s, 3H).

EXAMPLE 18

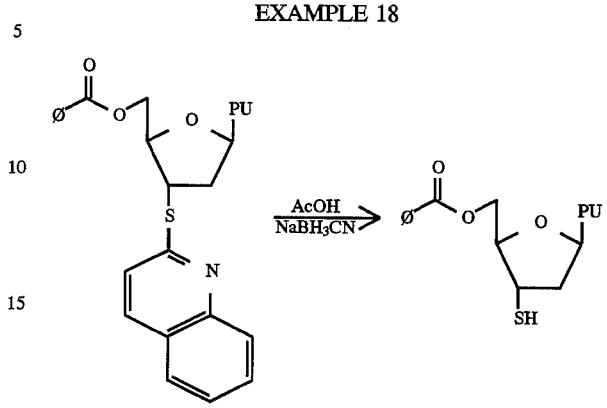

PU = 5-(1-propynyl)uracil

To a solution of compound the starting material (1.50 g, 2.92 mmol) in AcOH (60 ml), was added NaBH$_3$CN (0.92 g, 14.6 mmol) in 5 portions over a period of 2 h. The reaction mixture was then stirred at r.t. for an additional 3 h. After TLC indicated than s.m. disappeared, $H_2O$ (5 ml) was added to the reaction mixture and it was stirred for 30 min. Evaporation of the solvent afforded a residue. This residue was dissolved in EtOAc, which was washed with $H_2O$ and brine and dried over $Na_2SO_4$. Evaporation of the solvent and purification by chromatography with 1/1 then 1/4 Hex/EtOAc gave a white solid (1.02 g, 91%). $^1H$ NMR (CDCl$_3$): δ 8.22 (brs, 1H), 8.06 (d, J=7.2 Hz, 2H), 7.76 (s, 1H), 7.51 (m, 1H), 7.49 (m, 2H), 6.07 (dd, J=7.0, 2.8 Hz, 1H), 4.75 (dd, J=12.8, 7.5 Hz, 1H), 4.68 (dd, J=12.8, 2.4 Hz), 4.14 (m, 1H), 3.40 (m, 1H), 2.63 (ddd, J=14.2, 7.4, 2.8 Hz), 2.46 (m, 1H), 1.84 (s, 3H).

EXAMPLE 19

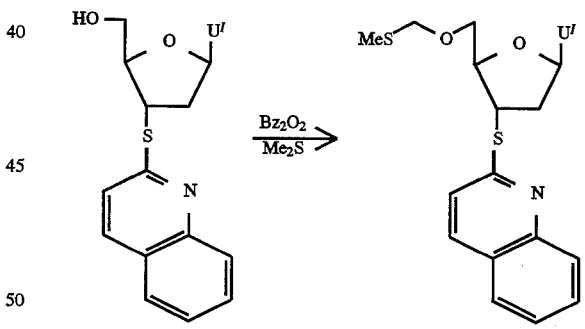

To a solution of the starting material (5.23 g, 10.5 mmol), and dimethyl sulfide (7.7 ml, 100.5 mmol) in CH$_3$CN (100 ml) at 0° C., benzoyl peroxide (Bz$_2$O$_2$) (7.8 g, 32 mmol) was added in three portion over a period of 1 h. The reaction was allowed to warm up to r.t. and was stirred for an additional 3 h. Evaporation of the solvent afforded a residue. This residue was dissolved in EtOAc (150 ml) and was subsequently washed with $H_2O$ and brine. The organic layer was dried over $Na_2SO_4$ and concentrated under reduced pressure to give an oily residue. Chromatography with 3/1 then 2/1 Hex/EtOAc of the crude product gave a yellowish solid (4.0 g, 71%). $^1H$ NMR (CDCl$_3$): δ 8.64 (s, 1H), 8.20 (s, 1H), 8.00–7.40 (m, 5H), 7.22 (d, J=7.8 Hz), 6.38 (m, 1H), 4.83 (m, 3H), 4.42 (m, 1H), 4.05 (m, 2H), 2.70 (m, 2H), 2.18 (s, 3H).

EXAMPLE 20

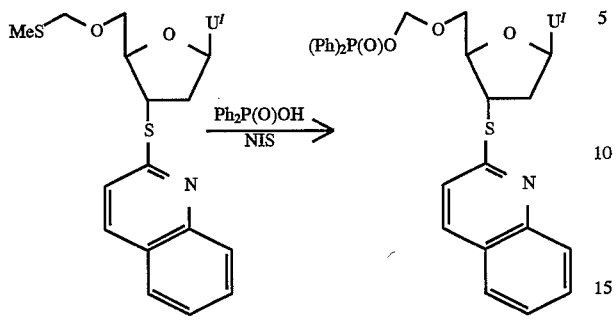

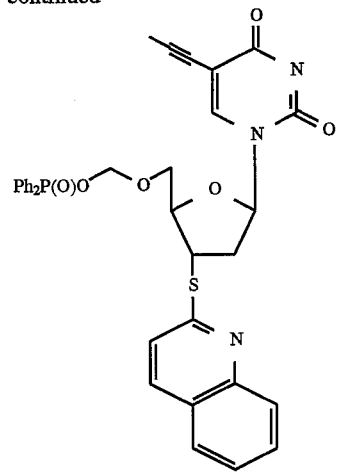

Ph = phenyl

The starting material MTM-ether (3.96 g, 7.10 mmol) was dissolved in 1/1 dichloroethane/ether mixture (71 ml). Diphenyl Phosphinic acid (1.86 g, 8.53 mmol) and NIS (1.86 g, 8.53 mmol) were added consecutively to the reaction solution. The reaction mixture was allowed to stir at r.t. for 1 h. and subsequently was quenched with saturated NaHCO$_3$/Na$_2$S$_2$O$_3$ solution. The mixture was extracted with EtOAc (100 ml×2) and the combined organic phase was washed with H$_2$O and brine and dried over Na$_2$SO$_4$. Evaporation and purification with 1/1 then 1/4 Hex/EtOAc afforded a white solid (3.63 g, 70%). $^1$H NMR (CDCl$_3$): δ 8.44 (s, 1H), 8.32 (brs, 1H), 7.95 (d, J=8.6 Hz, 1H), 7.90–7.30 (m, 14H), 7.19 (d, J=8.6 Hz, 1H), 6.31 (t, J=6.2 Hz, 1H), 5.56 (dd, J=9.5, 5.6 Hz, 1H) 5.48 (dd, J=11.1, 5.6 Hz, 1H), 4.58 (m, 1H), 4.39 (m, 1H), 4.28 (dd, J=10.9, 2.2 Hz, 1H), 4.16 (dd, J=10.9, 2.0 Hz, 1H), 258 (m, 2H).

The phosphinate starting material (3.6 g, 4.95 mmol) was dissolved in DMF (50 ml), Pd(Ph$_3$)$_4$ (0.0286 g, 0.247 mmol), CuI (0.094 g, 0.50 mmol) and Et$_3$N (1.38 mol, 9.0 mmol), were added to the solution. The reaction mixture was cooled to 0° C. and propyne gas was bubbled into the solution for 15 min. The reaction flask was then sealed and the reaction mixture was stirred overnight. Evaporation of the solvent and dilutions with EtOAc (150 ml) gave a solution which was washed with H$_2$O and brine. The resulting organic layer was dried over Na$_2$SO$_4$ and evaporated under reduced pressure. Purification by chromatography with 1/4 Hex/EtOAc, then 100% EtOH gave a white solid (2.08 g, 66%). $^1$H NMR (CDCl3): δ 8.23 (brs, 1H), 8.07 (s, 1H), 8.0–7.30 (m, 15H), 7.18 (d, J=8.6 Hz, 1H), 6.34 (t, J=6.1 Hz, 1H), 5.52 (dd, J=9.6, 5.6 Hz, 1H), 5.43 (dd, J=9.9 Hz, 5.6 Hz), 4.49 (m, 1H), 4.37 (m, 1H), 4.28 (m, 1H), 4.11 (m, 1H), 2.54 (m, 2H), 2.00 (s, 3H).

What is claimed is:

1. A compound having the structure

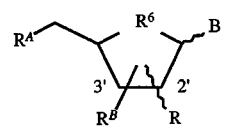

wherein

B is a purine or pyrimidine base;

R is H, O-alkyl (1–6C), O-alkenyl (1–6C) or halogen;

R$^A$ is XR$^{7A}$, XR$^{7B}$, SR$^{7D}$, OR$^3$ or OCH$_2$O(O)P(R$^1$)(R$^2$);

R$^B$ is linked to the 2' or 3' position and is XR$^{7A}$, XR$^{7B}$, XH, SR$^{7D}$, OR$^3$ or OCH$_2$O(O)P(R$^1$)(R$^2$), provided that either R$^A$ or R$^B$ is OCH$_2$O(O)P(R$^1$)(R$^2$), but not both R$^A$ and R$^B$ are OCH$_2$O(O)P(R$^1$)(R$^2$);

R$^1$ and R$^2$ are independently, alkyl (1–18C), alkyl (1–18C) substituted with 1, 2 or 3 substituents selected from the group consisting of halogen, nitro (NO$_2$), cyano (CN), O-alkyl (1–10C), O-aryl (6–10C), COOR$^8$, COR$^8$, SO$_2$R$^8$, N(R$^8$)$_2$ and CON(R$^8$)$_2$, wherein R$^8$ is alkyl (1–10C), aryl (6–10C), alkyl-aryl (7–12C) or heteroaryl (3–12C), aryl (6–10C), aryl (6–20C) substituted with 1, 2 or 3 groups or atoms selected from the group consisting of alkyl (1–10C),

EXAMPLE 21

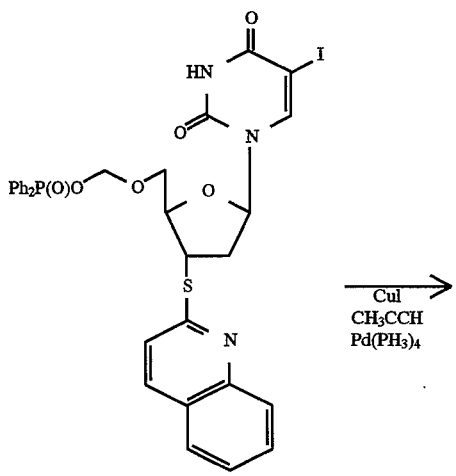

halogen, NO$_2$, CN, O-alkyl (1–10C), O-aryl (6–10C), COOR$^8$, COR$^8$, SO$_2$R$^8$, N(R$^8$)$_2$ and CON(R$^8$)$_2$;

heteroaryl (3–5C), heteroaryl (3–5C) substituted with 1, 2 or 3 groups or atoms selected from the group consisting of alkyl (1–10C), halogen, NO$_2$, CN, O-alkyl (1–10C), O-aryl (6–10C), COOR$^8$, COR$^8$, SO$_2$R$^8$, N(R$^8$)$_2$ and CON(R$^8$)$_2$ or R$^1$ and R$^2$ together with the phosphorus atom to which they are attached form the structure

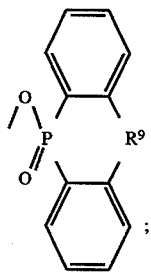

R$^3$ is a lewis acid stable protecting group;

R$^6$ is O or CH$_2$;

R$^{7A}$ is an electron withdrawing sulfur protecting group excluding benzyl;

R$^{7B}$ is a protecting group that is stable to S$^-$ anion nucleophiles;

R$^{7D}$ is a compound of structure 34–41 and 45

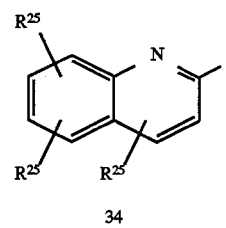 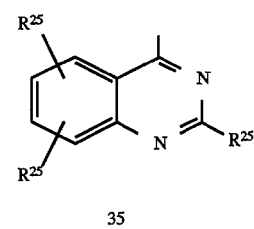

34   35

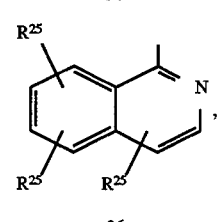 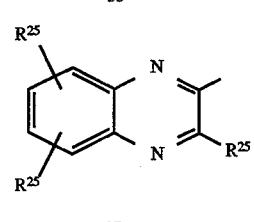

36   37

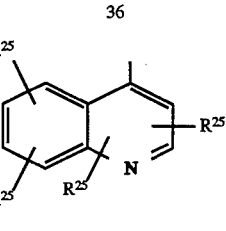 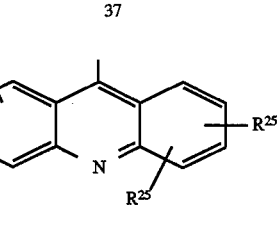

38   39

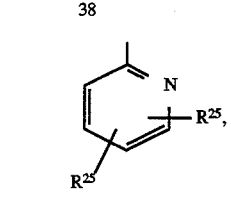 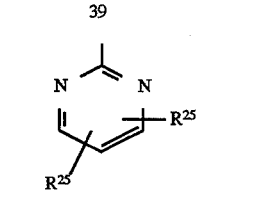

40   41

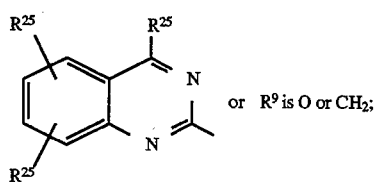

45

R$^9$ is O or CH$_2$;

R$^{25}$ is hydrogen, alkyl (1–6C), OR$^{26}$, C(O)R$^{26}$, C(O)OR$^{26}$, CN, NO$_2$, N(CH$_3$)$_2$, SO or SO$_2$ wherein R$^{26}$ is alkyl (1–6C) or substituted alkyl (1–6C), or two R$^{25}$ together on the same ring form a 5-membered aromatic ring comprising carbon atoms and 1 or 2 atoms or groups selected from the group consisting of S, O, N and N(CH$_3$)$_2$, provided that no adjacent atoms are both O, or two R$^{25}$ together on the same ring form a 6-membered aromatic ring comprising carbon atoms and 0, 1 or 2 nitrogen atoms, provided that there is no more than one N(CH$_3$)$_2$ group in any single protecting group; and X is oxygen (O) or sulfur (S).

2. The compound of claim 1 having the structure 3, 4, 5, 6, 7, 7a, 8, 8a, 9 10, 11g, 11h, 12b, 13b, 30, 30a, 31 and 31a

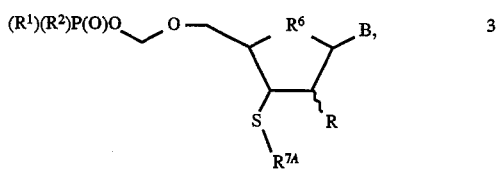 3

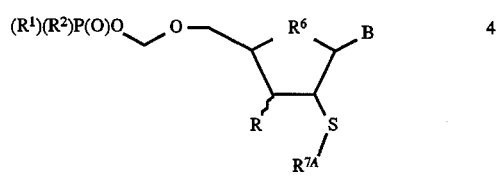 4

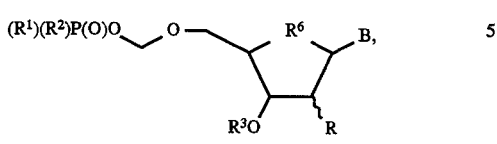 5

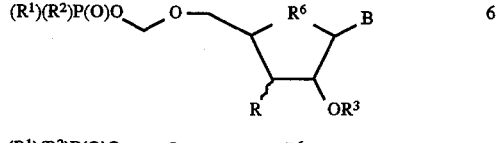 6

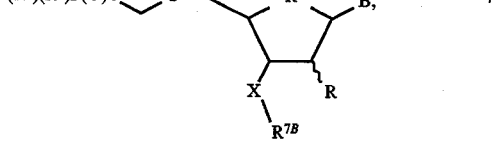 7

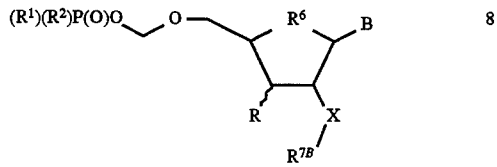 8

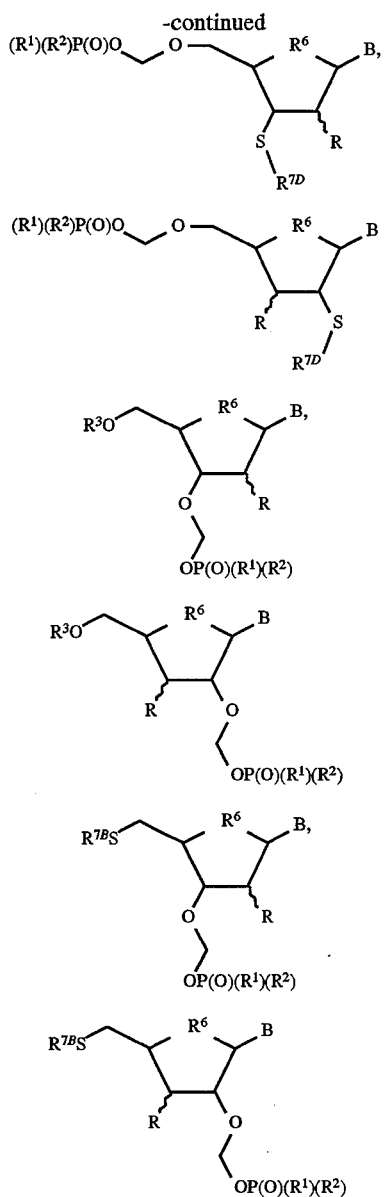
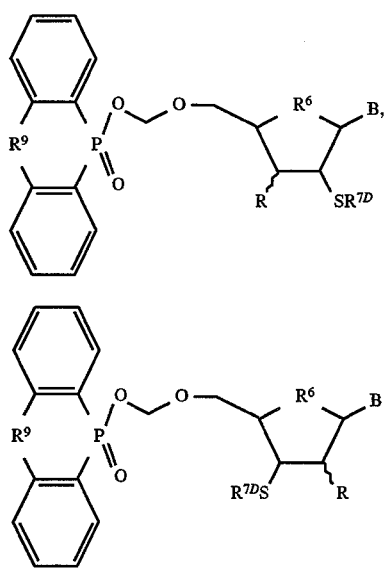
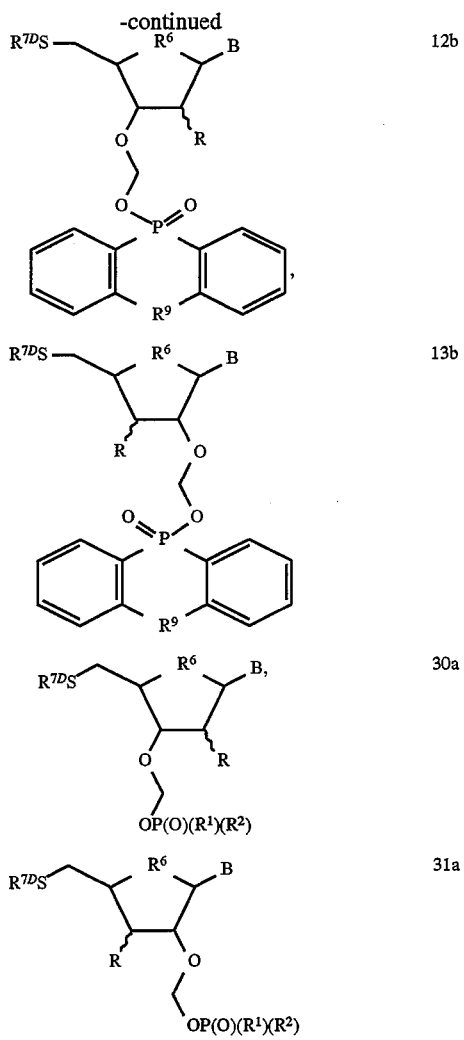

wherein

B is a purine or pyrimidine base;

R is H, O-alkyl (1–6C), O-alkenyl (1–6C) or halogen;

$R^1$ and $R^2$ are independently, alkyl (1–18C), alkyl (1–18C) substituted with 1, 2 or 3 substituents selected from the group consisting of halogen, nitro ($NO_2$), cyano (CN), O-alkyl (1–10C), O-aryl (6–10C), $COOR^8$, $COR^8$, $SO_2R^8$, $N(R^8)_2$ and $CON(R^8)_2$, wherein $R^8$ is alkyl (1–10C), aryl (6–10C), alkyl-aryl (7–12C) or heteroaryl (3–12C), aryl (6–10C), aryl (6–20C) substituted with 1, 2 or 3 groups or atoms selected from the group consisting of alkyl (1–10C), halogen, $NO_2$, CN, O-alkyl (1–10C), O-aryl (6–10C), $COOR^8$, $COR^8$, $SO_2R^8$, $N(R^8)_2$ and $CON(R^8)_2$;

heteroaryl (3–5C), heteroaryl (3–5C) substituted with 1, 2 or 3 groups or atoms selected from the group consisting of alkyl (1–10C), halogen, $NO_2$, CN, O-alkyl (1–10C), O-aryl (6–10C), $COOR^8$, $COR^8$, $SO_2R^8$, $N(R^8)_2$ and $CON(R^8)_2$ or $R^1$ and $R^2$ together with the phosphorus atom to which they are attached form the structure

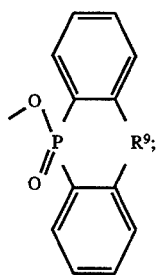

R³ is a lewis acid stable protecting group;

R⁵ is alkyl (1–6C) or aryl (6–10C);

R⁶ is O, CH₂, CHF or CF₂;

R⁷ is $R^{7A}$ or $R^{7B}$;

$R^{7A}$ is an electron withdrawing sulfur protecting group;

$R^{7B}$ is a protecting group that is stable to S⁻ anion nucleophiles;

$R^{7D}$ is a compound of structure 34–41 and 45

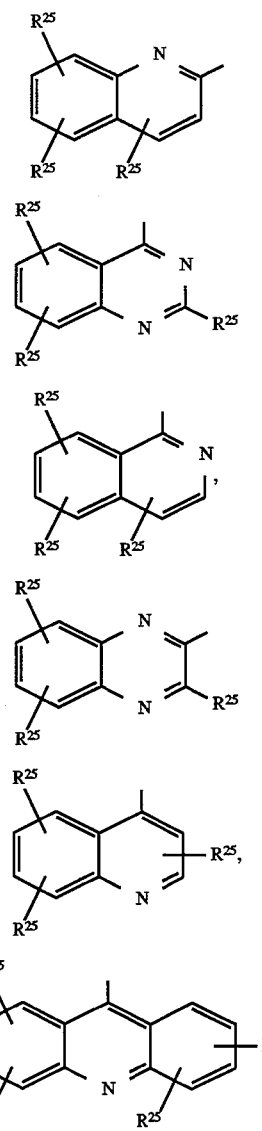

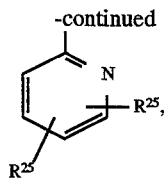

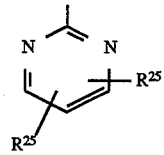

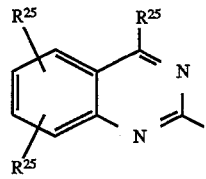

R⁹ is O, CH₂, C(O) or CF₂;

R²⁵ is hydrogen, alkyl (1–6C), OR²⁶, C(O)R²⁶, C(O)OR²⁶, CN, NO₂, N(CH₃)₂, SO or SO₂ wherein R²⁶ is alkyl (1–6C) or substituted alkyl (1–6C), or two R²⁵ together on the same ring form a 5-membered aromatic ring comprising carbon atoms and 1 or 2 atoms or groups selected from the group consisting of S, O, N and N(CH₃)₂, provided that no adjacent atoms are both O, or two R²⁵ together on the same ring form a 6-membered aromatic ring comprising carbon atoms and 0, 1 or 2 nitrogen atoms, provided that there is no more than one N(CH₃)₂ group in any single protecting group; and X is oxygen (O) or sulfur (S).

3. The compound of claim 2 wherein R is H, F, O-methyl, O-ethyl, or O-allyl; R⁶ is O; and B is adenine, guanine, cytosine, thymine, uracil, 5-methylcytosine, N⁶-benzoyl-7-deazaadenine, N²-isobutyryl-7-deazaguanine, 5-(1-propynyl)uracil, 5-(1-propynyl)cytosine, N⁶-benzoyladenine, N²-isobutyrylguanine, N⁴-benzoylcytosine, N⁴-formamidinylcytosine, N⁴-formamidinyl-5-(1-propynyl)cytosine, N⁴-formamidinyl-5-methylcytosine or N⁴-benzoyl-5-methylcytosine.

4. The compound of claim 2 wherein R¹ and R² are both methyl, ethyl, propyl, isopropyl, butyl, isobutyl, t-butyl, phenyl, 1- or 2-naphthyl, 2-, 3- or 4-cyanophenyl, 2-, 3- or 4-methylphenyl, 2-, 3- or 4-ethylphenyl, 2-, 3- or 4-methoxyphenyl, 2-, 3- or 4-nitrophenyl, 2-, 3- or 4-fluorophenyl, 2-, 3- or 4-pyridinyl, 2-, 4- or 5-pyrimidinyl, 2-, 4- or 5-oxazolyl, 2-, 4- or 5-thiazolyl, 2- or 3-thienyl or 2- or 3-furanyl.

5. The compound of claim 4 wherein R is H, F, O-methyl, O-ethyl, or O-allyl; R⁶ is O; $R^{7B}$ is 4,4'-dimethoxytrityl; and B is adenine, guanine, cytosine, thymine, uracil, 5-methylcytosine, N⁶-benzoyl-7-deazaadenine, N²-isobutyryl-7-deazaguanine, 5-(1-propynyl)uracil, 5-(1-propynyl)cytosine, N⁶-benzoyladenine, N²-isobutyrylguanine, N⁴-benzoylcytosine, N⁴-formamidinylcytosine, N⁴-formamidinyl-5-(1-propynyl)cytosine, N⁴-formamidinyl-5-methylcytosine or N⁴-benzoyl-5-methylcytosine.

6. The compound of claim 4 wherein R is H, F, O-methyl, O-ethyl, or O-allyl; R⁶ is O; and $R^{7D}$ has the structure 34

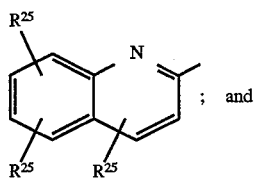  34

B is adenine, guanine, cytosine, thymine, uracil, 5-methylcytosine, 7-deazaadenine, 7-deazaguanine, 5-(1-propynyl)uracil, 5-(1-propynyl)cytosine, $N^6$-benzoyladenine, $N^2$-isobutyrylguanine, $N^4$-benzoylcytosine, $N^4$-formamidinylcytosine, $N^4$-formamidinyl-5-(1-propynyl)cytosine, $N^4$-formamidinyl-5-methylcytosine or $N^4$-benzoyl-5-methylcytosine.

7. The compound of claim 6 wherein $R^{25}$ is H.

8. The compound of claim 1 wherein $R^{74}$ is acetyl or benzoyl.

9. The compound of claim 1 wherein $R^3$ is $C(O)R^4$, $Si(R^{47})(R^{48})(R^{49})$, benzyl, FMOC or phenoxyacetyl wherein $R^4$ is alkyl (1–18C), aryl (1–18C) or substituted alkyl (1–18C); $R^{47}$, $R^{48}$ and $R^{49}$ are independently methyl, ethyl, isopropyl, t-butyl or phenyl provided that at least one of $R^{47}$, $R^{48}$ and $R^{49}$ is isopropyl, t-butyl or phenyl.

10. The compound of claim 1 wherein $R^3$ is t-butyldiphenylsilyl, pivaloyl, benzyl or FMOC; $R^6$ is oxygen; and $R^1$ and $R^2$ are both methyl, ethyl, propyl, isopropyl, butyl, isobutyl, t-butyl, phenyl, 1- or 2-naphthyl, 2-, 3- or 4-cyanophenyl, 2-, 3- or 4-methylphenyl, 2-, 3- or 4-ethylphenyl, 2-, 3- or 4-methoxyphenyl, 2-, 3- or 4-nitrophenyl, 2-, 3- or 4-fluorophenyl, 2-, 3- or 4-pyridinyl, 2-, 4- or 5-pyrimidinyl, 2-, 4- or 5-oxazolyl, 2-, 4- or 5-thiazolyl, 2- or 3-thienyl or 2- or 3-furanyl.

11. The compound of claim 1 wherein $R^{7D}$ is a compound of structure 34

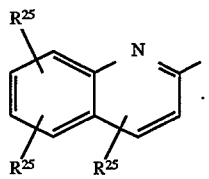  34

12. The compound of claim 1 wherein $R^6$ is oxygen.

13. The compound of claim 12 having the structure 3, 4, 5, 6, 7, 7a, 8, 8a, 9, 10, 11g, 11h, 12b, 13b, 30, 30a, 31 or 31a

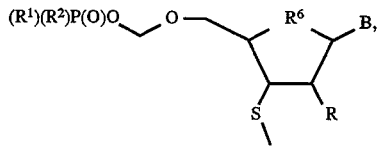  3

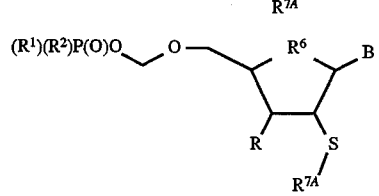  4

-continued

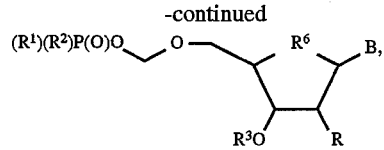  5

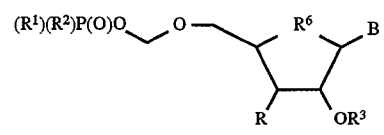  6

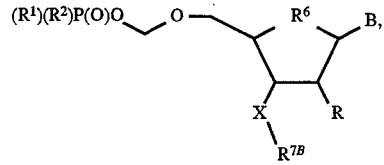  7

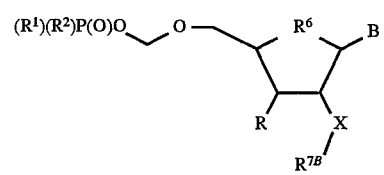  8

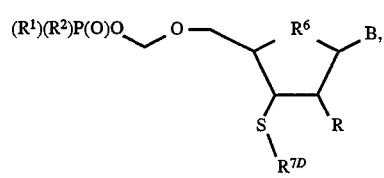  7a

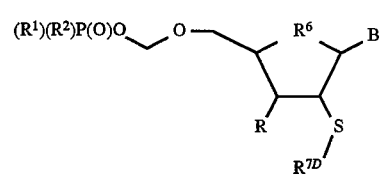  8a

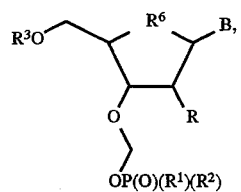  9

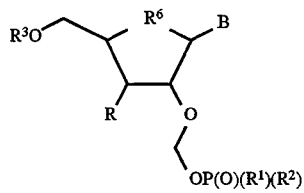  10

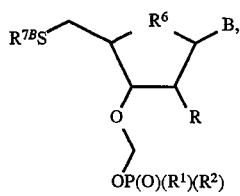  30

-continued

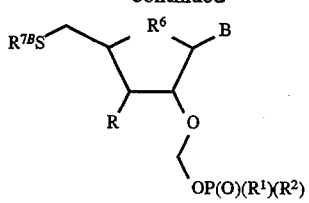

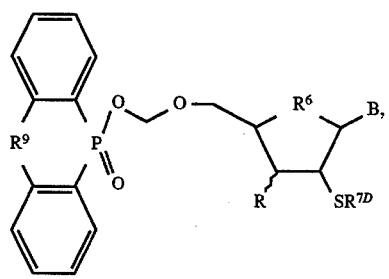
11g

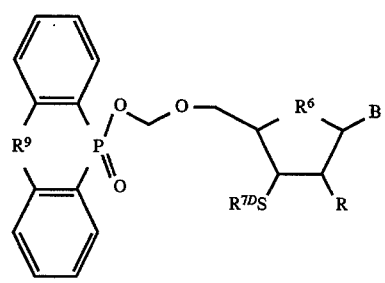
11h

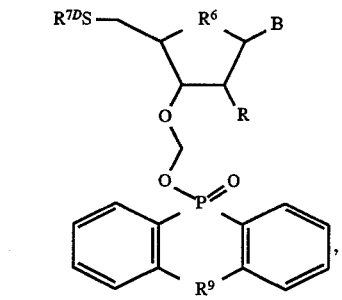
12b

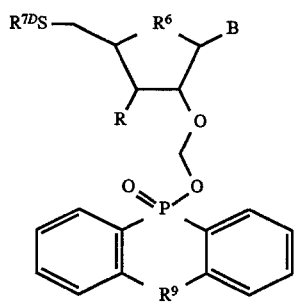
13b

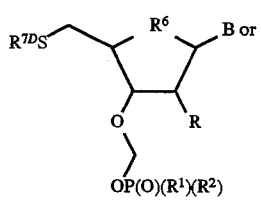
30a

-continued

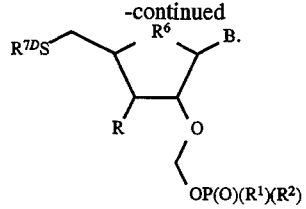
31

14. The compound of claim 13 wherein $R^{7D}$ is a compound of structure 34, 36, 38 or 39

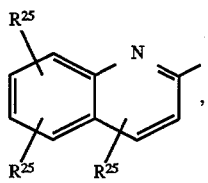
34

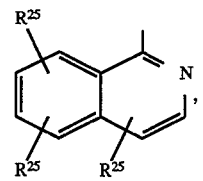
36

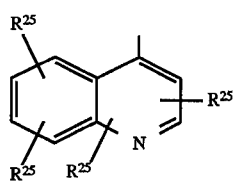
38 or

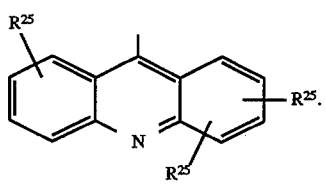
39

15. The compound of claim 14 wherein $R^{25}$ is hydrogen.

16. The compound of claim 15 wherein R is H, F, O-methyl, O-ethyl, or O-allyl and B is adenine, guanine, cytosine, thymine, uracil, 5-methylcytosine, $N^6$-benzoyl-7-deazaadenine, $N^2$-isobutyryl-7-deazaguanine, 5-(1-propynyl)uracil, 5-(1-propynyl)cytosine, $N^6$-benzoyladenine, $N^2$-isobutyrylguanine, $N^4$-benzoylcytosine, $N^4$-formamidinylcytosine, $N^4$-formamidinyl-5-(1-propynyl)cytosine, $N^4$-formamidinyl-5-methylcytosine or $N^4$-benzoyl-5-methylcytosine.

17. The compound of claim 15 wherein $R^1$ and $R^2$ are both methyl, ethyl, propyl, isopropyl, butyl, isobutyl, t-butyl, phenyl, 1- or 2-naphthyl, 2-, 3- or 4-cyanophenyl, 2-, 3- or 4-methylphenyl, 2-, 3- or 4-ethylphenyl, 2-, 3- or 4-methoxyphenyl, 2-, 3- or 4-nitrophenyl, 2-, 3- or 4-fluorophenyl, 2-, 3- or 4-pyridinyl, 2-, 4- or 5-pyrimidinyl, 2-, 4- or 5-oxazolyl, 2-, 4- or 5-thiazolyl, 2- or 3-thienyl or 2- or 3-furanyl.

18. The compound of claim 14 wherein $R^{7D}$ is a compound of structure 34

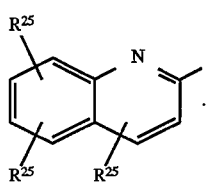

19. The compound of claim 18 wherein $R^{25}$ is hydrogen.

20. The compound of claim 19 wherein R is H, F, O-methyl, O-ethyl, or O-allyl and B is adenine, guanine, cytosine, thymine, uracil, 5-methylcytosine, $N^6$-benzoyl-7-deazaadenine, $N^2$-isobutyryl-7-deazaguanine, 5-(1-propynyl)uracil, 5-(1-propynyl)cytosine, $N^6$-benzoyladenine, $N^2$-isobutyrylguanine, $N^4$-benzoylcytosine, $N^4$-formamidinylcytosine, $N^4$-formamidinyl-5-(1-propynyl)cytosine, $N^4$-formamidinyl-5-methylcytosine or $N^4$-benzoyl-5-methylcytosine.

21. The compound of claim 19 wherein $R^1$ and $R^2$ are both methyl, ethyl, propyl, isopropyl, butyl, isobutyl, t-butyl, phenyl, 1- or 2-naphthyl, 2-, 3- or 4-cyanophenyl, 2-, 3- or 4-methylphenyl, 2-, 3- or 4-ethylphenyl, 2-, 3- or 4-methoxyphenyl, 2-, 3- or 4-nitrophenyl, 2-, 3- or 4-fluorophenyl, 2-, 3- or 4-pyridinyl, 2-, 4- or 5-pyrimidinyl, 2-, 4- or 5-oxazolyl, 2-, 4- or 5-thiazolyl, 2- or 3-thienyl or 2- or 3-furanyl.

* * * * *